(12) United States Patent
Gusky

(10) Patent No.: US 12,100,497 B1
(45) Date of Patent: Sep. 24, 2024

(54) POPULATION-BASED IMMUNE RESCUE VIA HERD IMMUNITY MEDIATED BY CELLS

(71) Applicant: Jeff Gusky, Holly Lake Ranch, TX (US)

(72) Inventor: Jeff Gusky, Holly Lake Ranch, TX (US)

(73) Assignee: Channel Content Company LLC, Sheridan, WY (US)

( * ) Notice: Subject to any disclaimer, the term of this patent is extended or adjusted under 35 U.S.C. 154(b) by 0 days.

(21) Appl. No.: 18/227,919

(22) Filed: Jul. 29, 2023

(51) Int. Cl.
| | |
|---|---|
| G16H 20/10 | (2018.01) |
| A23L 33/00 | (2016.01) |
| A23L 33/155 | (2016.01) |
| G16H 10/40 | (2018.01) |
| G16H 20/60 | (2018.01) |
| G16H 40/67 | (2018.01) |
| G16H 50/80 | (2018.01) |

(52) U.S. Cl.
CPC .............. *G16H 20/10* (2018.01); *A23L 33/00* (2016.08); *G16H 10/40* (2018.01); *G16H 20/60* (2018.01); *G16H 40/67* (2018.01); *G16H 50/80* (2018.01); *A23L 33/155* (2016.08)

(58) Field of Classification Search
None
See application file for complete search history.

(56) References Cited

PUBLICATIONS

Harris, B, "Could high humidity slow the spread of COVID-19?" WFAA-TV, WFAA.com, published Jul. 11, 2020, downloaded Jan. 25, 2024 from "https://www.wfaa.com/article/news/health/coronavirus/could-high-humidity-slow-spread-coronavirus/287-6aa63537-1ed7-47ef-baa4-64716d29c730" (Year: 2020).*
U.S. Bureau of Labor Statistics, Population—With a Disability, 16 Years and over [LNU00074597], retrieved from FRED, Federal Reserve Bank of St. Louis; https://fred.stlouisfed.org/series/LNU00074597, Aug. 12, 2023.
Thomas J. Britt, Paul Correia, Patrick Hurley, Mike Krohn, Tony Lasala, Rick Leavitt, Robert Lumia, Cynthia S. Macdonald, Patrick Nolan, Steve Rulis, Bram Spector, Group Life COVID-19 Mortality Survey Report, Aug. 2022, SOA Research Institute, https://www.soa.org/resources/experience-studies/2022/group-life-covid-19-mortality/.
Moriyama M, Hugentobler WJ, Iwasaki A., Seasonality of Respiratory Viral Infections. Annu Rev Virol. Sep. 29, 2020;7(1):83-101. doi: 10.1146/annurev-virology-012420-022445. Epub Mar. 20, 2020. PMID: 32196426.
Zheng D, Liwinski T, Elinav E., Interaction between microbiota and immunity in health and disease. Cell Res. Jun. 2020;30(6):492-506. doi: 10.1038/s41422-020-0332-7. Epub May 20, 2020. PMID: 32433595; PMCID: PMC7264227.
Delgado JF, Vidal-Pla M, Moya MC, Espasa M, Casabella A, Seda M, Calvet J, Gratacós J, Serrano RM, Peña P., SARS-CoV-2 Spike Protein Vaccine-Induced Immune Imprinting Reduces Nucleocapsid Protein Antibody Response in SARS-CoV-2 Infection. J Immunol Res. Jul. 29, 2022;2022:8287087. doi: 10.1155/2022/8287087. PMID: 35935586; PMCID: PMC9355782.
Wang Q, Iketani S, Li Z, Liu L, Guo Y, Huang Y, Bowen AD, Liu M, Wang M, Yu J, Valdez R, Lauring AS, Sheng Z, Wang HH, Gordon A, Liu L, Ho DD.,Alarming antibody evasion properties of rising SARS-CoV-2 BQ and XBB subvariants. Cell. Jan. 19, 2023;186(2):279-286.e8. doi: 10.1016/j.cell.2022.12.018. Epub Dec. 14, 2022. PMID: 36580913; PMCID: PMC9747694.
Yonker LM, Swank Z, Bartsch YC, Burns MD, Kane A, Boribong BP, Davis JP, Loiselle M, Novak T, Senussi Y, Cheng CA, Burgess E, Edlow AG, Chou J, Dionne A, Balaguru D, Lahoud-Rahme M, Arditi M, Julg B, Randolph AG, Alter G, Fasano A, Walt DR., Circulating Spike Protein Detected in Post- COVID-19 mRNA Vaccine Myocarditis. Circulation. Mar. 14, 2023;147(11):867-876. doi: 10.1161/CIRCULATIONAHA. 122.061025. Epub Jan. 4, 2023. PMID: 36597886; PMCID: PMC10010667.
Harrison NL, Sachs JD, A call for an independent inquiry into the origin of the SARS-CoV-2 virus. Proc Natl Acad Sci U S A. May 24, 2022;119(21):e2202769119. doi: 10.1073/pnas.2202769119. Epub May 19, 2022. PMID: 35588448; PMCID: PMC9173817.
Bortolotti D, Gentili V, Rizzo S, Rotola A, Rizzo R.,SARS-CoV-2 Spike 1 Protein Controls Natural Killer Cell Activation via the HLA-E/NKG2A Pathway. Cells. Aug. 26, 2020;9(9):1975. doi: 10.3390/cells9091975. PMID: 32859121; PMCID: PMC7563485.
Qu P, Evans JP, Kurhade C, Zeng C, Zheng YM, Xu K, Shi PY, Xie X, Liu SL . . . Determinants and Mechanisms Of the Low Fusogenicity and High Dependence on Endosomal Entry of Omicron Subvariants. mBio. Feb. 28, 2023;14(1):e0317622. doi: 10.1128/mbio. 03176-22. Epub Jan. 10, 2023. PMID: 36625591; PMCID: PMC9972997.
Varghese R, Kumar D, Sharma R., Global threat from novel SARS-CoV-2 variants, BF.7, XBB.1.5, BQ.1, and BQ.1.1: variants of concern? Hum Cell. May 2023;36(3):1218-1221. doi: 10.1007/s13577-023-00903-9. Epub Mar. 31, 2023. PMID: 37000399; PMCID: PMC10063927.
Arundel AV, Sterling EM, Biggin JH, Sterling Tdir D., Indirect health effects of relative humidity in indoor environments. Environ Health Perspect. Mar. 1986;65:351-61. doi: 10.1289/ehp.8665351. PMID: 3709462; PMCID: PMC1474709.

(Continued)

*Primary Examiner* — G. Steven Vanni
(74) *Attorney, Agent, or Firm* — Levine's Tech Consulting LLC; Frank E. Levine

(57) ABSTRACT

An approach is disclosed for activating cell-mediated herd immunity (CMHI) in a group of people. A scalable infrastructure is provided with one or more compliance protocol targets to facilitate activation of at least one of the four types of individual cell-mediated immunity (CMI): absolute humidity CMI, vitamin D CMI, gut microbiome CMI, and antiviral priming CMI, in the group of people. The activation is for at least one of: absolute humidity CMHI, vitamin D CMHI, gut microbiome CMHI, and antiviral priming CMHI in the group of people. The CMHI is achieved in the group of people when the compliance protocol targets are achieved.

26 Claims, 36 Drawing Sheets

(56) References Cited

PUBLICATIONS

Figure 1:
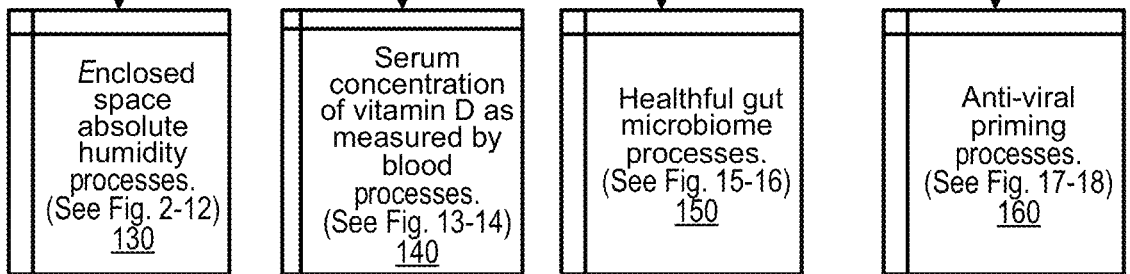

Jeffrey S Haman, Melvin Kohn, Absolute humidity modulates influenza survival, transmission, and seasonality, PNAS, Mar. 3, 2009, vol. 106, No. 9, 3243-3248, downloaded from https://www.pnas.org on Aug. 13, 2023.

Drstream, White Paper, Using Humidification To Reduce the Transmission of Viruses, 2020, https://www.mmsus.com/wp-content/uploads/2020/12/white-paper_using-humidification-to-reduce-the-transmission-of-viruses.pdf.

Sultan S, Taimuri U, Basnan SA, Ai-Orabi WK, Awadallah A, Almowald F, Hazazi A., Low Vitamin D and Its Association with Cognitive Impairment and Dementia. J Aging Res. Apr. 30, 2020;2020:6097820. doi: 10.1155/2020/6097820. PMID: 32399297; PMCID: PMC7210535.

Reiman JM, Das B, Sindberg GM, Urban MD, Hammerlund MEM, Lee HB, Spring KM, Lyman-Gingerich J, Generous AR, Koep TH, Ewing K, Lilja P, Enders FT, Ekker SC, Huskins WC, Fadel HJ, Pierret C., Humidity as a non-pharmaceutical intervention for influenza A. PLoS One. Sep. 25, 2018;13(9):e0204337. doi: 10.1371/journal.pone.0204337. PMID: 30252890; PMCID: PMC6155525.

Bae JH, Choe HJ, Holick MF, Lim S., Association of vitamin D status with COVID-19 and its severity : Vitamin D and COVID-19: a narrative review. Rev Endocr Metab Disord. Jun. 2022;23(3):579-599. doi: 10.1007/s11154-021-09705-6. Epub Jan. 4, 2022. PMID: 34982377; PMCID: PMC8724612.

Borsche L, Glauner B, Von Mendel J., COVID-19 Mortality Risk Correlates Inversely with Vitamin D3 Status, and a Mortality Rate Close to Zero Could Theoretically Be Achieved at 50 ng/ml 25(OH)D3: Results of a Systematic Review and Meta-Analysis. Nutrients. Oct. 14, 2021;13(10):3596. doi: 10.3390/nu13103596. PMID: 34684596; PMCID: PMC8541492.

Jiaquan Xu, M.D., Sherry L. Murphy, B.S., Kenneth D. Kochanek, M.A., and Elizabeth Arias, Ph.D., Mortality in the United States, 2021, NCHS Data Brief, No. 456, Dec. 2022.

Shorobi FM, Nisa FY, Saha S, Chowdhury MAH, Srisuphanunt M, Hossain KH, Rahman MA., Quercetin: A Functional Food-Flavonoid Incredibly Attenuates Emerging and Re-Emerging Viral Infections through Immunomodulatory Actions. Molecules. Jan. 17, 2023;28(3):938. doi: 10.3390/molecules28030938. PMID: 36770606; PMCID: PMC9920550.

Mahmud S, Afrose S, Biswas S, Nagata A, Paul GK, Mita MA, Hasan MR, Shimu MSS, Zaman S, Uddin MS, Islam MS, Saleh MA., Plant-derived compounds effectively inhibit the main protease of SARS-COV-2: An in silico approach. PLoS One. Aug. 23, 2022;17(8):e0273341. doi: 10.1371/journal.pone.0273341. PMID: 35998194; PMCID: PMC9398018.

Miller & Newberg Consulting Actuaries, Three Years into COVID, Insurance Death Claims are Still Rising, Mar. 24, 2023, http://www.miller-newberg.com/index.php/three-years-into-covid-insurance-death-claims-are-still-rising/.

Lin G, Hamilton A, Gatalo O, Haghpanah F, Igusa T, Klein E., Investigating the effects of absolute humidity and movement on COVID-19 seasonality in the United States. Sci Rep. Oct. 6, 2022;12(1):16729. doi: 10.1038/s41598-022-19898-8. PMID: 36202875; PMCID: PMC9537426.

Liu J, Zhou J, Yao J, Zhang X, Lil, Xu X, He X, Wang B, Fu S, Niu T, Yan J, Shi Y, Ren X, Niu J, Zhu W, Li S, Luo B, Zhang K., Impact of meteorological factors on the COVID-19 transmission: A multi-city study in China. Sci Total Environ. Jul. 15, 2020;726:138513. doi: 10.1016/j.scitotenv.2020.138513. Epub Apr. 9, 2020. PMID: 32304942; PMCID: PMC7194892.

Zanza C, Romenskaya T, Manetti AC, Franceschi F, La Russa R, Bertozzi G, Maiese A, Savioli G, Volonnino G, Longhitano Y., Cytokine Storm in COVID-19: Immunopathogenesis and Therapy. Medicina (Kaunas). Jan. 18, 2022;58(2):144. doi: 10.3390/medicina58020144. PMID: 35208467; PMCID: PMC8876409.

Ryabkova VA, Churilov LP, Shoenfeld Y., Influenza infection, SARS, MERS and COVID-19: Cytokine storm—The common denominator and the lessons to be learned. Clin Immunol. Feb. 2021;223:108652. doi: 10.1016/j. clim.2020.108652. Epub Dec. 14, 2020. PMID: 33333256; PMCID: PMC7832378.

Rhodes JM, Subramanian S, Laird E, Griffin G, Kenny RA., Perspective: Vitamin D deficiency and COVID-19 severity—plausibly linked by latitude, ethnicity, impacts on cytokines, ACE2 and thrombosis. J Intern Med. Jan. 2021;289(1):97-115. doi: 10.1111/joim. 13149. Epub Jul. 22, 2020. PMID: 32613681; PMCID: PMC7361294.

Mendes V, Galvão I, Vieira AT., Mechanisms by Which the Gut Microbiota Influences Cytokine Production and Modulates Host Inflammatory Responses. J Interferon Cytokine Res. Jul. 2019; 39(7):393-409. doi: 10.1089/ ir.2019.0011. Epub Apr. 23, 2019. PMID: 31013453.

Khatoon S, Kalam N, Shaikh MF, Hasnain MS, Hafiz AK, Ansari MT., Nanoencapsulation of Polyphenols as Drugs and Supplements for Enhancing Therapeutic Profile—A Review. Curr Mol Pharmacol. 2022; 15(1):77-107. doi: 10.2174/1874467214666210922120924. PMID: 34551693.

Worldometer, COVID-Coronavirus Statistics, Jul. 12, 2023, https://www.worldometers.info/coronavirus/#countries.

Bryan Siepert, Adafruit TE MS8607 PHT Sensor, Dec. 1, 2022, https://learn.adafruit.com/adafruit-te-ms8607-pht-sensor.

Bosch, BME280 Integrated Environmental Unit, Bosch Sensortec, Jan. 2022, https://www.bosch-sensortec.com/media/boschsensortec/downloads/product_flyer/bst-bme280-f1000.pdf.

\* cited by examiner

Absolute humidity safety process 200

```
┌─────────────────────────────────────────────────────────────────┐
│ Facilitating activation of cell-mediated immunity (CMI) on       │
│ mucosal surfaces in a respiratory tract of people in an enclosed │
│ space                                                            │
│ 210                                                              │
└─────────────────────────────────────────────────────────────────┘
                              │
                              ▼
                  ◇ Is absolute humidity level safe 220 ◇
                    │                                  │
                  Y │                                  │ N
                    │    ┌──────────────┬──────────────┐
                    │    │ Integrated   │ Non-         │
                    │    │ humidifier   │ Integrated   │
                    │    │ into HVAC    │ HVAC system  │
                    │    │ system 230   │ 240          │
                    │    └──────┬───────┴──────┬───────┘
                    │           ▼              ▼
                    │        ┌─────────────────┐
                    │        │ Run humidifier  │◄──
                    │        │      250        │
                    │        └─────────────────┘
                    ▼
                ┌────────┐
                │  End   │
                │  260   │
                └────────┘
```

*FIG. 2*

Activation of cell-mediated immunity (CMI) on mucosal surfaces in a respiratory tract of an individual 300

Providing a device disseminating moisturized air in a submicron (less than one micron) particle size to the individual ensuring the individual inhales moisturized air with a high concentration of absolute humidity. Breathing the moisturized air enables distribution of water vapor with high absolute humidity into a deepest parts of the respiratory tract. The device may have a mask that covers nose and mouth.
310

Absolute humidity disseminated by the device is at least 10 g/m³
320

Marketing usage of the device to include a set of scenarios wherein the individual has breathed in dry air or has been exposed to unknown biohazards
330

Usage scenarios include departing a plane, home health practitioners after leaving a client's home, handyman or service technician after leaving a serviced premise
340

End
350

*FIG. 3*

Indicating viral safety of enclosed spaces 400

Receiving absolute humidity (AH) values AHV (AHV1, AHV2, ..., AHVn) from a set of sensors S (S1, S2, ..., Sn) placed at locations L (L1, L2, ..., Ln) 410

Comparing the received absolute humidity values AHV (AHV1, AHV2, ...AHVi, AHVn) to a viral safety safe value to determine a viral safety assessment of one of safe and not safe 420

Send received data to a remote location 430

Store received data in a database 440

Are all values safe? 450 —N→ Perform first action process if not safe (See Fig. 5) 460

Y

Perform provide indication of indoor safety process (See Fig. 6) 470

End 480

*FIG. 4*

Sensor APIs 1100

Sensor Management 1110

| API | Description |
|---|---|
| sOpen() | Open a sensor |
| sClose() | Close a sensor |
| sQuery() | Query information about a sensor |
| sLMap() | Map a location to a sensor |
| sOMap() | Map owner to a sensor |
| sErase() | Erase information about a sensor |
| sChng() | Change properties of a sensor |
| sRead() | Read values of sensor for a range of time |

*FIG. 11*

Achieving a serum concentration of vitamin D as measured by blood test to an upper end of a normal range in an individual 1300

Providing a user interface supporting a step-by-step interaction with each individual in the group of people facilitating achieving a vitamin D level in an upper end of a normal range for the each individual in a group of people
1310

Identifying a time and place, by the user interface, for an initial testing of the vitamin D level for the group of people where the initial testing of the vitamin D level includes a testing of calcium and magnesium and utilizes blood drawing professionals
1320

Analyzing results of the initial testing to identify an initial tailored regimen for the each individual in the group of people
1330

Shipping an initial treatment pack to an individual based on the initial tailored regimen for the each individual in the group of people
1340

Retesting the vitamin D level to identify a maintenance dosage of vitamin D for the each individual in the group of people after the initial treatment pack is consumed
1350

Retesting the vitamin D level after the maintenance dosage of vitamin D for the each individual in the group of people is consumed to verify the maintenance dosage
1360

End
1370

*FIG. 13*

Utilizing mass testing and treatment to elevate a vitamin D level in a group of people into a viral safe range 1400

Providing a user interface supporting interactive communication with an automated system that accesses a Health Insurance Portability and Accountability Act (HIPAA) compliant data base 1410

Applying a first mass blood extraction procedure to the group of people to form a first set of blood vials 1420

Sending the first set of blood vials for analyses of calcium, magnesium, and serum vitamin D to form a first set of test results 1430

Analyzing the first set of test results to identify a first tailored regimen for each individual in the group of people. Sending the first tailored regimen to the each individual in the group of people 1440

Applying a second mass blood extraction procedure to the group of people to form a second set of blood vials. Sending the second set of blood vials for analysis of serum vitamin D level and calcium to form a second set of test results 1450

Utilizing the second set of test results to determine a preliminary daily maintenance dosage 1460

Applying a third mass blood extraction procedure to the group of people to form a third set of blood vials after ingesting the preliminary daily maintenance dosage by the group of people for a period of time. Analyzing the third set of blood vials for serum vitamin D level, calcium, and magnesium to form a third set of test results 1470

Utilizing the third set of test results to confirm the preliminary daily maintenance dosage is maintaining the individual serum vitamin D level in the viral safe range or modify daily maintenance dosage accordingly 1480

Applying a yearly mass blood extraction procedure to the group of people to form a yearly set of blood vials after ingesting a previous maintenance dosage by the group of people for a year. Analyzing the yearly set of blood vials for serum vitamin D level, calcium, and magnesium to form a yearly set of test results 1482

Utilizing the yearly set of test results to confirm the yearly daily maintenance dosage is maintaining the serum vitamin D level in the viral safe range or to modify daily maintenance dosage accordingly 1484

End 1490

*FIG. 14*

Facilitating activation of gut microbiome induced cell-mediated herd immunity (CMHI) by activating gut microbiome induced individual cell-mediated immunity (CMI)   1500

Probiotics include live microorganisms which when administered in adequate amounts confer a health benefit on the host 1512

Elements of the prebiotic may be special plant fibers that help healthy bacteria grow in the gut, making the digestive system work better which may include green banana flower
1514

Elements of micronutrients may include selenium, zinc, and magnesium
1516

*Ingredients optionally include: N-acetyl cysteine (NAC), quercetin, nattokinase, vitamin C, fucoidan, and N-acetyl glucosamine (NAG).* 1518

Manufacturing a consumable product in a form of a powder to be ingested by the group of people wherein the consumable product includes *prebiotic, probiotic, and micronutrients*
1510

*Marketing the consumable product for the activation of gut microbiome induced CMHI and supplying directions for using and consuming the consumable product*
1520

*Activating the CMHI in the group of people automatically based on following the directions for usage and consumption of the consumable product*
1530

Targeting facilities selected from a group consisting of schools, prisons, jails, group homes, residential treatment centers, nursing homes, assisted living centers, factories, offices, hospitals, cruise ships, and senior residential facilities
1540

End
1500

*FIG. 15*

Healthful gut microbiome process 1600

*Non-pharmaceutical phytochemicals include* properties selected from a group consisting of anti-cancer, neuroprotection, antioxidant, anti-prion, anti-amyloid, mitochondrial rehabilitation, and autophagy
1605

Providing a protocol for restoring gut microbiome wherein the protocol includes a daily consumption of a product received in a form of a powder to be ingested by a group of people wherein the consumable product includes select prebiotics, probiotics, and Non-pharmaceutical phytochemicals which may be delivered in a smoothie utilizing the powder for administration to a group of people in institutional settings, such as, schools, nursing homes, factories, prisons, etc. Consumption by a group of people results in gut microbiome induced CMHI.
1610

*FIG. 16*

Facilitating activation of anti-viral priming induced cell-mediated herd immunity (CMHI) by activating anti-viral induced individual cell-mediated immunity (CMI) for long term usage 1700

Non-pharmaceutical phytochemicals optionally include artemisinin, berberine, hesperidin/hespertin, luteolin, bacopa, fisetin, silymarin, taurine, and bromelain 1714

Non-pharmaceutical phytochemicals may include Curcumin, Quercetin, and Boswellic Acid 1712

Non-pharmaceutical phytochemicals include properties selected from a group consisting of anti-cancer, neuroprotection, anti-oxidant, anti-prion, anti-amyloid, mitochondrial rehabilitation, and autophagy 1716

Manufacturing a consumable product in a form of an ingestible cream delivered orally with nanotechnology enhanced bioavailability and sealed in an oxygen proof sachet wherein the consumable product includes *non-pharmaceutical phytochemicals with intrinsic biomolecular properties that inhibit enzymes critical to viral replication* 1710

*Marketing the consumable

Assessing and mitigating risk of spike protein induced immune suppression and endothelial inflammation 2300

Providing a user interface supporting interactive communication with an automated system that accesses a HIPAA compliant data base 2305

Applying a first blood extraction procedure to a plurality of people to form a first set of blood vials 2310

Sending the first set of blood vials for analysis factors associated with natural killer cell (NK) absolute cell count test combined with NK cell function test combined with endothelial inflammation assessment panel 2315

Receiving a first set of results from the sending of the first set of blood vials 2320

Comparing the first set of results to established normal ranges to create the spike protein induced immune suppression and endothelial inflammation risk profile in the plurality of people 2325

Offering, by the user interface, a first group of people having the spike protein induced immune suppression and endothelial inflammation risk profile exceeding a predetermined established normal ranges, a risk mitigation program 2330

Enrolling each individual in the first group of people accepting the offered risk mitigation program in the risk mitigation program to form a group of risk mitigation enrolled people 2335

Applying a second mass blood extraction procedure to the group of risk mitigation enrolled people to form a second set of blood vials 2340

Sending the second set of blood vials for analysis factors associated with natural killer cell (NK) absolute cell count test combined with NK cell function test combined with endothelial inflammation assessment panel 2345

Receiving a second set of results from the sending of the second set of blood vials 2350

Comparing the second set of results to established normal ranges to an updated immune suppression and endothelial inflammation risk profile in the group of risk mitigation enrolled people 2355

Assessing the risk mitigation program as effective when the updated spike protein induced immune suppression and endothelial inflammation risk profile does not exceed the predetermined risk level 2360

If still at risk, repeat risk mitigation protocol and retest 2370

End 2365

*FIG. 23*

```
                    Recruiting, credentialing, onboarding, and training qualified service providers supporting cell-
                              mediated herd immunity™ (CMHI) for community health  2500
```

| Receiving endorsement of community leaders, based on promoting community service to address urgent public health needs, request cooperation by school officials to share alumni lists of selected occupations for recruitment of registry applicants  2502 |
|---|

↓

| Recruiting potential service providers to submit an application to become part of a registry of qualified service targeted toward services that facilitate CMHI 2505 |
|---|

↓

| Vetting a set of service provider applicants according to an acceptance criteria to classifying each service provider applicant in the set of service provider applicants as one of invited to apply, added to a stand-by list for future application, and not invited 2510 |
|---|

↓

| Credentialing applicants invited to submit applications to become members of the registry 2515 |
|---|

↓

| Onboarding the credentialed applicants 2520 |
|---|

↓

| Training the onboarded applicants 2525 |
|---|

↓

| Adding the trained applicants to the registry 2530 |
|---|

↓

| A first service is drawing blood and the alumni list includes phlebotomists, certified nurse assistants (CNA), respiratory therapists, paramedics, medical technologists, nurses (LVN/RN) 2540 |
|---|

↓

| When a work opportunity is available, each member of the registry is eligible to sign up for shifts for work opportunities 2550 |
|---|

↓

| A second services is collecting data pertaining to adapting existing heating, ventilation, and air conditioning (HVAC) systems to achieving a safe absolute humidity level and the alumni list includes HVAC technicians and mechanical engineers 2555 |
|---|

↓

| Collection of HVAC data is scheduled for a plurality of buildings and each member of the registry is eligible to sign up for a shift for the collecting of the HVAC data according to a schedule 2560 |
|---|

↓

End
2565

FIG. 25

Reducing company insurance premiums 2600

Measuring, by an independent auditor, a company specific risk profile including wellness and safety data 2605

Comparing the company specific risk profile to an aggregate pool of risk data for an insurance comparable risk pool derived from many companies to form a company specific risk reduction assessment 2610

Certifying the company specific risk reduction assessment, by the independent auditor, to qualify for lower insurance rates [disability, health, group life, workman's compensation, etc.] 2620

The wellness and safety data include workforce and premise liability aspects selected from a group consisting of outbreaks, accidents, injuries, chronic illness affecting workforce, and deaths 2625

Compensating for increased introduced risk data starting in 2021 including workforce absenteeism, disability, and excess mortality 2635

Interventions include enclosed space absolute humidity, serum concentration of vitamin D as measured by a blood test, healthful gut microbiome, and anti-viral priming 2650

Validating results of the company specific risk reduction assessment by an independent auditor separate from a viral safety company 2655

Company specific risk profile data may be collected and processed automatically and periodically, for example, weekly 2660

Comparing company specific risk profile metrics after following industry specific CMHI risk management protocols and interventions to other comparable industries which operate without the industry specific CMHI risk management protocols and interventions to establish the company specific risk reduction assessment (can further validate company specific risk profile using that company's previous risk profile history) 2665

End 2670

*FIG. 26*

1) Wi-Fi is a trademark of Wi-Fi Alliance.
2) Bluetooth is a trademark of Bluetooth SIG, Inc.
3) NFC is a trademark of Never Fame Over Currency, LLC.

User specific data
3200

Owner, contact info, (e.g. email)
3210

Access rights (granularity for access to the data per user, group, or process)
3220

Consent information: data owner, status of consent, consent expiration date (if any), details of consented access / use of data, e.g., data can be used for study at user specified granularity.
3230

Payment history
3240

Interaction history
3250

Current state
3260

Preferences
3270

Personally identifiable information (PII)
3280

*FIG. 32*

Dynamic on-demand assistance for facilitating cell-mediated herd immunity (CMHI) 3400

Training an artificial intelligence (AI) system to support user registration, user data collection, and user education tailored to achieving CMHI
3410

Receiving, by the AI system, information from registered users;
analyzing, by the AI system, the information to determine if a mobilization of specialists is needed for achieving CHMI
3420

Responsive to determining the mobilization of specialists is needed for achieving CHMI, utilizing a prediction algorithm to identify a target date and a target location at a target start time and a target duration for the mobilization of specialists.
Initiating an event booking for the target date at the target location for the mobilization of specialists
3430

Periodically perform event booking success prediction (See Fig. 35)
3440

Responsive to determining the outcome prediction is not successful, cancelling the event for the target date at the target location and reschedule event 3450

*FIG. 34*

POPULATION-BASED IMMUNE RESCUE VIA HERD IMMUNITY MEDIATED BY CELLS

BACKGROUND

The present invention relates to the induction of population-based immune defenses against potential bioweapons, and more particularly to the optimization of innate immunity against pathogens.

SUMMARY

Figure 35:
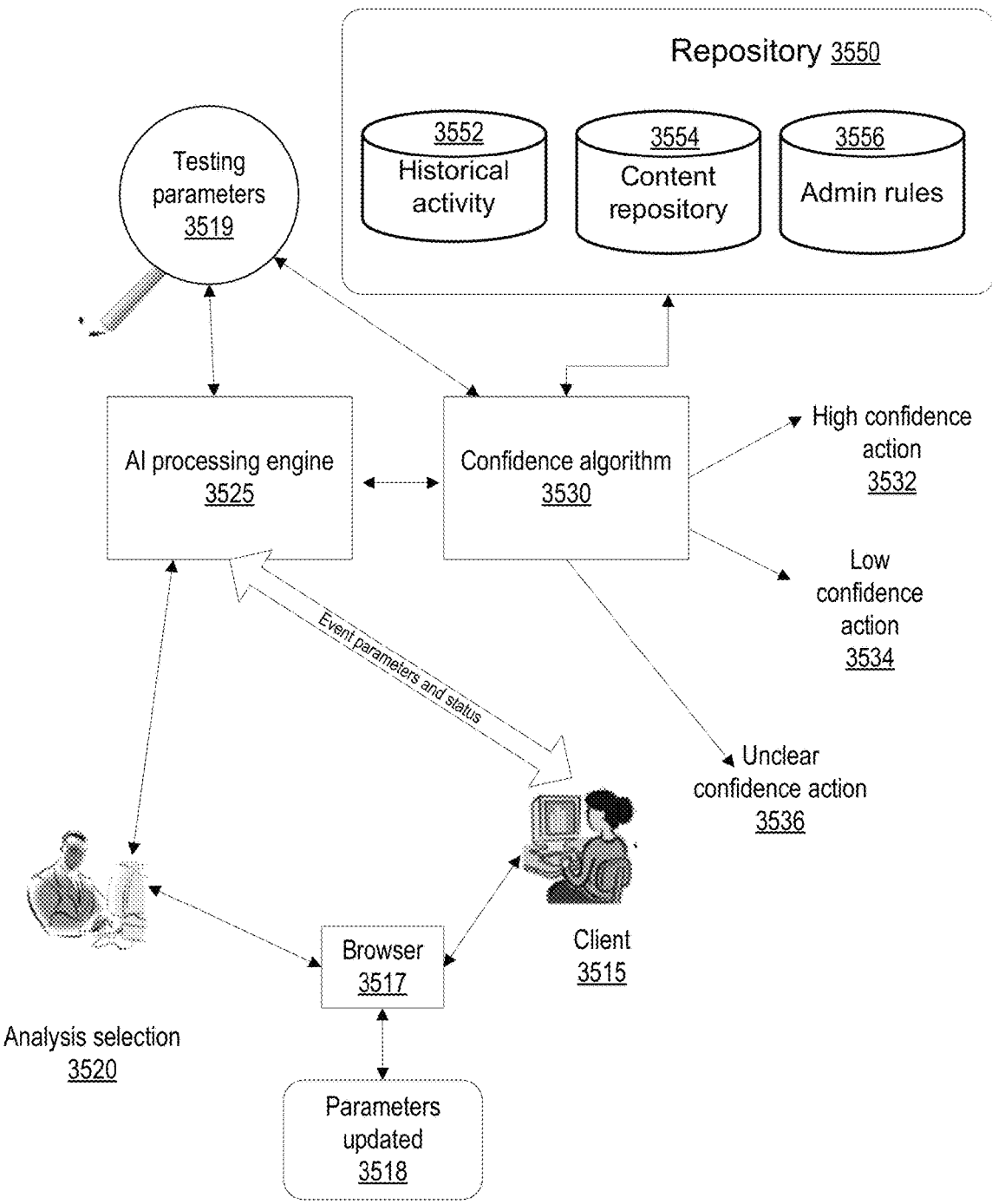
Figure 36:
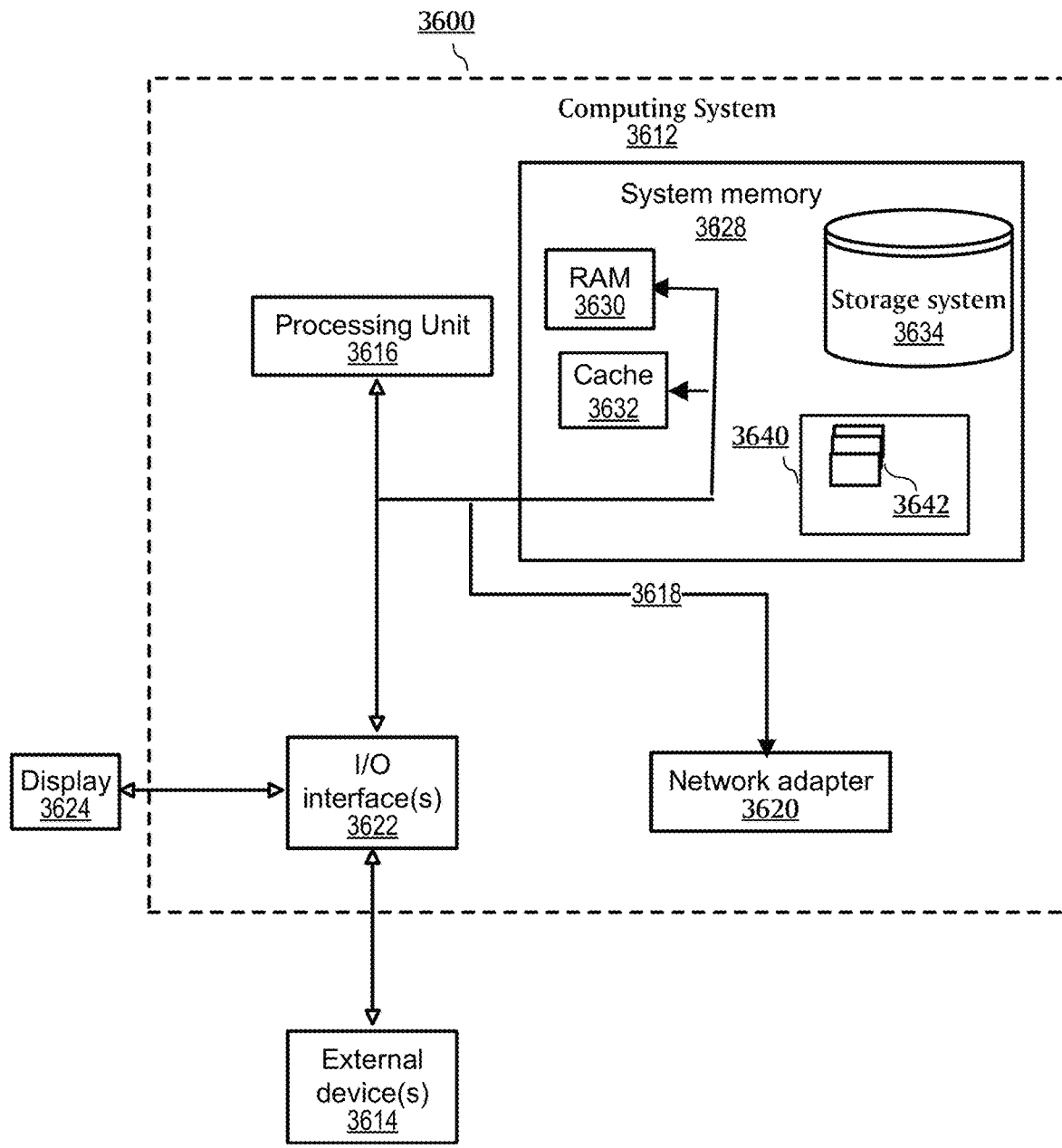

According to an embodiment of the present invention, there is a method for activating Cell-mediated Herd Immunity™[1] (CMHI) in a group of people to mitigate a risk of pandemic mass spread. Inducing at least one of four separate pathways to activate CMHI in the group of people by restoring a normal absolute number and function of natural killer (NK) cells and where the four separate pathways include: absolute humidity CMHI, vitamin D CMHI, gut microbiome CMHI, and antiviral priming CMHI in the group of people. The absolute humidity CMHI is activated by ensuring air inside an enclosed space where at least two people in the group of people are present has a target minimum absolute humidity value in the group of people inducing a simultaneous optimization of mucosal immunity for the at least two people. The vitamin D CMHI is activated by utilizing a vitamin D mass testing, mass treatment, and mass maintenance protocol for a first majority of people in the group of people to elevate the first majority of people into an upper end of normal range of serum vitamin D thereby stimulating macrophages and NK cells in the first majority of people. The gut microbiome CMHI is activated by ingesting a prebiotic, probiotic, non-pharmaceutical phytochemicals and micronutrients by a second majority of people in the group of people and thereby stimulating NK cells in the second majority of people. The antiviral priming CMHI is activated by ingesting bioavailability enhanced non-pharmaceutical phytochemicals with intrinsic biomolecular properties that inhibit enzymes critical to viral replication for a period of time by a third majority of people in the group of people. The risk of pandemic mass spread is mitigated based on the activating of the at least one of four separate pathways.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention will be apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein:

FIG. 1 depicts the steps taken by a process that activates Cell-mediated Herd Immunity (CMHI) in a group of people;

FIG. 2 shows the steps taken by an absolute humidity safety process;

[1]Cell-mediated Herd Immunity is a trademark of Jeff Gusky.

FIG. 3 shows the steps taken by a process that activates cell-mediated immunity (CMI) on mucosal surfaces in a respiratory tract of an individual;

FIG. 4 shows the steps taken by a process that indicates viral safety of enclosed spaces;

FIG. 5 shows actions taken when viral safety is not safe;

FIG. 6 depicts a schematic view of an indoor safety apparatus;

FIG. 7 shows the steps taken by an indoor safety indication process;

FIG. 8 depicts a schematic view of a computer network cloud environment;

FIG. 9 depicts a schematic view of a HIPAA compliant interactive communication system overview;

FIG. 10 depicts a schematic diagram of a system having support for a sensor directory;

FIG. 11 depicts a list of example sensor APIs;

FIG. 12 depicts an embodiment enabling an unsafe indication on a mobile device;

FIG. 13 shows the steps taken to achieve a serum vitamin D level as measured by blood;

FIG. 14 shows the steps taken to achieve a viral safe range of serum vitamin D level in a group of people;

FIG. 15 shows the steps taken by a process that facilitates activation of gut microbiome CMHI in a group of people;

FIG. 16 shows the steps for restoring and maintaining a healthful gut microbiome;

FIG. 17 shows the steps for facilitating activation of antiviral priming induced Cell-mediated Herd Immunity (CMHI) for long term usage;

FIG. 18 shows the steps taken for antiviral priming for a group of people;

FIG. 19 shows the steps taken to assess spike protein induced thromboembolism risk in an individual;

FIG. 20 shows the steps taken to facilitate activation of antiviral priming induced Cell-mediated Herd Immunity (CMHI) for short term usage;

FIG. 21 shows the steps taken for immediate treatment of a person with initial viral symptoms by rapidly activating individual cell-mediated immunity (CMI);

FIG. 22 shows the steps for using a viral prevention packs;

FIG. 23 shows the steps to assess and mitigate risk of spike protein induced immune suppression and endothelial inflammation;

FIG. 24 shows the steps taken by a company-specific viral safety certification program;

FIG. 25 shows the steps taken by a process that recruits, credentials, onboards, and trains qualified service providers supporting CMHI for community health;

FIG. 26 shows the steps taken to reducing company insurance premiums;

FIG. 27 depicts a high-level schematic representation of an intelligent system designed for facilitating contextually relevant conversational interactions;

FIG. 28 depicts a high-level block diagram representation of an AI system;

FIG. 29 depicts an embodiment of an Artificial Intelligence (AI) system trained to support bulk testing;

FIG. 30 shows steps taken by a user registration process;

FIG. 31 depicts a representation of a user profile data which may include user identification and demography;

FIG. 32 depicts a high level representation of user specific data;

FIG. 33 depicts a schematic view of an Artificial Intelligence (AI) event scheduling prediction model;

FIG. 34 shows the steps for dynamically facilitating Cell-mediated Herd Immunity (CMHI);

FIG. 35 depicts an embodiment of CMHI artificial intelligence (AI) event prediction model; and FIG. 36 depicts a schematic view of a processing system wherein the methods of this invention may be implemented.

DETAILED DESCRIPTION

Prior to 2019, the United States experienced an unprecedented decline in mortality during the twentieth century, thanks to improvements in public health, medical advances, and behavioral changes. Actuarial data reflecting US excess mortality, disability and workplace absenteeism was stable from year-to-year over many years.

There was a moderate rise in these data in 2020 correlated with the Covid-19 pandemic, hereafter referenced as Covid. In 2021, US actuarial data from the Centers for Disease Control and Prevention (CDC), the US Bureau of Labor Statistics, and the Society of Actuaries reflecting US excess mortality, disability and workplace absenteeism began rising dramatically. Statistical norms were broken. The rises continued and accelerated in the second quarter of 2023, especially in employee disability and absenteeism. The cohort most affected are healthy, working aged Americans. Unprecedented rises in the incidence of heart attacks, strokes, blood clots, a variety of dangerous infections, autoimmune diseases, neurologic injuries and mysterious sudden deaths are now accelerating as never seen before. Women in the workforce have been disproportionately affected. This information is documented in a paper written by research firm Phinance Technologies, founded and operated by a former Blackrock portfolio manager Ed Dowd, Yuri Nunes (PhD Physics, MSc Mathematics) and Carlos Alegria (PhD Physics, Finance). The paper was published on Sep. 20, 2022 with the title "On measuring excess deaths" pertaining to the Covid pandemic and policy interventions. The excess mortality data was derived from Society of Actuaries, the CDC, and the World Health Organization (WHO) via different statistical methods. Second quarter 2023 real time disability data from The Bureau of Labor Statistics (BLS) rose 857k in June 2023 to a new all-time high of 34.15 million. The rate of change is accelerating again. Disability among employed people hit new highs as well.

The increase in deaths has caused a corresponding crisis in risk forecasting affecting large, publicly traded insurance companies. These companies have been losing billions of dollars due to the overwhelming numbers of unexpected insurance claims. The actuarial data on which the insurance industry has relied to forecast future insurance claims has become unpredictable. The industry has responded to this uncertainty by rapidly increasing insurance rates to offset their losses. This has placed extraordinary financial burdens on businesses and municipalities.

While Covid was responsible for the rise in excess mortality seen in 2020, the accelerating trends in excess mortality, disability and workplace absenteeism which occurred since the latter half of 2021 through the present are not attributable to Covid. This rapid acceleration of unexplained excess mortality, disability and worktime lost occurred in working aged adults, aged 15-64, and especially women, abruptly rising in the fall of 2021. The BLS statistical data and St. Louis Federal Reserve portrays never before seen rises in disability and workforce absenteeism affecting an estimated 10% to 30% of the American workforce. A graph identified by LNU00074597 of the data for Population—With a Disability, 16 Years and over may be viewed from Federal Reserve Economic Data (FRED) depicting the increase. Various sources may be found identifying the increase in death rate in the US and other countries as in the Group Life COVID-19 Mortality Survey Report dated August 2022 from SOA Research Institute.

The increases in disability, workforce absenteeism, and death are most likely related to widespread impairment of the immune system. This in turn has caused a complex array of secondary problems like cancer, heart disease, strokes, autoimmune diseases, a spike in many types of infectious diseases and more. When looking at the normalized (Z-Score) deviation from 2002 to 2019 trend in lost worktime rates ranged between −2 to +2 from 2002 to 2019. The Z-Score represents standard deviations to a mean in a group of scores. For the total full time workers: In 2020 and 2021 the Z-Score was around 7.5. In 2022 the Z-Score was about 13. The lost worktime rates have been growing increasingly out of line relative to the 2002-2019 behavior. This means that the deviation from trend in lost worktime rates in 2022 corresponded to more than 11 standard deviations (assuming a Gaussian distribution for the deviations) from trend in lost worktime rates over the 2002-2019 period. This is an extraordinarily strong signal. In relative terms, the deviation from trend in 2022 for the total (men+woman) full time workers was about 40%. Even though the absolute deviation from trend was greater in women (1.1%) than Men (0.9%), in relative terms the opposite was true, due to women's baseline absence rates being roughly double those of men. The normalized deviation from trend in lost worktime rates, rose above 13 by 2022. There is a similar deviation from trend in malignant neoplasms. Cancers and lymphomas have risen to a 9+ sigma (+4.996) level since Morbidity and Mortality Weekly Report (MMWR) week 14 2021. Both the MMWR weekly and Wide-ranging Online Data for Epidemiologic Research (Wonder) monthly data sets agree on a 4.9% current excess death rate. This condition did not exist during the 2020 Covid pandemic period.

Although, many now think the danger from Covid has passed because the numbers of deaths and hospitalizations are temporarily down. The accelerating trend related to absenteeism in the American workforce is not generally realized. There are an estimated 26 million American workers who are now chronically ill. This is skewed toward the working aged adults and in particular women.

In this disclosure, evidence is provided that the increase in deaths and increase in chronic sickness is rooted in a widespread impairment of a branch of people's immune system called innate immunity, or nonspecific immunity with which an individual has at birth. This innate immunity is an immune response that does not involve antibodies but rather involves the activation of macrophages, a type of white blood cell that surrounds and kills microorganisms, removes dead cells, and stimulates the action of other immune system cells and natural killer cells (NK). NK cells are a type of immune cell that has granules (small particles) with enzymes that can kill tumor cells or cells infected with a virus. An NK cell is a type of white blood cell. The NK cell produces antigen-specific cytotoxic T-lymphocytes, and the releases various cytokines in response to an antigen and is referenced hereafter as cell-mediated immunity (CMI). CMI constitutes the human immune system's first line of defense against all pathogens and plays a life-sparing role in controlling rapidly mutating airborne viruses. The complexity of CMI goes far beyond the scope of this disclosure. CMI has long been suppressed in most Americans as well as various locations throughout the world. This widespread suppression of CMI before Covid struck is what made the Covid pandemic possible. Information related to approaches to restore CMI in individuals has been available in the scientific literature for years but has been largely ignored. CMI is the only reliable immune defense against rapidly mutating airborne viruses such as the common cold, influenza, respiratory syncytial virus (RSV), and Covid.

Many references and studies document the problems disclosed herein. There are also many articles that include data supporting the effectiveness of the approaches disclosed herein to overcome the problems. In order to make it easy to find the references, identification of many of the references specify an identification PMCID of a version of the article in PubMed®[2] Central (PMC) which is a free full-text archive of biomedical and life sciences journal literature at the U.S. National Institutes of Health's National Library of Medicine. An individual reference may be identified by PMC<number>, a PMCID, or both.

Numerous peer-reviewed studies show that CMI is activated or deactivated by: 1) The levels of absolute humidity levels in inhaled air. 2) Serum vitamin D levels. 3) The quality and quantity of healthy bacteria that comprise the gut microbiome. Deficiencies in each of these areas impair CMI which in turn directly increases the risk of hospitalization and/or death in individuals infected by Covid.

The article, "Seasonality of Respiratory Viral Infections," PMID: 32196426 written by Yale scientists discuss switching on mucosal CMI, which lowers human vulnerability and is not related to affecting the virus itself.

The article, "Interaction between microbiota and immunity in health and disease," PMID: 32433595, PMCID: PMC7264227, introduces the Gut microbiome and discusses aspects of the current knowledge, challenges, and limitations in achieving causal understanding of host immune-microbiome interactions, as well as their impact on immune-mediated diseases. The article also discusses how these insights may translate towards future development of microbiome-targeted therapeutic interventions.

CMI is the only branch of the immune system capable of blocking the mass spread of Covid and other rapidly mutating respiratory viruses. CMI is the only branch of the human immune system capable of neutralizing (i.e., killing) all Covid variants on contact.

CMI has been suppressed in most Americans for years. When the immune suppression of CMI is reversed, the risks of cancer, diabetes, heart attacks, strokes, autoimmune disease, and a wide array of infections are dramatically reduced.

[2]PUBMED is a trademark of the National Library of Medicine.

Since 2021, the impairment of CMI has become more severe. Mass vaccination campaigns have caused permanent immune injury to the CMI of tens of millions of Americans due to a well-known complication of experimental vaccines called imprinting. When a vaccinated person afflicted with imprinting is exposed to a new Covid variant, they often produce antibodies against the spike protein from the original Wuhan variant instead of to the newly exposed Covid variant.

The article, "SARS-COV-2 Spike Protein Vaccine-Induced Immune Imprinting Reduces Nucleocapsid Protein Antibody Response in SARS-COV-2 Infection," PMID: 35935586, PMCID: PMC9355782, discusses: immune imprinting or original antigenic sin (OAS) which is the process by which the humoral memory response to an antigen can inhibit the response to new epitopes of that antigen originating from a second encounter with the pathogen. The immune dysfunction caused by imprinting is a separate problem from the widespread immune suppression of CMI that existed long before Covid.

The article, "Alarming antibody evasion properties of rising SARS-COV-2 BQ and XBB subvariants," PMID: 36580913, PMCID: PMC9747694 discuss the imprinting problem and states: Omicron are now rapidly expanding, possibly due to altered antibody evasion properties deriving from their additional spike mutations. Vaccinal antibodies have no ability to kill Omicron or stop mass spread.

The article, "Circulating Spike Protein Detected in Post-COVID-19 mRNA Vaccine Myocarditis," PMID: 36597886, PMCID: PMC10010667 discusses immunoprofiling of vaccinated adolescents and young adults revealed that the mRNA vaccine-induced immune responses did not differ between individuals who developed myocarditis and individuals who did not. However, free spike antigen was detected in the blood of adolescents and young adults who developed post-mRNA vaccine myocarditis, advancing insight into its potential underlying cause.

Well over ½ the American people now have CMI that is both injured and suppressed at the same time. This estimate is derived from the statistic that at least 81% of the American people received at least one Covid vaccination. Based on the assumption that at least 2 out of 3 of those who received the vaccination received doses that were not "duds" which suggests that ⅔ of the 81% of vaccinated Americans have sustained some degree of imprinting. This amounts to over 180 million Americans.

The immune impairment caused by imprinting is permanent. It cannot be undone. People with imprinting may be highly vulnerable to lethal Covid variants which are now on the horizon as well as to new gain-of-function engineered pathogens.

For hundreds of thousands of years human beings were protected against coronavirus infections by an impenetrable biological barrier located deep in the lungs. The modifications found in the Covid spike protein have permanently nullified the age-old protections against potentially lethal coronavirus infections. The spike proteins may also cross the blood brain barrier and attack brain cells.

The article, "A call for an independent inquiry into the origin of the SARS-COV-2 virus, "PMID: 35588448, PMCID: PMC9173817" leaves open the question as to whether or not the COVID-19 virus was from human exposure to an infected animal ["zoonosis" (2)] or that it emerged in a research-related incident.

Regardless of the answer to the question as to whether Covid modifications were via gain-of-function methods, modifications in the Covid spike protein were not previously found in nature and they now may allow deep lung penetration. One example is the furin cleavage site which allows the spike protein to cleave away from the virus and float freely in the bloodstream reaching every organ in the body including the brain. Furin is a protease, a proteolytic enzyme that in humans and other animals is encoded by the Furin gene. Some proteins are inactive when they are first synthesized and must have sections removed in order to become active. Furin cleaves these sections and activates the proteins.

Nearly every living American, vaccinated or not, has now been inoculated with the spike protein which can penetrate into the deep lungs and reach other parts of the body. The spike protein can function like an offensive weapon, attacking the endothelial cells which line the lumen of every blood vessel in the body. The endothelium is collectively the largest organ in the body.

The article, "SARS-COV-2 Spike 1 Protein Controls Natural Killer Cell Activation via the HLA-E/NKG2A Pathway, PMID: 32859121, PMCID: PMC7563485, discusses information related to how Spike Proteins Impair Natural Killer Cells.

It is impossible to feel injuries to the brain or endothelium caused by the spike proteins while they are taking place. This is because the cells comprising the endothelium and the brain lack nerve endings to signal injury while it is taking place.

The absence of nerve endings in the endothelium is why atherosclerotic cardiovascular disease is a silent killer. Atherosclerosis causes painless injuries to the endothelium. Without nerve endings to the endothelium, people have no idea that their bodies are under attack until it is too late. Like atherosclerosis, tens of millions of people are now experiencing painless but irreversible spike protein injuries to their brains and vital organs. They have no idea that these devastating injuries are taking place.

Compounding the inability to feel spike protein injuries while they are taking place is the inability to fight new Covid infections now afflicting many of those who have been vaccinated. The well-known vaccine complication called imprinting can silently disable the ability of many vaccinated people to mount an immune defense against new Covid variants. When a vaccinated person afflicted with imprinting is exposed to a new, potentially lethal Covid variant, they often produce antibodies against the spike protein from the original Wuhan variant. Their ability to produce antibodies tailored to the new variant is all but paralyzed. Imprinting impairs the natural ability to tailor new antibodies to new variants.

Suppressed CMI and/or injured CMI caused by imprinting represent a national security threat which Americans have never seen before. Potentially lethal Covid mutations are now surfacing at an alarming rate based on the CDC's biweekly Covid data tracker. Omicron has become the most infectious virus the world has ever seen.

Moreover, vaccinal antibodies are incapable of neutralizing Omicron. Without CMI, Americans will be unable to defend themselves against dangerous new Covid variants or new bioweapons. Impaired CMI will result in death rates that could eliminate large segments of the American population.

Imprinting has now permanently reprogramed the immune systems of tens of millions of vaccinated people not to work. The immune systems of most vaccinated people are no longer capable of killing the virus with antibodies. The fact that the rates of hospitalizations and deaths have declined since the arrival of Omicron is not because antibodies are killing the virus but due to a temporary blockade of deep lung infections. If and when this temporary blockade ends, hospitalizations and deaths in vaccinated people of all ages are likely to skyrocket.

The article, "Determinants and Mechanisms of the Low Fusogenicity and High Dependence on Endosomal Entry of Omicron Subvariants," PMID: 36625591, PMCID: PMC9972997 discusses mechanisms underlying the distinct entry pathway of Omicron subvariants, which have temporarily diminished deep lung infections.

Another national security threat exists which could suddenly and without warning cause mass death and/or mass disability in vaccinated people. The threat is related to two factors: (1) One is called pseudo herd Immunity. This has encouraged the widespread belief that the pandemic is over because of the decline in Covid hospitalizations and deaths. This decline is not because the immune systems of vaccinated people are killing the virus and clearing it from their bodies. On the contrary, mass vaccination campaigns have transformed Omicron into the most contagious virus in history.

In July of 2023, Omicron continues to circulate widely and mutate rapidly. While the contagiousness of Omicron has increased exponentially, the vaccines have induced a paradoxical phenomenon which has never been seen before: a temporary blockade of deep lung infections. Deaths and hospitalizations caused by Covid exclusively originate in the deep lungs. The current blockade of deep lung infections has led to the substantial decline in hospitalizations and deaths, creating the illusion that the pandemic is over. Because vaccinal antibodies are not killing the virus but merely blocking the virus from infecting deep lung cells, the virus continues to rapidly mutate. This raises the mathematical odds that an escape mutation could develop at any time which would circumvent the temporary blockade of deep lung infections. Once this happens, Omicron will resume infecting the deep lungs. Contrary to popular opinion, Omicron is extremely dangerous and often deadly when it infects the deep lungs.

Evidence regarding Omicron variants is available in the article, "Global threat from novel SARS-COV-2 variants, BF.7, XBB.1.5, BQ.1, and BQ.1.1: variants of concern?", PMC10063927. The reproduction number of the recent BF.7 is 10 to 15. This translates to a doubling time of hours, not days. Prior to Covid, measles was considered to be the most infectious virus with a reproduction number of 8.

People who have been vaccinated face extraordinary risks when the temporary blockade of deep lung infections ends. Imprinting represents the biological equivalent of a "kill switch" which has been hard wired into the immune systems of many vaccinated people. Fortunately, for some vaccinated people imprinting is mild but for others it is severe. When and if the temporary blockade of deep lung infections that causes pseudo herd immunity is bypassed, tens of millions of vaccinated people will be incapable of protecting themselves against a deadly threat due to imprinting. The possibility of mass death and long term disability among many survivors is real. The health care system would collapse. The American military, most of whom are vaccinated, could be decimated.

Many peer-reviewed scientific papers demonstrate that immunity against respiratory viruses is related to: 1) Breathing indoor air with safe levels of absolute humidity, 2) Maintaining serum vitamin D levels in the upper end of the normal range, and 3) Maintaining a healthful gut microbiome. What each of these three seemingly disparate factors has in common is that they each play a critical role in activating CMI and making it work properly. When CMI does not work properly, an individual is said to have impaired CMI.

The article "Indirect health effects of relative humidity in indoor environments," PMID: 3709462, PMCID: PMC1474709, state: Experimental studies on airborne-transmitted infectious bacteria and viruses have shown that the survival or infectivity of these organisms is minimized by exposure to humidity levels between 40 and 70%. This is also supported by data from American Society of Heating, Refrigeration and Air-Conditioning Engineers (ASHRAE) that shows indoor humidity levels can mitigate the spread of airborne diseases of all kinds. Regarding indoor humidity levels, for decades, ASHRAE has promulgated global standards for indoor humidity levels. ASHRAE has long emphasized the special importance of indoor humidity in senior care settings and schools, but their guidance has been largely ignored. The article, "Absolute humidity modulates influenza survival, transmission, and seasonality," found in The Proceedings of the National Academy of Sciences (PNAS), a peer reviewed journal of the National Academy of Sciences (NAS) Vol. 106 | No. 9 warns that "These findings also suggest that humidification of indoor air, particularly in places where transmission to those at high risk for complications, such as nursing homes and emergency rooms, may help decrease the spread and the toll of influenza during influenza season." When Covid struck, buildings with heating, ventilation, and air conditioning (HVAC) systems designed in compliance with longstanding ASHRAE guidelines on indoor humidity experienced remarkable protection against the mass spread of Covid. In particular, Japan and South Korea took ASHRAE guidelines seriously after experiencing severe acute respiratory syndrome (SARS), a viral respiratory disease caused by a SARS-associated coronavirus in 2002 and 2003. Since the beginning of the pandemic, Japan and South Korea have maintained the lowest rates of Covid deaths of all industrialized nations in the world. Dallas Fort Worth (DFW) airport, Love Field Airport, Dallas's NorthPark Mall and the 1,300 bed Collin County Adult Detention Center are public places with HVAC systems that often conform to ASHRAE guidelines. The Collin County Adult Detention Center has reported only 1 inmate with Covid since the start of the pandemic.

Additional support can be found in a white paper, "USING HUMIDIFICATION TO REDUCE THE TRANSMISSION OF VIRUSES" published by DRISTEAM.

Nations with tropical ambient humidity have fared much better than nations with temperate climates with lower humidity. Utilizing data collected by Worldometer in July 2023, representation of Covid deaths per million since the start of the pandemic include: Burundi . . . 3, Chad . . . 11, Tanzania . . . 13, Benin . . . 13, Nigeria . . . 15, Democratic Republic of Congo . . . 15, Burkina Fosso . . . 18, Central African Republic 23, United States . . . 3,490. Summary of African Countries Above . . . With a combined population of 471 million they experienced 16 deaths per million. By comparison, the United States with a population of 335 million people experienced 3,490 deaths per million.

The only environmental metric that is well correlated with the risk of respiratory viral pandemics is an obscure environmental measurement called absolute humidity which measures the weight of water in a given volume of air. Relative humidity (RH) is a measure of the capacity of air to hold water. Absolute humidity (expressed as grams of water vapor per cubic meter volume of air) is a measure of the actual amount of water vapor (moisture) in the air, regardless of the air's temperature. Absolute humidity is quite different from relative humidity.

In addition to information related to relative humidity, numerous studies show correction of vitamin D deficiencies or reaching a high range of vitamin D targets have widespread health benefits. The data includes reducing fall risk by at least 49%. "The results of the study indicate that vitamin D and calcium supplementation reduced the number of falls per person by 49% within 3 months of treatment in elderly women with vitamin D deficiency." Reduce respiratory viral infections by at least 40%: "After studying these patients for a year, a 40 percent reduction in acute respiratory illness was found among those who took higher doses of vitamin D. Also avoiding vitamin D deficiencies translates into increased patient life spans: "Although vitamin D deficiency among frail and elderly populations has been acknowledged for several decades, no effective strategies to treat the deficiencies have been developed and implemented." Also ensuring adequate levels of vitamin D translated into dementia risk being decreased by 40%: "A study in a cohort of 12,388 persons showed that vitamin D exposure over 10 years could lower the risk of dementia by 40 percent; women in the study experienced a greater benefit than men."

The article, "Low Vitamin D and Its Association with Cognitive Impairment and Dementia, PMCID: PMC7210535, PMID: 32399297 provides background information and data.

CMI is the body's critical first line of defense against all respiratory pathogens. CMHI occurs when enough individuals inside the same indoor space have personal CMI that is intentionally activated or switched on. In an embodiment, personal CMI implies one or more activation of vitamin D CMI, antiviral priming CMI and gut microbiome CMI. Population-based Immune Rescue™[3] is designed to restore damaged and/or suppressed immune systems even in vaccinated people who have sustained permanent

[3]Population-based Immune Rescue is a trademark of Jeff Gusky.

immune system injury due to imprinting. Embodiments of the present invention relates to the induction of population based immune defenses against respiratory pathogens and to mitigating the risk of viral pandemics caused by the current widespread immune suppression of CMI. More particularly, embodiments of the invention are about realizing synergies of viral protection by optimizing multiple forms of CMI simultaneously.

CMHI is a form of herd immunity that does not rely on antibody (i.e., adaptive) immunity. CMHI is about protective synergies that happen when some or ideally all of the four key determinants of CMI are optimized at the same time within a large population of people. The four factors that activate or "switch on" CMHI are: (1) Safe levels of indoor absolute humidity (2) Vitamin D In upper end of normal range (3) Healthy gut microbiome (4) Antiviral priming.

CMHI is the only way to proactively defend entire cities against respiratory viral pandemics. CMHI's role in stopping respiratory viral pandemics only matters indoors because pandemic mass spread of dangerous respiratory viruses only occurs indoors. CMHI happens when enough people inside an indoor space (like a building, a bus or a subway) have the four types of individual CMI switched on.

Three of the four individual types of CMI should be activated before people enter an indoor space in order for CMHI to become manifest. These are: 1) Vitamin D CMI, 2) Gut microbiome CMI, and 3) Antiviral priming CMI. The fourth individual type of CMI is activated automatically when a person breathes indoor air which has safe levels of absolute humidity. In the case of absolute humidity CMI, it does not matter whether a person's absolute humidity CMI is switched on or not before that person enters a given building. This is because their absolute humidity CMI is automatically activated soon after that person enters an indoor space which has safe levels of absolute humidity. Safe indoor absolute humidity is effectively a non-pharmaceutical antiviral agent.

The article, "Humidity as a non-pharmaceutical intervention for influenza A," PMID: 30252890 PMCID: PMC6155525, identified humidity as a non-pharmaceutical antiviral. Because everyone occupying the same building at the same time is breathing the same indoor air, they are breathing the equivalent of an antiviral medication, all at the same time. Merely the act of breathing indoor air with safe absolute humidity switches on individual absolute humidity CMI in everyone. Because everyone in the building has individual absolute humidity CMI that is activated at the same time, absolute humidity CMHI becomes activated automatically.

The most powerful CMHI happens when most if not all people in a particular indoor space have all four types of individual CMI switched on at the same time. This requires that vitamin D CMI, gut microbiome CMI and antiviral priming CMI are activated before people enter the indoor space. But since absolute humidity CMI is automatically switched on soon after a person enters an indoor space which has safe indoor absolute humidity, CMHI is the only form of herd immunity that can make indoor public spaces safe again (i.e., buildings, buses, cars and trains).

Population-based Immune Rescue is expected to have the following characteristics: (1) Taps a hidden immune reserve capacity. (2) Can help tens of millions of Americans with permanently damaged immune systems to optimize what is left of their remaining immune capacity. (3) Rapidly transform the collective CMI of entire cities and workforces from being dangerously impaired to viral safe. (4) Critical to national defense since well over half the American population now have some degree of immune impairment due to imprinting caused by the newly introduced Covid vaccines that uses a molecule called messenger ribonucleic acid RNA (mRNA) rather than part of an actual bacteria or virus. CMHI mitigates this unprecedented state of population-wide vulnerability. (5) Proactively defend cities and workforces against lethal Covid variants and future potential gain-of-function pathogens. Population-based Immune Rescue performs these functions and it costs extraordinarily little!

Making American cities safe again requires CMHI. CMHI benefits everyone, especially vaccinated people with damaged immune systems. In an embodiment, risk management protocols begin with Population-based Immune Rescue which can rapidly shield cities and workforces against potentially massive losses of life. CMHI hardens workforces against the now rapidly accelerating rates of absenteeism and rapidly declining employee productivity due to immune damage. CMHI noticeably adds to bottom line profits beginning within weeks.

In an embodiment, Population-based Immune Rescue is provided by the approaches for CMHI described herein. The disclosed approaches are expected to be effective in providing herd immunity against Covid and other rapidly mutating respiratory viruses. The disclosed approaches are expected to be effective in stopping new pandemics and new respiratory potential gain-of-function pathogens that may be just around the corner. In an embodiment, approaches are disclosed to help cities and workforces achieve CMHI fast. Damaged immunity of entire populations is rescued, restored, or salvaged at once. The approach should increase: (1) Profits. (2) Workforce productivity especially in immune injured employees. (3) Confidence. Employees want to be at work because CMHI in the workplace makes being at work the safest part of their day. (4) Employee loyalty because employees see management's sincere efforts to make employees safer with innovative measures to help protect them and their families. (5) Employee retention. (6) Morale. CMHI requires individual employees to do their part to keep other employees safe (7) Competitiveness. Workforces with optimized CMHI produce more for less which provides businesses with CMHI a clear competitive advantage.

CMHI should decrease: (1) Operating Costs. (2) Absenteeism in workforces and schools. (3) Healthcare Costs. (4) Missed work when a child of an employee is home sick from school. (7) Recurrent Covid which is associated with premature death and permanent injury to vital organs. (8) Risk of chronic diseases. (9) Transmission of pathogens by vaccinated employees to their families.

The article, "Association of vitamin D status with COVID-19 and its severity," PMID: 34982377 PMCID: PMC8724612 discusses Vitamin D and its association with biological activities of the innate and adaptive immune systems, as well as inflammation. In observational studies, an inverse relationship has been found between serum 25-hydroxyvitamin D (25(OH)D) concentrations and the risk or severity of coronavirus disease 2019 (COVID-19). Evidence for Rapid Immune Rescue Achievable By Higher Levels Of Vitamin D.

The article, "Nutrients Systematic Review COVID-19 Mortality Risk Correlates Inversely with Vitamin D3 Status, and a Mortality Rate Close to Zero Could Theoretically Be Achieved at 50 ng/ml 25(OH)D3: Results of a Systematic Review and Meta-Analysis PMID: 34684596, PMCID: PMC8541492, provides evidence related to the effectiveness of the Vitamin D aspect of Population-based Immune Rescue.

The National Library of Medicine article PMC7210535 discusses low vitamin D and its association with cognitive impairment and dementia. The article goes on to state: "This body of evidence suggests that vitamin D may be a new paradigm for therapy in the prevention and treatment of dementia and Alzheimer's disease (AD)." Articles and studies link elevated levels of vitamin D with decreased Chronic Obstructive Pulmonary Disease (COPD) risk, severity and exacerbations, lower risk of bed sores, decreased diabetic foot infection, decreased urinary tract infections, decreased risk of fungal infections, decreased incidence, severity and functional decline following shingles (herpes zoster). In elderly, elevated levels of vitamin D decreased chronic pain without narcotics. Elevated levels of vitamin D also led to decreased anxiety, depression, and agitation, improved sleep and quality of life, improved balance and equilibrium, and lower risk of hematuria in postmenopausal women.

Studies show that higher levels of vitamin D for employees increased productivity: "Employee vitamin D assessment and replenishment may represent a low-cost, high-return program to mitigate risk factors and health conditions that drive total employer health care costs." Also, higher levels of vitamin D for employees reduces accidents in the workplace plus improved wellness, sleep and mental health especially in shift workers reduced headache, reduced premenstrual syndrome (PMS), reduced fatigue, reduced rates of common cold, reduced rates of influenza, reduced heartburn and stomach ulcers. In addition, higher levels of vitamin D leads to overall disease prevention, such as, preventing Covid, and cancer. Over 3,000 studies link low vitamin D to cancer, hundreds of thousands of cancer deaths can be prevented each year. Higher levels of vitamin D, helps to stop many different cancers including lung, colon, brain, breast, melanoma, pancreatic, kidney, bladder, and prostate. Low vitamin D levels are associated with heart attacks, strokes, blood clots, pulmonary emboli, suicide, Parkinson, Alzheimer's, autoimmune diseases, respiratory infections, tuberculosis, fungal infections, death, diabetes, multiple sclerosis, liver disease, chronic pain, and obesity.

In addition to humidity ranges and vitamin D levels, evidence also exists for lack of immunity related to an unhealthful gut microbiome. People who are hospitalized or die from Influenza often have an unhealthy gut microbiome. An unhealthy gut microbiome is associated with bacterial, viral, fungal infections, infectious diarrhea in healthcare facilities, and the risk of *Clostridium difficile* infections.

The article, "Interaction between microbiota and immunity in health and disease," PMID: 32433595, PMCID: PMC7264227, discusses Gut Microbiome & Immunity. The paper discusses "under the influence of certain environmental factors and host genetic susceptibility, aberrant interactions between the microbiome and the host's immune system contribute to the development of various immune-mediated disorders."

The article, "Quercetin: A Functional Food-Flavonoid Incredibly Attenuates Emerging and Re-Emerging Viral Infections through Immunomodulatory Actions," PMID: 36770606. PMCID: PMC9920550, discusses Food Supplements As Viral Replication Blockers.

The article, "Plant-derived compounds effectively inhibit the main protease of SARS-COV-2: An in silico approach," PMID: 35998194, PMCID: PMC9398018, provides support for the effectiveness of an embodiment of Rapid Immune Rescue.

An approach is disclosed for a population based risk reduction strategy. Companies and cities can limit their exposure to rising insurance premiums with new, industry-specific risk management protocols that can lower their insurance costs by achieving CMHI in enclosed public spaces. The disclosed protocols rapidly lower a company's risk profile, often to levels that are better than pre-pandemic levels. Risk-managed CMHI is the future of corporate risk management. With the disclosed unique, industry specific risk management protocols, companies can dramatically lower their risk profile, often to better than pre-pandemic levels. In an embodiment, company-specific actuarial data is aggregated to document the company's lower risk. With independently documented lower risk profiles, insurance brokers can negotiate lower insurance premiums for many types of business insurance.

Risk managed CMHI has the following characteristics: (1) Industry-specific risk management protocols lowers a company's risk profile starting almost immediately. (2) By lowering a company's risk profile, the company is expected to qualify for lower insurance rates compared to prevailing rates paid by other companies in their industry. (3) Company-specific actuarial data are tracked and analyzed to clearly establish the company's new risk profile. CMHI also includes special benefits to the senior care industry including: (1) Specialized workforce hardening increases workforce resilience against disease. (2) Client hardening which makes both inpatient clients (i.e., nursing homes) and outpatient clients (i.e., home health industry and adult day care centers) more resilient, less prone to hospitalization, death and injuries (3) Family hardening which makes employees' families less prone to illness and less likely to pass illness from the family to the employee which that employee may, in turn, bring to work and vice versa.

Risk mitigation of long term spike protein injuries: (1) Excess mortality, disability, absenteeism and lower workforce productivity. (2) Cancer. (3) Sudden Deaths. (4) Heart attacks and myocarditis. (5) Brain Injury. (6) Infertility. (7) Strokes. (8) Amyloidosis. (9) Thromboembolic disease (i.e., Clots).

In an embodiment, a new culture of viral safety in cities and workplaces promotes employee recruitment. Potential hires will be motivated to work for a company that makes being at work the safest part of their day. The approach includes safety measures employees can see with their own eyes and believe in. In an embodiment of the employee retention plan, support is supplied to (1) Assist employees in keeping their families safer. (2) Optional family testing and treatment as a benefit of employee loyalty. The employee morale is improved since viral safety unites employees around creating herd immunity in the workplace. Herd immunity in the workplace helps keep everyone safer. Family morale is increased when viral safety implemented in the workplace carries over into the home. Increased family safety decreases workforce absenteeism caused by parents missing work because of a child home sick from school.

Absolute humidity is difficult to measure. At the time of the original submission of this disclosure, there is no device that can be purchased on Amazon to measure absolute humidity. Many studies have shown that regions with ambient absolute humidity of 10 grams/m$^3$ and above have experienced much lower rates of Covid.

The article, "Seasonality of Respiratory Viral Infections," PMID: 32196426, refer to section 5.2, that provides evidence that CMI is inducible, that is, may be switched on.

The article, "Investigating the effects of absolute humidity and movement on COVID-19 seasonality in the United States," PMID: 36202875, PMCID: PMC9537426, helped guide the executive team at Houston's Methodist Healthcare System in the early days of Covid.

The article, "Impact of meteorological factors on the COVID-19 transmission: A multi-city study in China," PMID: 32304942, PMCID: PMC7194892, discusses Absolute Humidity and Mass Spread of Covid, with a graph showing that about 90% of the viral contagion is at an absolute humidity under 8 gm/m$^3$.

Currently, millions of dollars are spent on health care costs, insurance, lost productivity and the like that could be reclaimed by reducing daily operating costs, liability, and reduced hospitalizations, accidents and infections. The disclosed approach increases patient and family satisfaction for residents and promotes increased productivity for employees. "Employee vitamin D assessment and replenishment may represent a low-cost, high-return program to mitigate risk factors and health conditions that drive total employer health care costs." Reduced accidents in the workplace plus improved wellness, sleep and mental health especially in shift workers, reduced headaches, reduced PMS, reduced fatigue, reduced rates of common cold, reduced rates of influenza, reduced heartburn and stomach ulcers.

Recurrent Covid is dangerous. Covid is not "the flu." Each time a person is reinfected by Covid, their lifespan may be shortened. Covid reinfection also may cause hidden brain damage and injury to vital organs that occurs slowly and remains invisible until the damage is significant and irreversible.

Covid will never go away. It has now spread to numerous wild animal species. These species have become reservoirs for the virus.

Those who die from Covid actually die from something else. That something else is called cytokine storm. It is a two-step process. In the first step, Covid triggers cytokine storm. In the second step, Cytokine storm triggers severe illness, hospitalizations, and deaths. Nearly all severe illness, hospitalizations and deaths can be prevented by blocking cytokine storm. However, there is only a brief interval of time when blocking cytokine storm is even possible. The interval begins the moment that viral-like symptoms first appear. This is when the clock starts ticking. Treatment must begin without delay. Disclosed herein is a safe, affordable, non-pharmaceutical solution which makes blocking cytokine storm at the local level extremely easy to do identified herein as the Viral Fire Extinguisher®[4]. Everyone knows that the best time to put out a fire is right away. Extinguishing a fire immediately is the only way to prevent a small fire from becoming a raging inferno. It is why in public buildings; fire extinguishers are everywhere. Although, hopefully, not needed, when needed, a fire extinguisher must be rapidly available and ready for immediate use. Similar to fire extinguishers, to prevent catastrophic loss of life, the "Viral Fire" must be extinguished as soon as possible especially in vaccinated people with the "kill switch," Viral Fire Extinguishers must be readily available at the local level when viral-like symptoms first appear. Immediate treatment is the only way to block cytokine storm and the only way to prevent the "kill switch" from being triggered in vaccinated people who become ill with a potentially lethal variant of Covid.

Society-wide prevention of cytokine storm and imprinting is imperative if highly vaccinated societies are to survive. The only way to prevent cytokine storm and imprinting in entire populations at once is herd immunity. The only herd immunity possible against Covid is CMHI. The actual cause of death in most people who die from Covid, Avian Flu, Influenza or Middle East respiratory syndrome (MERS) is cytokine storm. The vaccine complication called imprinting all but paralyzes the ability of many vaccinated people to mount an immune defense against Covid infections in the deep lungs. Imprinting has elevated the risk of mass death in vaccinated people.

As discussed in the National Library of Medicine article PMCID: PMC8876409 and PMID: 35208467, cytokine storm is a severe immune reaction in which the body releases too many cytokines into the blood too quickly. Cytokines play a key role in normal immune responses but having a large amount of them released in the body all at once can be harmful. A cytokine storm can occur as a result of an infection, autoimmune condition, or other disease. It may also occur after treatment with some types of immunotherapy. Signs and symptoms may include high fever, inflammation (redness and swelling), and severe fatigue and nausea. Sometimes, a cytokine storm

[4]Viral Fire Extinguisher is a registered trademark of Jeff Gusky.

may be severe or life threatening and lead to multiple organ failure. Moreover, cytokine storm has recently emerged as a key aspect in the novel Coronavirus disease 2019, as affected patients show high levels of several key pro-inflammatory cytokines, such as IL-1, IL-2, IL-6, TNF-α, IFN-γ, IP-10, GM-CSF, MCP-1, and IL-10, some of which also correlate with disease severity. With those who die from Covid, the actual cause of death is almost always cytokine storm. With those who are hospitalized because of Covid, the hospitalization is almost always caused by a degree of cytokine storm. The risk of cytokine storm is higher in those with low vitamin D and/or an unhealthy gut microbiome. The gut microbiome is critically important to mitigating the risks of: cytokine storm. A healthy gut microbiome can make the difference between who lives and who dies from Covid as well as who is hospitalized with Covid. This is because of the critical role played by the gut microbiome in helping to prevent cytokine storm. People who are hospitalized or who die from influenza often have an unhealthy gut microbiome. Bacterial, viral and fungal infections, infectious diarrhea, food poisoning, *Clostridium difficile* infections and many other hospital acquired infections are often correlated to an unhealthy gut microbiome.

The article, 'Influenza infection, SARS, MERS and COVID-19: Cytokine storm—The common denominator and the lessons to be learned," PMID: 33333256, PMCID: PMC7832378, discusses cytokine storm as cause of death and also provides evidence of potential value of Population-based Immune Rescue.

The article, "Perspective: Vitamin D deficiency and COVID-19 severity—plausibly linked by latitude, ethnicity, impacts on cytokines, ACE2 and thrombosis," PMID: 32613681, PMCID: PMC7361294 discusses increased risk of cytokine storm caused by: low vitamin D.

The article, "Cytokine Storm in COVID-19: Immunopathogenesis and Therapy," PMC8876409 with PMID: 35208467 provides an overview of information related to immune suppression and activation of "cytokine storm in COVID-19: Immunopathogenesis and Therapy."

The article, "Mechanisms by Which the Gut Microbiota Influences Cytokine Production and Modulates Host Inflammatory Responses," PMID: 31013453 discusses Unhealthy Gut Microbiome and influences on diseases.

The nations with the lowest rates of Covid deaths are in tropical climates where a substantial percentage of the population routinely take Ivermectin to prevent River Blindness and Elephantiasis and/or Hydroxychloroquine to prevent malaria. As a result, at any given time, a substantial percentage of the population in these nations have background levels of Ivermectin and Hydroxychloroquine in their bloodstreams. When Covid struck, these nations benefited from the fact that Ivermectin and Hydroxychloroquine each have potent antiviral properties. Similar antiviral benefits can be achieved with non-pharmaceutical food supplements which have proven antiviral properties. Many peer-reviewed scientific studies have demonstrated that select non-prescription nutritional supplements have proven antiviral properties. But the antiviral properties can only be realized if enough of the bioactive ingredients are absorbed into the bloodstream. When taken by mouth, bioavailability is quite limited since most of these nutritional supplements are excreted from the body without being adequately absorbed. Disclosed is a way to package a select mixture of non-pharmaceutical food supplements into an advanced nanotechnology delivery system that helps achieve adequate bioavailability when taken orally. With this approach, people around the world may be able to achieve similar benefits to people living in African countries where a substantial portion of the population have continuous background levels of antivirals circulating in their blood at all times. Their bloodstream is primed at all times with low levels but of bioactive molecules which have antiviral properties. This phenomenon is called "antiviral priming." Antiviral priming can be achieved safely and inexpensively using the right combination of non-prescription nutraceuticals delivered orally using a nanotechnology delivery system.

The article, "Nanoencapsulation of Polyphenols as Drugs and Supplements for Enhancing Therapeutic Profile—A Review," PMID: 34551693 discusses nanotechnology to increase bioavailability of nutraceuticals.

It is important to ensure the nutraceuticals are absorbed properly. Various nano technologies may be used. SMP Nutra is an example of a manufacturer that specializes in oral nutraceutical products delivered using advanced nanotechnology delivery systems.

In order to test some of the concepts disclosed herein, a one year investigation was conducted to gather data where there was an objective of bringing participants to a target level of vitamin D of 60 ng/ml treated at home by staff at Prestige Home Health in Starr county, Texas and also residents of nursing homes. Data on patients and staff was provided by Yolanda Garza registered nurse (RN)/Director of Nursing (DON) on Sep. 19, 2022. For patients that followed the disclosed protocol, zero tested positive for Covid as compared to fifty-three patients who tested positive for Covid who were not on the protocol. During the same one year period, four staff members on the disclosed protocol tested positive for Covid compared to 83 staff members who tested positive who were not on the disclosed protocol. Prestige Home Health also provided portable humidifiers in homes of many of the patients treated at home. Little or no sensors were provided to determine the level of humidification. Retama Manor also tried to make indoor humidify viral safe inside their facility by including humidifiers again without sensors. Though the capacity of their humidifiers was subpar, indoor humidity in all likelihood contributed to the facility's remarkable overall success. Only one patient at Retama Manor whose Vitamin D level was in the viral safe range tested positive during the 15 month study period.

Retama Manor nursing home in Rio Grande city, TX had the following results in patients and staff over approximately six quarters. Data was provided by Macario Villareal, RN/DON on Aug. 26, 2022.

Summary of results: Q1, Q2 and Q3 . . . zero Covid infections or deaths in patients or staff. During these three quarters, the Delta variant was spreading rapidly in the lower Rio Grande Valley. While infections surged in other nursing home facilities throughout the Rio Grande Valley, Retama Manor experienced no Covid in patients or staff. During Q4, Q5 and Q6 . . . a break in protocol by a staff member caused a brief cluster of cases. Outside of this breach of protocol, the number of Covid positive patients and staff remained near zero.

This underscores the importance of herd immunity in the workplace. A nurse's aide stopped taking her daily vitamin D. She initially failed to report this to her supervisor. She brought Covid into Retama Manor. Over the last week of Q4 and the first week of Q5, thirteen patients and about ten staff were infected. Aside from the break in protocol, there were 2 Covid positive patients in 9 months. Dr. Ray Mussett was the facility medical director at Retama Manor Nursing Home throughout the 15 month study period. The disclosed vitamin D protocol was followed by all nursing home employees and Dr. Mussett's patients. Patients managed by other physicians were not on the disclosed Vitamin D protocol. The staff member (nurse's aide) who stopped taking her vitamin D self-reported her breach of protocol after bringing Covid into the facility from outside. Only one of the 13 Covid positive patients during the six quarter study period was cared for by Dr. Mussett. Excluding this breach of protocol, the total number of Covid positive patients over 15 months totaled two patients. A newly admitted patient came into the facility with undiagnosed Covid. She was infected by family members prior to her admission. She died not long after her admission. Her death was the only Covid death during the nearly 15 month study period. She was not a patient of Dr. Mussett's. It is presumed that she was Vitamin D deficient. Two fresh staff hires began working before their Vitamin D level was tested and elevated into the safe range. They were infected outside the facility before being hired.

When compared to the other two nursing homes in Rio Grande City, Retama Manor's number of Covid cases per staff member was 45% less than the other two nursing homes. Dr. Mussett has patients at all three nursing homes in Rio Grande City. During the study period, only two of his patients tested positive.

Embodiments of the invention: (1) Enables cities to restore public confidence in the safety of indoor spaces (buildings, buses, subways). (2) Enables the public to check the safety of public indoor spaces before they go in. (3) It is technology that makes people feel safe again, that undermines fear, which becomes a reflexive part of daily life, which causes people to "instinctively" look at these colorimetric panels upon entering public spaces. (3) These panels will become vitally important to the future of cities. As new, more dangerous respiratory potential gain-of-function pathogens are released, safe indoor absolute humidity will become extremely critical. Without safe indoor absolute humidity, it will be impossible to proactively keep public spaces safe against stealth respiratory potential gain-of-function pathogens. (4) There is an urgency to produce these panels as soon as possible. Without them, people will have no way of knowing whether the indoor air inside a building which they enter is viral safe.

Components: (1) Sensor and board. (2) Measures absolute humidity in real time. (3) Wi-Fi® 5 connectivity module. (4) Digital color panel. (5) Enclosure. (6) Power Supply, which could be alternating current (AC), battery, and solar. The primary function is continuous monitoring of absolute humidity. In an embodiment, an algorithm converts sensor output to a signal that drives the color display which displays green when AH is ten or above. The color displays yellow when AH is 8 to 9.9. The color displays red when AH is below 8. In an embodiment, Wi-Fi connectivity may be used to upload sensor data to the cloud and to a service that centrally monitors AH data and communicates this data to users. Support could be provided similar to security systems with alarm monitoring provided for unsafe condition detection.

Embodiments of this invention may be available in different configurations: (1) Different panel sizes. (2) Different mounting configurations: (a) On floor stands. (b) Countertop or tabletop displays. (c) Wall mounts (d) Portable mounts to fit on a backpack which has an audible alarm that warns user when they are entering indoor air which is not viral safe. (3) Central monitoring service.

In an embodiment, the following protocols are provided: (1) Immediate treatment utilizing the VIRAL FIRE EXTINGUISHER®[6] with characteristics as follows: (1) Taken immediately when early viral symptoms first appear. (2) Similar to an insurance policy against tragedy. (3) Substantially decreases the risk of deaths and hospitalizations. (4) No testing, no doctor's visit, and no prescription. (5) Non-pharmaceutical treatment packs with a targeted cost of under $25 for a complete ten day course.

Nearly every American, both vaccinated and unvaccinated, is now immunosuppressed. A new normal is urgently required if cities are to survive in the age of potential gain-of-function pathogens. Viral Fire Extinguishers must be widely distributed in businesses, for example, in vending machines, and homes. People begin treatment within minutes of viral symptoms first appearing.

[5]Wi-Fi is a trademark of Wi-Fi Alliance.
[6]Viral Fire Extinguisher is a registered trademark of Jeff Gusky.

A culture of viral safety is vitally important to achieve and maintain CMHI. This includes widespread adoption of routine habits like daily gargling of mouthwash and the daily use of antiviral nasal spray, both of which lower viral load in the nasal passages and the oral cavity. A culture of viral safety may include the widespread embrace of new survival skills like the immediate use of a Viral Fire Extinguisher when viral-like symptoms first appear.

CMHI is a way to make cities in highly vaccinated countries safe again. CMHI requires: (1) Safe indoor absolute humidity in public buildings. (2) Rapid, population-wide mass testing and treatment of vitamin D to elevate entire cities and workforces into the upper end of the normal range (3) Daily non pharmaceutical nutritional supplements to: (a) Restore and maintain a healthy gut microbiome. (b) Maintain antiviral priming and proper micronutrients.

CMHI is about risk management for cities and businesses. In an embodiment, products, services, processes are designed to inspire new cultural norms that form the critical infrastructure required for modern cities to survive in an era of potential gain-of-function pathogens. With uncompromising altruism, an approach that earns the public's trust with results and deliverables detached from politics that help everyone.

The new normal will include absolute humidity sensor panels and Viral Fire Extinguishers in nearly every public building and home. A new consciousness of risk is required to survive in the post-Covid era. Prevention of cytokine storm and imprinting on a massive scale is the only way to: (1) Prevent mass death and disability among vaccinated people. (2) Preventing cytokine storm in both vaccinated and unvaccinated. (3) Prevent a complete breakdown of the healthcare system should a new gain-of-function pathogen be released. (4) Prevent massive loss of life in the US military which is now at risk because so many members of the military are vaccinated.

A culture of viral safety at the local level is essential. The disclosed approach facilitates a means to empower communities and businesses to save themselves from existential threats caused by gain-of-function pathogens. With simple, inexpensive measures local people can: Keep their families safe and preserve their freedoms as Americans.

With the disclosed approach, the new paradigm is CMHI. CMHI becomes a ubiquitous feature of modern life once societies across the globe come to realize that CMHI is the only way to make public indoor spaces viral safe against current and future gain-of-function pathogens. CMHI represents the only way to make modern city life sustainable since modern cities can only exist if indoor public spaces are viral safe. The public learns that CMHI is the only way to mitigate the risks of a potential gain-of-function pathogen which could lead to a crippling of the US military, mass death, and disability among the vaccinated. Long term spike protein injuries may include: Cancer, heart attacks, strokes, accelerated aging and shorter life span, Alzheimer's, Parkinson's disease, and recurrent Covid leading to irreversible organ injury and brain damage that happens slowly over a period of years. These injuries cannot be felt while they are taking place.

Risk managed CMHI (which is optimized CMHI achieved through proprietary, industry specific risk management protocols) revolutionizes the risk management industry and will become an essential new element of modern business risk management practices. CMHI becomes the new standard of Viral safety in public spaces, CMHI represents the only way to harden workforces and cities against bio terrorism. CMHI represents the only way to harden at-risk populations: All senior care businesses, detention centers, and cruise ships will need CMHI. CMHI is something the public will come to expect and demand before entering public indoor spaces. CMHI is something that employees will come to expect and demand as a precondition to coming to work. CMHI revolutionizes workforce resilience in an era when a high percentage of the workforce has permanently damaged immune systems.

CMHI markedly increases workforce productivity and markedly decreases absenteeism. Substantially increases state funding of public schools due to increased attendance. Keeps families' safe by helping mitigate the risks that a vaccinated employee who has become an asymptomatic carrier of disease will bring an infection home from work that harms their family. Keeps workplaces safer by helping mitigate the risks that a vaccinated employee brings diseases into the workplace from outside. CMHI helps enable the millions of vaccinated people whose immune systems have been permanently injured due to imprinting, to: (1) Help individuals mount an adequate immune response against respiratory viral infections to help prevent cytokine storm leading to hospitalization and/or death (2) Help populations mitigate their risk of mass death and/or mass disability from potentially lethal forms of Covid and other potential gain-of-function pathogens now on the horizon.

Antiviral Priming. Countries with the lowest rates of Covid in the world are in African countries where large parts of the population routinely take Ivermectin to prevent River Blindness and Elephantiasis and Hydroxychloroquine to prevent malaria. These drugs also have proven antiviral properties. Because so many people in these countries have background levels of these drugs in their bloodstream at all times, they are protected against Covid and certain other viral illnesses. The background drugs may include, for example, but are not limited to Ivermectin, and Hydroxychloroquine. These drugs along with Remdesivir and Paxlovid are enzyme blockers that interfere with viral replication. There are also numerous unregulated food supplements which also are able to produce similar enzyme blockade(s). Taken orally, these food supplements have limited bioavailability. The bioavailability challenge can be overcome by delivering them with an advanced nanotechnology delivery system that can be taken by mouth and which partially overcome the problem of bioavailability. These food substances can be taken on a daily basis using a nanotech delivery system. The goals are to emulate what certain African nations have achieved where a high percentage of people have background serum blood levels of bioactive antiviral enzyme blockers present at all times. This strategy will be particularly valuable to Covid vaccinated people who can help mitigate their vulnerability to infections, cancer, heart attacks, strokes, autoimmune diseases and many other dangers.

In an embodiment, people are able to "see" safety using colorimetric panels. Viral safety certified buildings and workplaces will be recognized by viral safety certified logo at entryways of qualifying businesses. These companies can also publish real time measurement of the Viral Safety Index®[7] (color correlated measure of viral safety based on indoor absolute humidity) on their website. These companies can also publish data dashboards for internal use by their workforce to visualize how CMHI makes their workplace safer.

[7]"Viral Safety Index" is a registered trademarks of Jeff Gusky.

A culture of viral safety becomes part of everyday life in viral safe cities. This culture breaks through fear and empowers local communities and businesses to manage bioweapon pandemics on their own. Absolute Humidity will become the new standard for predicting viral safety and danger indoors. Continuous monitoring of indoor absolute humidity will become commonplace. Viral safety panels will be everywhere. Personal monitoring solutions (purse, backpack clip-ons or wearable monitors which attach to one's belt) will become popular.

A revolution in risk management may be supported by disclosed industry-specific risk management protocols. These protocols represent unique, step-by-step industry-specific methods to achieve CMHI for businesses within a given industry. Examples may include senior care businesses such as: (1) Nursing homes. (2) Assisted living. (3) Home health. (4) Adult day care. (5) Rehab centers. Other examples may include long term care facilities, prisons, and jails. In addition to the industry-specific protocols, staff members in each industry are trained in simple daily hygiene measures which lower viral loads in their nose, mouth and lungs. Viral Fire Extinguisher packs will be readily available for immediate use when staff, clients or visitors first develop viral-like symptoms. In settings such as nursing homes, college dormitories, prisons, inpatient rehabilitation centers and other similar settings, where a person will become part of a group of people occupying an indoor space for a sustained period of time (more than 1 day), they will be offered a rapid CMI treatment pack to begin the process of rapidly elevating their serum vitamin D level into the safe range along with initiation of antiviral priming and rapid achievement of a healthful gut microbiome. The rapid CMI treatment packs will be administered prophylactically while that person is awaiting formal testing and treatment of their serum Vitamin D level. A rapid CMI prevention pack will be administered prophylactically to every new patient or inmate while waiting for that person's Vitamin D level to be tested and treated. Absolute humidity colorimetric panels will be placed throughout a given facility. Gut Microbiome restoration and maintenance products will be implemented to boost a form of CMHI which happens when entire populations and workforces collectively have healthy gut microbiomes. The disclosed approach helps mitigate risk of cytokine storm and many types of infections including infectious diarrheas (bacterial, viral, fungal).spreading through a nursing home or other facility.

Adoption of CMHI in a given school should increase state funding because funding is tied to attendance and CMHI can markedly increase attendance.

Absolute humidity colorimetric panels placed throughout a cruise ship vessel may be used to signal viral safety to passengers and crew. The distinction of becoming Viral Safety Certified®[8] may be used by cruise lines as a marketing tool. Pre-cruise viral safety packs may be sent to passengers a few weeks before departure and taken, for example, starting 10 days before their date of embarkation may be used to facilitate CMHI in the cruise ship.

Airport terminals face considerable risk for potential gain-of-function engineered pathogen attacks when the indoor absolute humidity inside an airport terminal falls below the viral safe range. This risk is evident when passengers re-enter the airport terminal after leaving their flight. While at altitude, passengers breathe low absolute humidity for an extended period of time. Inflight absolute humidity is typically about 2 to 3 gm/m³. This impairs the protective barrier against airborne pathogens which exists on the lining of the respiratory tract. After they leave their flight and walk through an air terminal with dangerously dry air, they are exceptionally vulnerable to pathogens in the air. This is why people routinely develop upper respiratory tract infections after flying on airliners.

Placement of absolute humidity colorimetric panels and indoor humidity modifications may be implemented to make meat packing plants viral safe. Workers in meatpacking plants must function in cold indoor environments where the absolute humidity is low. Absolute humidity can be safely elevated into the viral safe range inside meat packing plants even while maintaining the necessary cold air temperatures.

Viral Fire Extinguisher packs may be administered to every new inmate in detention facilities while that person's vitamin D level is tested and treated. Absolute humidity colorimetric panels may be displayed throughout every facility. Gut microbiome restoration and maintenance to boost CMHI may be used to mitigate the increasing risks to vaccinated people of many distinct types of infections, such as infectious diarrheas (bacterial, viral, fungal).

[8]Viral Safety Certified is a registered trademark of Jeff Gusky.

Absolute humidity colorimetric panels may be placed throughout retail, commercial office space, hotels, and restaurants.

Prolonged exposure to altitude appears to accelerate spike protein endothelial disease in airline flight crews. Special testing can be performed to diagnose stealth spike protein injuries at an earlier stage. If warranted, protocols can be used to mitigate the risks of spike protein endothelial injuries while there's still time to make a difference.

In an embodiment, in acute care hospitals, surgical hospitals, and free-standing surgical centers, surgeons would routinely advise elective surgical patients to take a 10 day immune booster pack (similar to the Viral Fire Extinguisher) just prior to the day of surgery in order to markedly lower the incidence of postoperative wound infections and surgical complications.

The brains and vital organs of nearly every living American have been inoculated with spike proteins. This crisis affects vaccinated and unvaccinated people. Heart attacks, strokes and pulmonary emboli are now on the rise caused by spike protein induced thromboembolic disease (i.e., blood clots and amyloid clots). These dangers manifest suddenly, without warning, in seemingly healthy individuals. Rising numbers of accidents in single operator industries like bus drivers are occurring. Data from the Federal Motor Carrier Safety Administration show that fatalities in Texas bus crashes rose 133% from 2020 to 2022. Nationally, bus crashes have risen 46% during this two year period. Acute thromboembolic events can cause sudden incapacitation or death in workers who are single operators. In occupations where a heart attack, stroke or pulmonary embolism can suddenly incapacitate the operator of heavy equipment, such as, eighteen wheeler trucks, buses, helicopters, trains and cranes and can strike with no warning, tragic accidents will follow that may cause excessive loss of lives, immense property damage, and extreme business liabilities.

Measuring and mitigating the risk of catastrophic spike protein related thromboembolisms in single operator industries before tragedy strikes is now more important than ever. The ongoing surveillance and mitigation of single operator risk should become an indispensable part of standard risk management practices into the future. The risk of sudden incapacitation or death will likely continue for years because spike proteins may remain in the brain and vital organs indefinitely.

The ongoing surveillance and mitigation of single operator risk should become an indispensable part of standard risk management practices in single operator industries including: Trucking companies, bus drivers (for schools and public transportation systems), train and subway operators, crane and heavy equipment operators, helicopter and commercial fixed wing single pilot operations, and tugboat operators, all of which are at-risk.

Potential gain-of-function pathogens are here to stay. The natural immune defenses that have protected human beings against respiratory pathogens for hundreds of thousands of years have been rendered obsolete by gain-of-function engineered viruses whose ability to overcome natural protective barriers exceeds anything which exists in the natural world. The only form of herd immunity that can stop potential gain-of-function pathogens is CMHI. CMHI proactively shields human beings against future potential gain-of-function pathogens that may not presently exist. CMHI makes entire populations less vulnerable to pathogens overall, even pathogens to which their immune systems have never been exposed.

Executives must learn to manage bioweapon risks if their businesses and communities are to survive. Critical synergies exist between the four key switches that turn on CMI. Early versions of Covid could be controlled when one or two of the four CMI switches were partially optimized. But Covid has rapidly become the most contagious virus in human history. This is because the strength of receptor binding has increased dramatically. Safety against these new variants requires that CMHI is fully optimized. This means that all four types of individual CMI must be fully optimized to help shield cities and workforces against coming bioweapon threats.

Vitamin D was never a vitamin; vitamin D has always been a hormone. As a hormone, Vitamin D is critical to a properly functioning immune system which requires proper dosing with considerations for toxicity and safety. Maintaining a safe Vitamin D level cannot be done casually. Just like all hormones (i.e., insulin, thyroid, estrogen and testosterone), the only way to know the level and ensure safety is to measure the serum hormone level with a blood test. An individual cannot "feel it" when that individual's vitamin D is low. This is why many tens of millions of people are "accidents waiting to happen" and do not realize it. Beyond just Covid and other potential gain-of-function pathogens, their vulnerability to cancer, heart attacks, strokes, and autoimmune diseases is much higher than it should be with a properly functioning immune system. These risks can be mitigated for pennies per day. The accepted normal range for vitamin D has been 30 to 100 ng/ml for years. The upper end of the range has been the conventional standard for many years. It is not at all controversial. However, the lower end of the range at 30 ng/ml is widely misunderstood. This level works fine for the prevention of osteoporosis in postmenopausal women but is grossly inadequate to prevent heart attacks, strokes, cancer, autoimmune diseases, diabetes and dangerous pathogens like Covid in both men and women.

There is a "hidden" immune reserve capacity that is tapped when people maintain their vitamin D in the upper end of the normal range, ideally, as close to 100 ng/ml as possible. Now that more than half the population of the United States have permanently damaged immune systems due to the vaccine complication called imprinting, tapping this hidden immune reserve capacity is critical to rescuing what is left of damaged immune systems in tens of millions of people. This scalable method of rapid immune rescue can potentially enable tens of millions of people with impaired immunity to survive potentially lethal Covid variants as well as gain-of-function engineered pathogens. In this context, Vitamin D in the upper end of the normal range will be a matter of life and death for many vaccinated people.

The United States and many other countries can never go back to the time before Covid. The high infectivity of gain-of-function engineered pathogens has permanently surpassed the ability of natural human defenses to block deep lung infections. Only herd immunity can protect societies against new pandemics. CMHI is the only form of herd immunity that is possible against many deadly pathogens including rapidly mutating airborne viruses like Covid. Because of this fact, only CMHI can make modern cities livable and safe long term.

People who develop early symptoms of a possible respiratory viral illness have only a short window of time where the potentially deadly risks of cytokine storm and imprinting can be blocked. Immediate treatment operates by rapid induction of CMI. If CMI can be activated in time, it can potentially limit the increase of viral antigen following infection from rising above a critical threshold level. By keeping the antigen level below this threshold, CMI can mitigate the risks of cytokine storm and imprinting. By blocking cytokine storm and imprinting, rapidly induced CMI can save many millions of lives.

CMI is the body's first line of defense against infections of all kinds. It responds immediately to invading pathogens. However, CMI is often ineffective because of: 1) longstanding, widespread immune suppression affecting the vast majority of Americans and 2) the rapidly emerging problem of permanent mass injury now affecting the immune systems of tens of millions of people due to imprinting. When CMI is not fully activated or "switched on," vaccinated people are particularly at risk. If rapidly rising levels of viral antigen following infection are not rapidly thwarted with immediate treatment, the adaptive immune system (i.e., antibody immunity) becomes triggered in 3 to 5 days. This represents a particular danger to many vaccinated people because of immune imprinting. The immune systems of vaccinated people who have been harmed by imprinting have been permanently reprogrammed not to work. Imprinting causes them to always produce obsolete, non-neutralizing antibodies that are incapable of killing current versions of Covid. Furthermore, once triggered, the non-neutralizing antibodies produced by vaccinated people injured by imprinting rapidly disable their CMI. Thus, the activation of imprinting in vaccinated people functions like a "kill switch" that blocks CMI and their ability to defend themselves against dangerous new variants of Covid or other dangerous pathogens. On the contrary, when CMI is fully "switched on," it is remarkably effective at killing and clearing the attacking virus (i.e., the attacking viral antigen) from the bloodstream quickly. It is so effective that adaptive immunity (and thus imprinting in vaccinated people) in many, if not most cases, never gets activated when CMI is fully switched on. Preventing imprinting is very time sensitive. Imprinting gets switched on in 3 to 5 days after a viral infection begins if the critical antigen threshold is exceeded. Once this happens "the cat is out of the bag" and it is too late to stop the perilous impairment of CMI that may be caused by imprinting. Cytokine storm can also be blocked by preventing the antigen level from surpassing the critical threshold which triggers the adaptive immune system (i.e., antibody immunity) to turn on. In summary, by rapidly clearing virus from the bloodstream in the first several days after infection: (1) Imprinting can be blocked which in turn prevents CMI from being switched off. This is critical to helping save the lives of tens of millions of vaccinated people whose immune systems have been permanently injured by imprinting. (2) Cytokine storm is blocked which in turn prevents hospitalizations and deaths from Covid, Avian Flu, MERS, severe Influenza, and other deadly pathogens that kill by causing cytokine storm. Thus, immediate treatment is potentially lifesaving for both vaccinated and unvaccinated people. The disclosed approach prevents imprinting and cytokine storm and facilitates the "jumpstarting of CMI" fast! The prototype for these measures is being tested and being developed in Starr County, Tx since late 2020. Prototypes for the Ten Days To Safer Vitamin D™[9] rapid treatment protocol which rapidly and safely elevates entire populations from dangerously low levels of serum vitamin D to viral safe levels of serum vitamin D in ten days without side effects. This protocol involves performing mass testing for Vitamin D, Calcium and Magnesium before and after initial treatment as well as at about 4 months following initial treatment to verify serum Vitamin D levels are properly maintained. A lower dose version of this protocol was developed for poor communities where the cost of Vitamin D testing was out of reach of most people. This lower dose protocol suffices to rapidly elevate vitamin D levels high enough to help rapidly activate CMI to keep the antigen threshold below the critical level in many people. However, the Vitamin D dose is low enough that testing is not required before treatment to maintain safety. Also disclosed is a multi-enzyme blockade approach that combines over-the-counter nutraceuticals to achieve an effect that may potentially surpass Ivermectin, Paxlovid, Remdesivir or Hydroxychloroquine (i.e., combining compounds like Artemisinin, which won the Nobel Prize in Medicine in 2015 with other nutraceuticals). The rate limiting factor for using nutraceuticals as antivirals is bioavailability. By utilizing a nano drug technology that can transport the above multi nutraceutical payload into the gut where it can be absorbed into the bloodstream at higher rates, the effective absorption surpasses previous methods. In addition, the multi nutraceutical cocktail provides powerful anti-inflammatory

[9]Ten Days To Safer Vitamin D is a trademark of Jeff Gusky, effects which, along with vitamin D can help counter cytokine storm. In the disclosed approach critical micronutrients like Zinc and Magnesium may be included which are essential to blocking viral replication. Their inclusion helps keep the antigen level below the critical antigen threshold.

Timing is everything when blocking cytokine storm and avoiding imprinting. Treatment needs to be administered as soon as possible (ASAP). Ideally the treatment should begin within ten minutes of the first sign that a viral infection may be coming on. This requires an exceptionally large societal paradigm shift. Viral Fire Extinguisher treatment packs must be physically present in businesses and homes across the country so that people can access them quickly when needed. People must embrace a new normal: (1) As soon as symptoms appear that could be viral, one reaches for a Viral Fire Extinguisher, preferably, within ten minutes and ideally in under an hour. In order to achieve the desired timing, the use of the viral extinguisher should occur without testing, without a doctor's visit, and with no delay. Immediate treatment means starting treatment as soon as a person feels a potential viral illness coming on. The Viral Fire Extinguisher is like a "universal antidote" against respiratory viral potential gain-of-function pathogens because it helps block: cytokine storm, which is the common cause of death in Covid, Avian Flu, MERS, and Influenza. This approach also helps avoid imprinting which all but paralyzes CMI. These measures are critical to saving the American military.

CMHI exists when the synergy of all four types of triggers for CMI are optimized in entire populations at the same time: (1) Vitamin D herd immunity. (2) Viral safe indoor absolute humidity herd immunity. (3) Gut microbiome herd immunity. (4) Antiviral priming.

Covid spike proteins often break away from the virus, circulate freely in the bloodstream and then penetrate cells in the brain and vital organs throughout the body. Once inside cells, spike proteins may remain indefinitely. Spike proteins appear to be causing prion-related diseases such as Creutzfeldt-Jakob disease as well as amyloidosis, autoimmune, and heart disease. Spike proteins also induce an unhealthful gut microbiome (i.e., dysbiosis).

A healthful gut microbiome can help vaccinated people strengthen their remaining immune function against Spike Protein Endothelial Disease (SPED), cytokine storm, and infectious diarrhea. A healthy gut microbiome can make the difference between who lives and who dies as well as who is hospitalized.

There is a connection between serum Vitamin D levels and: (1) Whether CMI functions properly or not. (2) The ability of the immune system to protect the body against rapidly mutating viruses and potential gain-of-function pathogens in particular. (3) A serum vitamin D level in the upper end of the normal range activates a hidden immune reserve capacity of the immune system. When activated, this hidden reserve capacity can mitigate dozens of serious, painful, debilitating and often life threatening medical problems.

There is a connection between indoor absolute humidity and: The activation of mucosal immunity, which is a branch of CMI. Mucosal immunity functions as a barrier to entry of pathogens into the body and is found on the mucosal surfaces of the mouth and nose all the way down to the deepest recesses of the lungs. Mucosal immunity is also found on the surface of the eye.

In order to facilitate blood testing, a national registry of qualified blood drawing personnel based in locales across the country, is formed. Local officials may be requested to assist with recruitment of these personnel by requesting the cooperation of local colleges and training facilities, asking them to provide access to their alumni lists of graduates who have been trained to perform routine phlebotomy. These graduates would come from professions such as, phlebotomists, certified nurse assistants (CNA), nurses, respiratory therapists, paramedics, medical technologists, nurses (LVN/RN), and the like. Recommendations and endorsements of this effort to assist local communities may be requested from college and technical school administrators, encouraging their alumni to consider joining the national blood drawing registry.

In order to facilitate blood testing, a national registry of qualified blood drawing personnel based in locales all over the country is formed. Local officials may be requested to provide access to alumni lists for those trained to draw blood. The professions are for example, but not limited to phlebotomists, certified nurse assistants (CNA), nurses, respiratory therapists, paramedics, medical technologists, nurses (LVN/RN), and the like. Recommendations may be acquired from the school officials to look at the opportunity. In an embodiment, local part-time workforce that has blood drawing skills in local areas may be recruited. A team of local, qualified people that have been trained for blood drawing, phlebotomy, specifically for venipuncture, that is, the collection of blood from a vein are recruited. The system supports date and location bulk blood drawing tailored for efficiency.

In an embodiment, smartphones may be used to match people having the blood drawing skills with events. The professions are for example, but not limited to phlebotomists, nurse assistants, nurses, respiratory therapists, paramedics, medical technologists, nurses (LVN/RN), and the like. In order to support an event, individuals with the blood drawing skills may enroll in a national registry. Those that are accepted into the national registry may sign up for an event in a manner similar to an Uber driver providing a ride based on an available time and vehicle. Benefits for signing up may include, for example, concierge phone lines to support counselling, buying services (various, babysitting, instant payment of paycheck, worker's comp, training, and the like. In an embodiment, the national registry may be administered by a payroll service, such as, Paychex®[10]. Those that are added to the registry become eligible to participate in calls to action. In an embodiment, sign up for a call to action may be for a schedule sign up accepting volunteers on a first come, first served basis. Only a limited number of people would be allowed to sign up for an event; however, in order to account for service provider's changes of schedule, 5-10 times the minimum number of people needed may be allowed to sign up. A targeted payment of the service providers may be $15-20 per hour adjusted by area to make sure payment is "well paid" for the time on duty. Local officials, judges, deans of universities may support providing alumni lists of relevant professions to facilitate recruitment and give alumni opportunities to make extra money. People sign up for registry for free.

Could use similar model for humidification model for HVAC to get modification if needed. HVAC experts, show up at commercial buildings, collect data for submission into a database identifying the location. Other experts analyze the data to perform load-calculation.

[10]PAYCHEX is a registered trademark of Paychex of New York, LLC,

Based on the load calculation, it is determined if existing equipment can be updated to get humidity to safe absolute humidity defined as 10 g/m³ year around or greater.

In an embodiment, testers may sign up for work with variable hours. An approach similar to volunteers for Ride-Share or Uber drivers may be supported. Pools of workers may sign up for scheduled hours at a location and payment may be adjusted based on need for additional workers.

FIG. 1 shows the steps taken by a process that activates Cell-mediated Herd Immunity (CMHI) in a plurality of people 100. At step 120, the process provides a scalable infrastructure to activate individual cell-mediated immunity (CMI) in the plurality of people. Protocols are established in the plurality of people to activate and maintain CMHI. Although the processes may be targeted toward a single person, in an exemplary embodiment, the scalable infrastructure supports, for example, but not limited to, a subdivision of a city, a city, personnel in a company, and the like. The protocols may include a protocol for establishing and maintaining an enclosed space absolute humidity, a serum concentration of vitamin D as measured by a blood test, a healthful gut microbiome, and an antiviral priming.

At predefined process 130, the process performs the enclosed space absolute humidity routines (see FIG. 2-12 and corresponding text for processing details). At predefined process 140, the process performs the serum concentration of vitamin D as measured by blood routines (see FIG. 13-14 and corresponding text for processing details). At predefined process 150, the process performs the healthful gut microbiome routines (see FIG. 15-16 and corresponding text for processing details). At predefined process 160, the process performs the antiviral priming routines (see FIG. 17-18 and corresponding text for processing details).

FIG. 2 shows the steps taken by an absolute humidity safety process 200. At step 210, the process facilitates activation of cell-mediated immunity (CMI) on mucosal surfaces in a respiratory tract of people in an enclosed space. The process determines as to whether the absolute humidity level is viral safe (decision 220). If is the absolute humidity level is safe, then decision 220 branches to the 'Y' branch which proceeds to step 260 which ends the process for FIG. 2. On the other hand, if not is absolute humidity level safe, then decision 220 branches to the 'N' branch which proceeds to run humidifier at step 250 which loops back to decision 220. This looping continues until absolute humidity level is safe, at which point decision 220 branches to the 'Y' branch exiting the loop. The humidifier may be a fixed-installation humidifier or a portable humidifier. The type of humidifier may be, for example, but not limited to: A drum style (bypass) that uses a pipe to bring water directly to a reservoir (a pan) attached to the HVAC system. A disc wheel style (bypass) which is similar in design to the drum style humidifiers replacing foam drumming with a number of plastic discs with small grooves on both sides. A bypass flow-through style (bypass—also known as "biscuit style" or many other, similar variant names) uses a pipe to bring water directly to an electrically controlled valve at the top of the humidifier. Spray mist types use a pipe, usually a small plastic one, to bring water directly to an electrically controlled valve where an atomizer forces the water through a tiny orifice causing it to break up into tiny particles in the humidifier. Additional types may include non-bypass flow-through (fan augmented), steam, impeller or centrifugal atomizer, under duct designs, and the like. The humidifier may be either integrated into heating, ventilation, and air conditioning (HVAC) system 230 or not integrated in the HVAC system 240. In some embodiments, an absolute humidity humidifier may be built into the HVAC system and control of the humidifier may be built into the thermostat controlling the HVAC system.

FIG. 3 shows the steps taken by a process that activates cell-mediated immunity (CMI) on mucosal surfaces in a respiratory tract of an individual 300. At step 310, the process provides a device disseminating moisturized air in a submicron (less than one micron) particle size to the individual ensuring the individual inhales moisturized air with a high concentration of absolute humidity level. Breathing the moisturized air enables distribution of water vapor with high absolute humidity into the deepest parts of the respiratory tract. The device may have a mask that covers nose and mouth. At step 320, the absolute humidity disseminated by the device is at least 10 g/m³. At step 330, the process may market usage of the device to include a set of scenarios wherein the individual has breathed in dry air or has been exposed to unknown biohazards. A portable device may be used to activate the CMI on the mucosal surfaces in the respiratory tract of the individual one or more times based on the situation. In some embodiments, the individual may be running an artificial intelligence (AI) mucosal services application which monitors the individual's environment and alerts the individual to use the portable device. At step 340, the usage scenarios for the process may include departing a plane, home health practitioners after leaving a client's home, repair person or service technician after leaving a serviced premise. FIG. 3 processing thereafter ends at 350.

FIG. 4 shows the steps taken by a process that indicates viral safety of enclosed spaces 400. At step 410, the process receives absolute humidity (AH) values AHV (AHV1, AHV2, . . . , AHVn) from a set of sensors S (S1, S2, . . . , Sn) placed at locations L (L1, L2, . . . , Ln). At step 420, the process compares the received absolute humidity values AHV (AHV1, AHV2, . . . AHVi, AHVn) to a viral safety safe value to determine a viral safety assessment of one of safe and not safe. At step 430, the process sends received data to a remote location. At step 440, the process stores received data in a database. The process determines as to whether all values are safe (decision 450). If all values are safe, then decision 450 branches to the 'Y' branch. On the other hand, if not all values safe, then decision 450 branches to the 'N' branch. At predefined process 460, the process performs the first action process if not safe routine (see FIG. 5 and corresponding text for processing details). At predefined process 470, the process performs the provide indication of indoor safety process routine (see FIG. 6 and corresponding text for processing details). FIG. 4 processing thereafter ends at 480.

Figure 5:
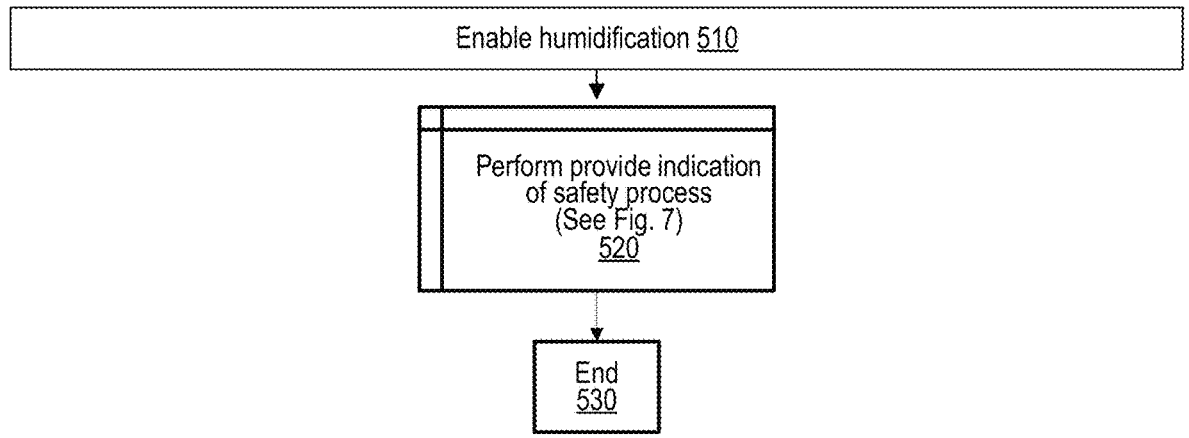

FIG. 5 processing shows the steps taken when the absolute humidity is not safe 500. At step 510, the process enables humidification. At predefined process 520, the process performs the provide indication of safety process routine (see FIG. 7 and corresponding text for processing details). FIG. 5 processing thereafter ends at 530.

Figure 6:
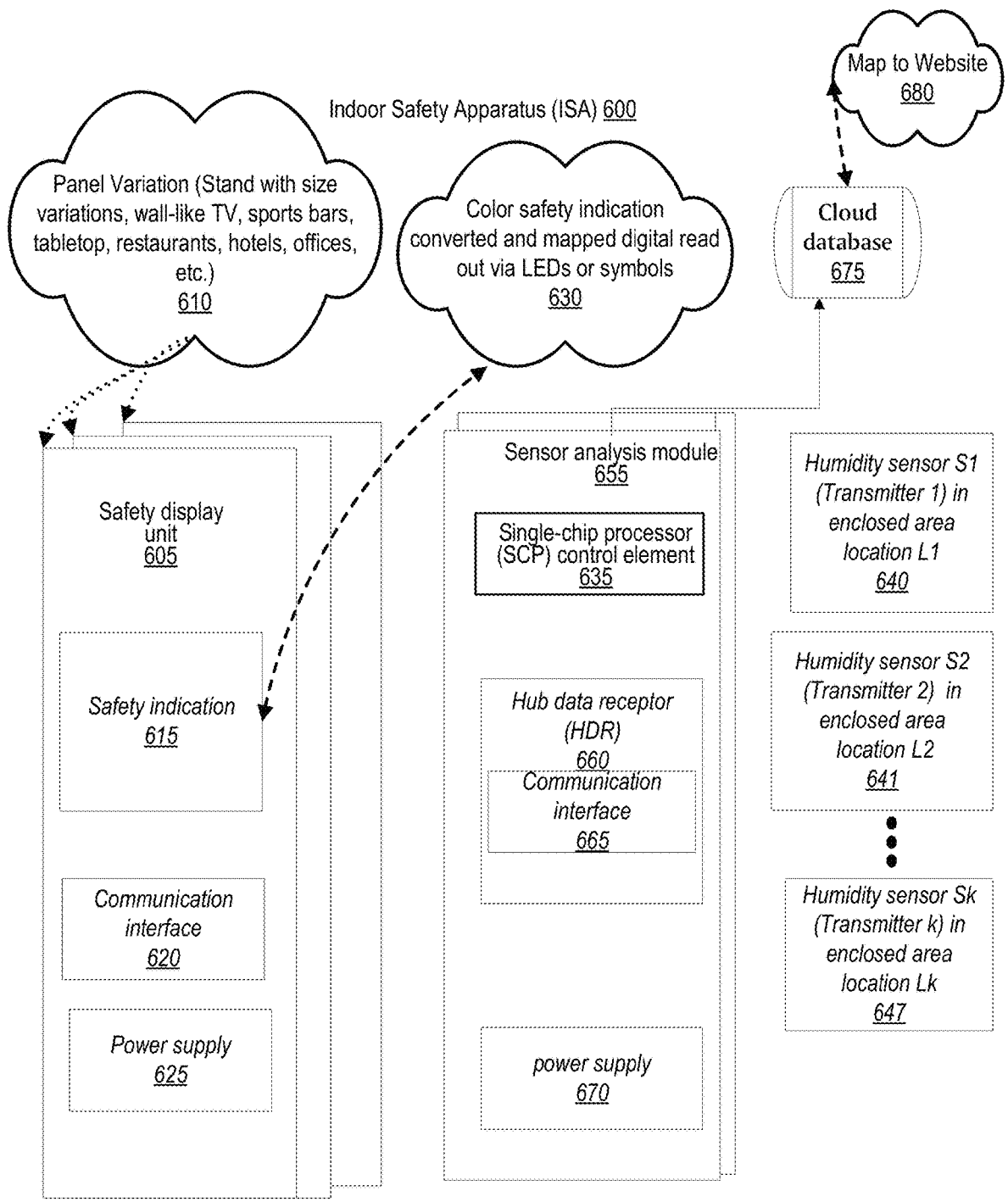

FIG. 6 depicts a schematic view of an indoor safety apparatus 600. In an embodiment, the indoor safety apparatus comprises a means for a safety indication 615 derived from a plurality of humidity sensors S (S1, S2, . . . , Sk) placed at locations L (L1, L2, . . . , Lk) [640, 641, . . . , 647]. In an embodiment each humidity sensor Si in the plurality of sensors is placed in a corresponding enclosed location Li and each sensor Si is also transmitting humidity data. In an embodiment, the transmitted humidity data is received by hub data receptor 660 via communication interface 665 which is embedded in sensor analysis module 665 having its own power supply 670.

Although many sensor analysis modules may be used to support processing of many sensors, each sensor is configured to only be processed by one sensor analysis module. For illustration purposes, only safety display unit 605 is discussed. The sensor analysis module 665 may use single-chip processor (SCP) circuit control element 635 to analyze the received humidity data and to perform actions based on policies. The actions may include sending the data to cloud database 675 which supports map to website processing 680. The actions may include utilizing communication interface 665 to send information to a plurality of safety display units. Although the information being sent may be different for different safety display units and each unit may have distinctive characteristics, for illustration purposes, only safety display unit 605 is discussed. Safety display unit 605 receives information via communication interface 620, is powered via power supply 625, and provides safety indication 615. Safety display unit 605 may take the form of a panel with many implementation variations, for example, but not limited to a stand with size variations, a wall-like TV such as found in a home or sports bar, a tabletop such as found in restaurants, hotels, offices, and the like 610. The safety display unit 605 may have an adjustable size allowing for expansion or contraction. The display unit 605 may support a viral safety alert feature and provide audio warnings. The integrated system may provide a safety alert when weather conditions suggest low absolute humidity will be dangerous indoors in the near future. The safety indication 615 may be, for example, but not limited to a color safety indication based on a converted and mapped digital read out display via light-emitting diodes (LEDs). At step 630, the color safety indication may be converted and mapped as a digital read out via LEDs or as symbols, such as, a thumbs up or thumbs down indicator. Although it is possible that the plurality of humidity sensors captures and transmits information from which absolute humidity is derived, in an exemplary embodiment, each sensor in the plurality of sensors directly outputs absolute humidity. The values received by the hub data receptor 660 may be cached and compressed by the sensor analysis module 655 taking advantage of consecutive duplicate values reported by a single sensor Si representing changes of values at times or changes in times. Similar compression techniques may be used when there is insignificant variation in absolute humidity values between the single sensor Si and another single sensor Sj. The compressed data may be stored locally and/or sent to cloud database 675.

In an embodiment, the indoors safety apparatus 600 may have safety display unit 605, which may include safety indication 615, a communication interface 620, and a power supply 625. The safety display unit 605 may have various panel variations 610, such as, for example, but not limited to a stand with size variations, a wall-like TV such as in a sports bar, a tabletop configured to display information, such as, in a restaurant. The display may include LEDs lights. Humidity sensors transmitters 1, 2, . . . , k 640, 641, . . . , 647 located in enclosed areas 1, 2, . . . , k capture humidity information and transmit the information to hub data receptor 660 in a sensor analysis module 655 that receives the transmitted information via a communication interface 665 utilizing a power supply 670. The power supply may be, for example, a battery, a USB connection, an alternative current (AC) power source, or even a solar powered power source or power source backup. The received humidity sensor data may be an absolute humidity value originating from the humidity sensors or may be converted to an absolute humidity value utilizing an algorithm loaded into the processor circuit control element 635. The sensor analysis module 655 converts the absolute humidity value to a form suitable for transmitting to the safety display unit 605. In addition, the sensor analysis module may also send the collected data to a cloud database 675. In some embodiments, data from the cloud database 675 may be sent or mapped for access at a website 680 corresponding to where the humidity sensor data is collected. The data may be collected, for example, from multiple different stores in a large building with separate offices or separate businesses. In an example embodiment, an entire mall may have a set of indoor safety apparatus ISA (ISA$_1$, ISA$_2$, . . . , ISA$_k$, ISAn), where each ISA$_k$ K=1, n collects humidity sensor data from a limited number of sensors that are close and may include multiple stores. A database may include an identification of placement for each sensor and a mapping of the placement to a store. In an embodiment, the real-time data including sensor measurements may be sent to the cloud database 675 and consolidated in a compressed form. The compressed form may, for example, identify a measurement, an initial start time of the measurement, and how long that measurement stayed the same. When the measurement changes, a change indication of when the change took place, and the change delta from the previous measurement. The cloud database 675 may support an application programming interface (API) allowing support from a web site or a service. The service may provide proactive notifications and/or alarms when indoor safety levels are not in the safe range. Support may be provided similar to a security system or integrated into a security system.

Figure 7:
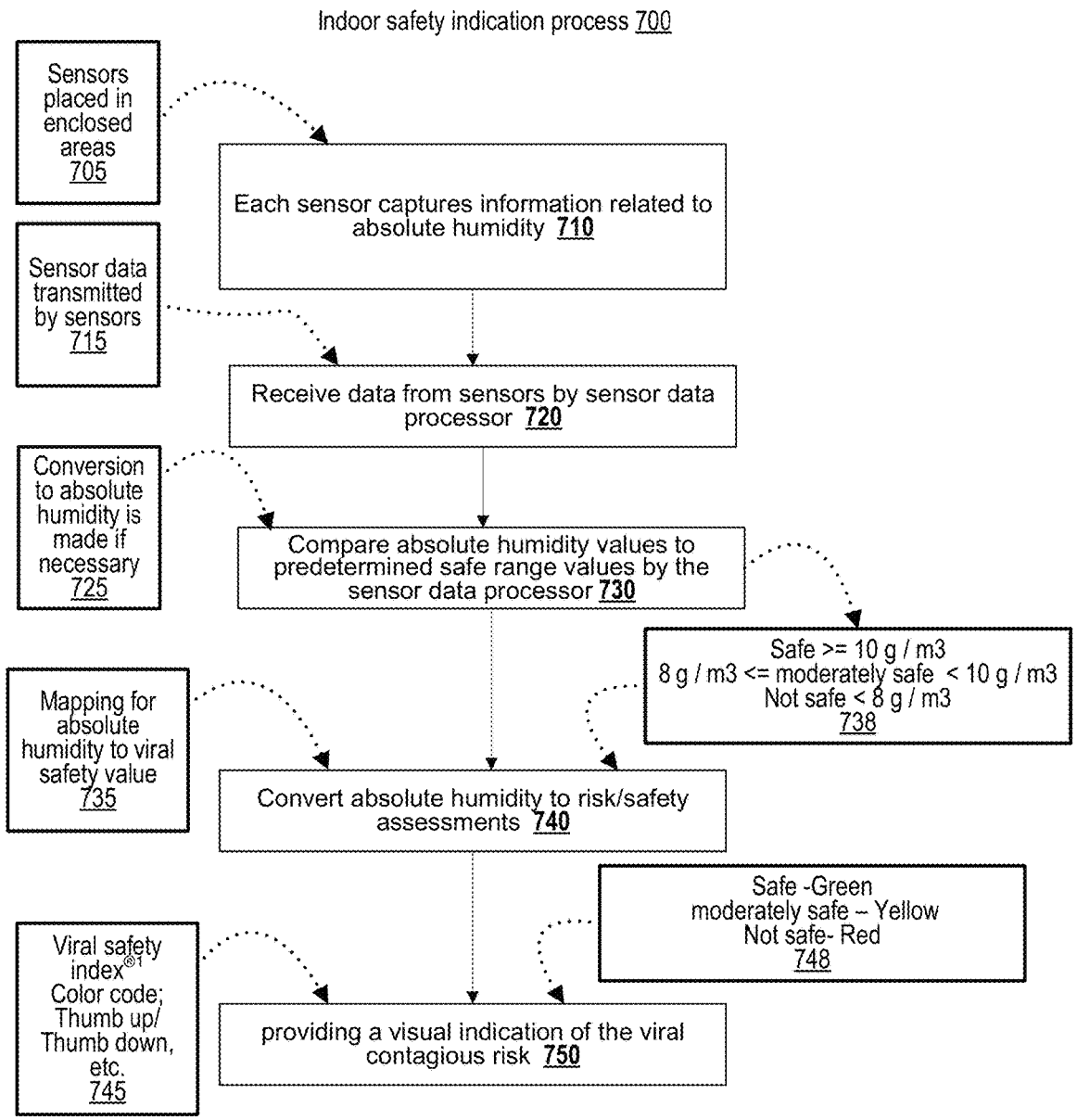

FIG. 7 shows the steps taken by an indoor safety indication process 700. At step 705, a plurality of sensors is placed at a plurality of locations, each location representing an enclosed area. At step 710, each sensor in the plurality of sensors captures information related to absolute humidity. At step 715, the sensor data is transmitted by sensors. At step 720, a sensor data processor receives sensor data. At step 725, conversions of the received data to absolute humidity are made if necessary. At step 730, the process compares absolute humidity values to predetermined safe range values. At step 738, the absolute humidity is characterized as safe when greater than or equal to 10 g/m$^3$, which is the mapping for absolute humidity to viral safety value 735. The absolute humidity is characterized as moderately safe when the absolute humidity is less than 10 g/m³ and greater than or equal to 8 g/m³. The absolute humidity is characterized as unsafe when the absolute humidity is less than 8 g/m³. At step 740, the absolute humidity to risk/safety assessments are made based on the mappings in step 738. At step 745, the viral safety index is depicted in some form, for example, via a color code, a Thumb up/Thumb down, etc. At step 750, the visual indication of the viral contagious risk is provided. At step 748, green is used to indicate safe, yellow is used to indicate moderately safe, and red is used to indicate not safe.

Figure 8:
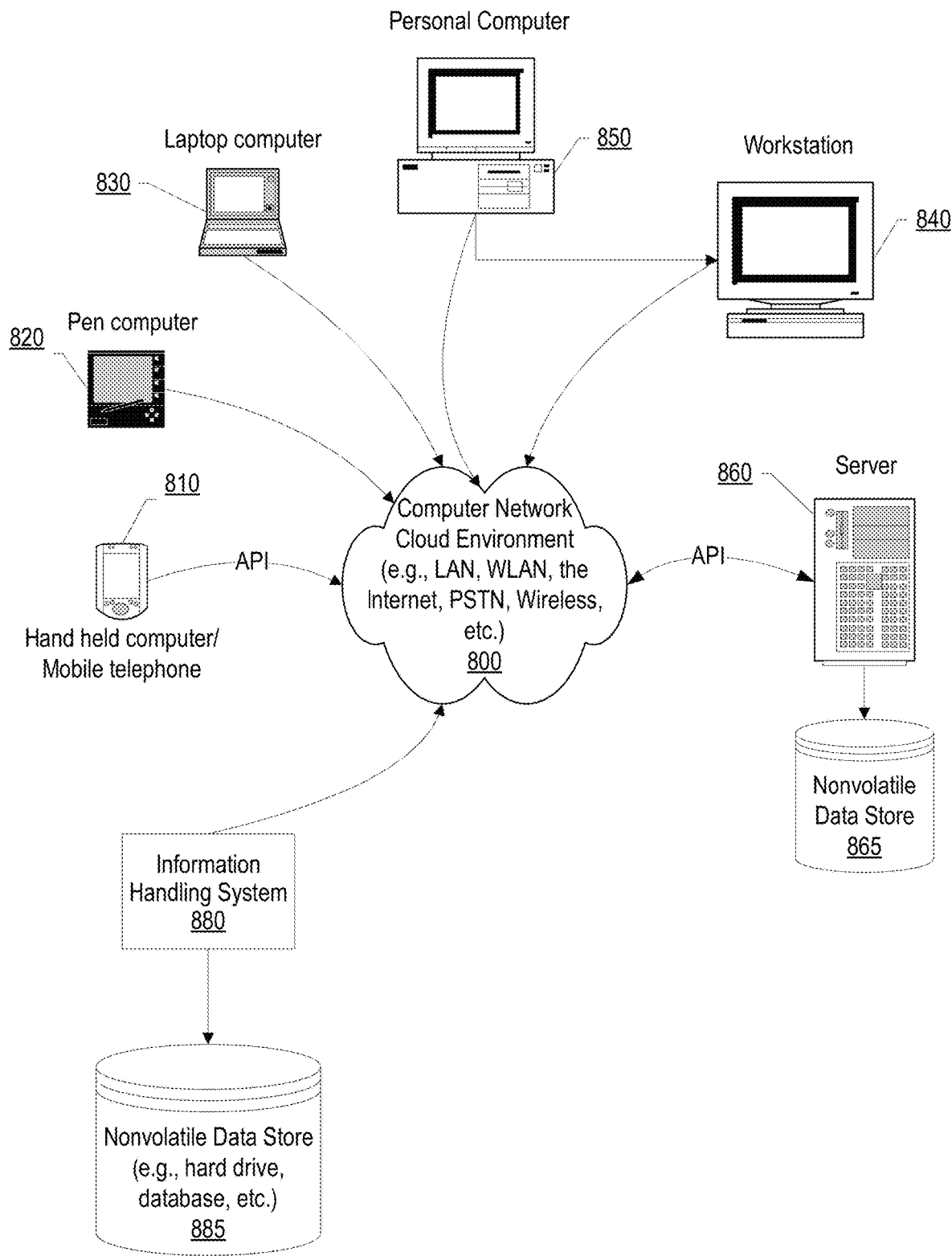

As shown, cloud computing environment 800 comprises one or more cloud computing nodes with which local computing devices used by cloud consumers, such as, for example, personal digital assistant (PDA) 810 or cellular telephone 810, desktop computer 850, laptop computer 830, and/or other mobile device such as an automobile computer system may communicate by sending and receiving data as needed. Nodes in the computer network 800 may communicate with one another. They may be grouped (not shown) physically or virtually, in one or more networks, such as Private, Community, Public, or Hybrid clouds as described hereinabove, or a combination thereof. This allows cloud computing environment 800 to offer infrastructure, platforms and/or software as services for which a cloud consumer does not need to maintain resources on a local computing device. It is understood that the types of computing devices shown in FIG. 8 are intended to be illustrative only and that computing nodes in cloud computing environment 800 can communicate with any type of computerized device over any type of network and/or network addressable connection (e.g., using a web browser). Types of computer networks that can be used to interconnect the various information handling systems include Local Area Networks (LANs), Wireless Local Area Networks (WLANs), the Internet, the Public Switched telephone Network (PSTN), and others. Examples of handheld computer 810 include personal digital assistants (PDAs), personal entertainment devices, such as MP3 players, portable televisions, and compact disc players. Other examples of information handling systems include pen, or tablet, computer 820, laptop, or notebook, computer 830, workstation 840, personal computer system 850, and server 860 archival storage systems 865, etc. Other types of information handling systems that are not individually shown in FIG. 8 are represented by information handling system 880 shown with nonvolatile data store 885. As shown, the various information handling systems can be networked together using computer network 800. In an embodiment, mobile phone 810 may have an integrated absolute humidity sensor and transmit captured absolute humidity information as well as location information to server 860 utilizing an API supported by server 860. Other computing systems may also include similar absolute humidity processing support.

Figure 9:
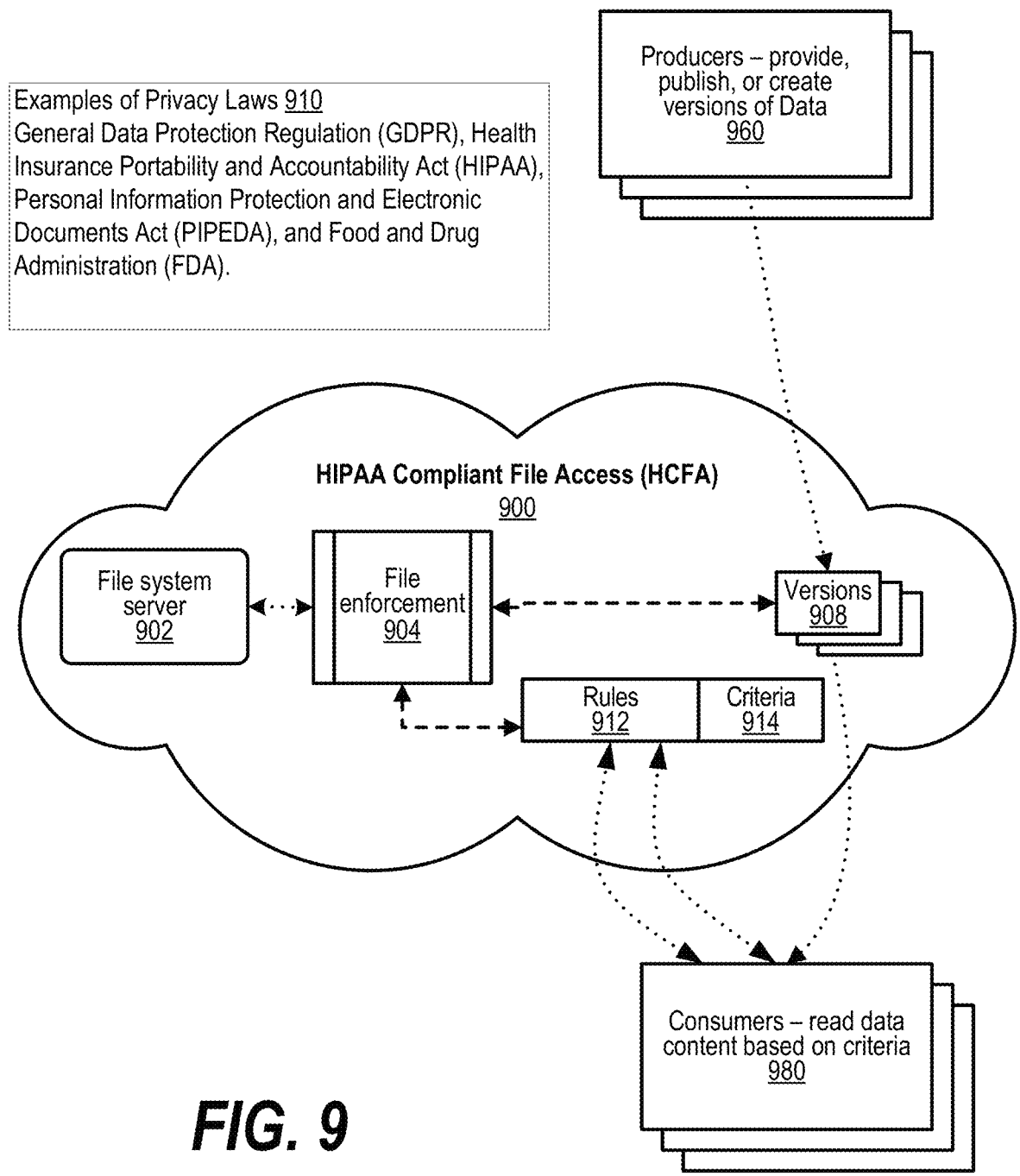

FIG. 9 depicts a schematic view of a HIPAA compliant interactive communication system overview 900. There are many existing legal file frameworks that are currently defined and approved or planned to be to be approved. Examples of privacy laws 910 include but are not limited to General Data Protection Regulation (GDPR), Health Insurance Portability and Accountability Act (HIPAA), Personal Information Protection and Electronic Documents Act (PIPEDA), and Food and Drug Administration (FDA).

Any of these file systems may be used to implement support for the capabilities described herein. When an updated version of data is added to the system, producers provide, publish, or create versions 908 of data 960. In an embodiment, a producer sends a request to add new data to a file system server 902. When the server 902 receives the request, the server 902 is responsible for ensuring data is encrypted as appropriate by utilizing a key manager 916. Proper usage of keys is important for separating access to data. There are many approaches for creating keys to be used to encrypt and decrypt data. In some embodiments, the strength of the keys and the complexity of preventing access to the keys may be chosen based on the sensitivity of the data. In some embodiments, the contents of the file are scanned for personal identity (PII) to determine the sensitivity of the data in the file. In some embodiments, the maximum classification of sensitivity found in the file may be used for the entire file, for example, a social security number in the file may be assessed as very sensitive. Different embodiments may use different rules, for example, there may be different levels of encryption based on a sensitivity of portions of the file, such as, by a mapping of field types to a level of sensitivity. As an example, the type of field may be known by a template of a document used to create the file. Then using information about the sensitivity of the data, the file system server 902 may ensure process file metadata enforcement 904 is configured to properly process data by setting up rules 912 and criteria 914 which allow consumers 980 to read data content based on and the rules 912 and the criteria 914. Although the privacy support is needed for user communications, absolute humidity information captured over time may also be processed based on consent.

Figure 10:
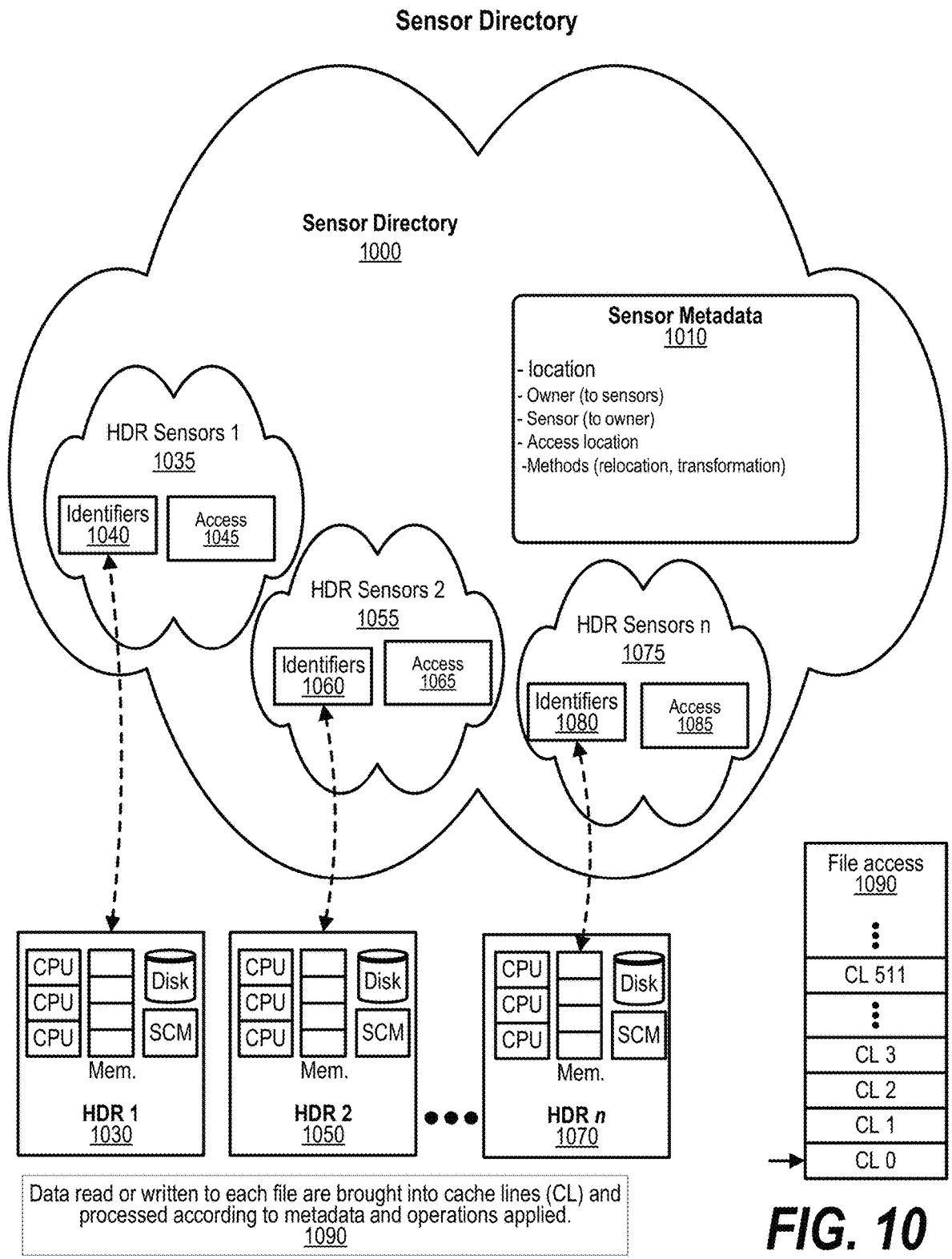

FIG. 10 depicts a schematic diagram of a system having support for a sensor directory 1000. The sensor metadata 1010 is included as files on the file system. Each user may have user owned data with user files and defaults. Although various formats may be used, in one embodiment, each type of data is represented by a structure with a type of structure identified as a first field in the structure which be used as a case or switch statement for processing the data in the structure. Separate structure types may be used for representing various data, such as, for example, but not limited to sensor identification, access rules, location of sensor, owner of sensor, and the like. The system may support tracking information by owner of sensors. In another embodiment, sensor data may be written as records in a database management system (DBMS) which supports indexing, look up, and complex queries. Each sensor is assigned to only one hub data receptor (HDR) 660. In FIG. 10, HDR 1 1030 has HDR sensors 1 1035 having identifiers 1040 and access information 1045, HDR 2 1050 has HDR sensors 2 1055 having identifiers 1060 and access information 1065, . . . , HDR n 1070 has HDR sensors n 1075 having identifiers 1080 and access information 1085. Data read or written to each file are brought into cache lines (CL) and processed according to metadata and operations applied 1090. File access 1095 brings in file records (user data) into local cache line(s) to process the data. Although FIG. 10 depicts multiple HDRs with separated support, a system could be tailored to a single HDR tailored for a single user or a single owner with only one set of defaults for the single owner.

A list of example sensor APIs 1100 is included in FIG. 11. Examples of sensor metadata APIs 1110 include: sOpen( ) Open a sensor; sClose( ) Close a sensor; sQuery( ) Query information about a sensor; sLMap( ) Map a location to a sensor; sOMap( ) Map an owner to a sensor; sErase( ) Erase information about a sensor; sChng( ) Change properties of a sensor; sRead( ) Read values of sensor. Many other sensor APIs may be supported such as assigning a sensor to an HDR.

Figure 12:
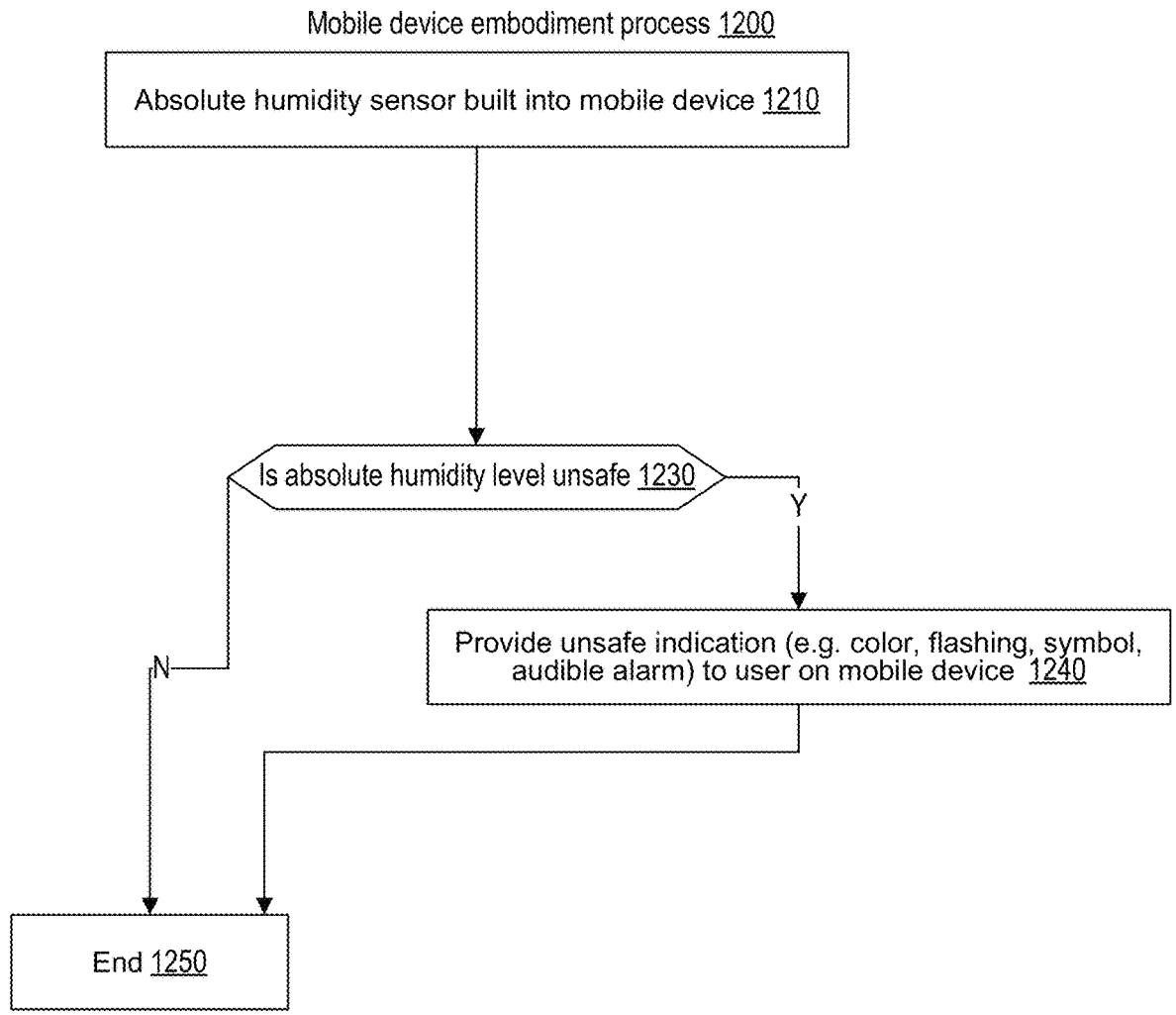

FIG. 12 shows an embodiment of an unsafe indication on mobile device process 1200. In an embodiment, the humidity sensor is built into mobile device 1210. The process determines as to whether the absolute humidity level is unsafe (decision 1230). If the absolute humidity level is unsafe, then decision 1230 branches to the 'Y' branch. On the other hand, if absolute humidity level is safe, then decision 1230 branches to the 'N' branch. At step 1240, the process provides unsafe indication to user on mobile device. The unsafe indication may be for example, a color, a flashing symbol, an audible alarm, or the like. FIG. 12 processing thereafter ends at 1250.

FIG. 13 shows the steps taken to achieve a serum vitamin D level in an upper end of a normal range in an individual as measured by blood 1300. At step 1310, the process provides a user interface supporting a step-by-step interaction with each individual in a group of people facilitating achieving a vitamin D level in an upper end of a normal range for each individual in a group of people. At step 1320, a time and place are identified, by the user interface, for an initial testing of the vitamin D level for the group of people where the initial testing of the vitamin D level includes a testing of calcium and magnesium and utilizes blood drawing professionals. At step 1330, the process analyzes results of the initial testing to identify an initial tailored regimen for each individual in the group of people.

At step 1340, the process ships an initial treatment pack to an individual based on the initial tailored regimen for the each individual in the group of people. At step 1350, the process retests the vitamin D level to identify a maintenance dosage of vitamin D for each individual in the group of people after the initial treatment pack is consumed. Alternatively, the process may identify an update to the initial treatment pack to get the individual's blood serum into the upper end of the normal range of vitamin D. At step 1360, the process retests the vitamin D level after the maintenance dosage of vitamin D for each individual in the group of people is consumed to verify the maintenance dosage. FIG. 13 processing thereafter ends at 1370.

FIG. 14 shows the steps for a process that utilizes mass testing and treatment to elevate a vitamin D level in a group of people into a viral safe range 1400. At step 1410, the process provides a user interface supporting interactive communication with an automated system that accesses a Health Insurance Portability and Accountability Act (HIPAA) compliant database such as shown in FIG. 9. At step 1420, the process applies a first mass blood extraction procedure to the group of people to form a first set of blood vials. At step 1430, the process sends the first set of blood vials for analysis of calcium, magnesium, and serum vitamin D to form a first set of test results. At step 1440, the process analyzes the first set of test results to identify a first tailored regimen for each individual in the group of people. During the analysis of the first set of test results, the process identifies individuals with problematic blood levels of calcium or magnesium that may need medical intervention. Those identified individuals may receive personalized communications with a medical professional instead of automated communications by the user interface. Typically, those identified individuals will need to have the problematic blood levels addressed before being allowed to participate in the achieving safe level of vitamin D protocol. Typically, the first tailored regimen is determined based on an individual's current serum vitamin D level and body mass index (BMI); however, specialized algorithms may be used based on numerous factors, such as, other conditions such as any previous relevant illness such as sarcoidosis or parathyroid disease, chronic kidney disease, and the like. The requested information would include demography, age, height, weight, sex so body mass index (BMI) could be calculated. In an embodiment, the upper end of the normal range of serum vitamin D starts at least 55 ng/ml. In some embodiments the ramp up dosage is targeted to reach between 80 ng/ml and 100 ng/ml attempting to compensate for the current impairment of CMI.

The user interface may include logic to process these conditions automatically as part of the AI training. Also, feedback from tracked results may be used to improve accuracy of doses needed for ramp up and for maintenance. At step 1450, the process applies a second mass blood extraction procedure to the group of people to form a second set of blood vials. The second set of blood vials are sent for analysis of serum vitamin D level and calcium to form a second set of test results. At step 1460, the process utilizes the second set of test results to determine a preliminary daily maintenance dosage. At step 1470, the process applies a third mass blood extraction procedure to the group of people to form a third set of blood vials after ingesting the preliminary daily maintenance dosage by the group of people for a period of time. The third set of blood vials are sent for analysis of serum vitamin D level to form a third set of test results. At step 1480, the process utilizes the third set of test results to confirm the preliminary daily maintenance dosage is maintaining the serum vitamin D level in the viral safe range or to modify daily maintenance dosage. In an embodiment, the treatment pack is to be consumed daily for 20 days and the preliminary daily maintenance dosage is consumed daily for at least 2 months following completion of the 20 day pack. At step 1482, the process applies a yearly mass blood extraction procedure to the group of people to form a yearly set of blood vials after ingesting a previous maintenance dosage by the group of people for a year. Analyzing the yearly set of blood vials for serum vitamin D level to form a yearly set of test results. At step 1484, the process utilizes the yearly set of test results to confirm the currently daily maintenance dosage is maintaining an individual's serum vitamin D level in the viral safe range or to modify daily maintenance dosage as appropriate. FIG. 14 processing thereafter ends at 1490.

FIG. 15 shows the steps taken by a process that facilitates activation of gut microbiome induced cell-mediated herd Immunity (CMHI) by activating gut microbiome induced individual cell-mediated immunity (CMI) 1500. The gut microbiome powder is designed to correct for widespread dysbiosis (unhealthy gut microbiome) as well as widespread insufficiency of essential micronutrients which are critical to healthy immune function. The gut microbiome powder is intended to be used in group settings by being mixed into a fruit smoothie or freshly mixed in other foods like yogurt to encourage a high level of daily consumption by each individual in a group without seeming like medicine. Institution-wide treatment of unhealthy gut microbiome creates CMHI by helping to optimize gut microbiome in groups. The utilization of the gut microbiome powder addresses the widespread absence of Gut Microbiome CMHI, especially in at-risk indoor group settings (i.e., detention centers, inpatient facilities of all kinds such as nursing homes, rehab facilities, psychiatric hospitals, long term care facilities, assisted living facilities, schools, cruise ships). Additional constituents, such as, but not limited to N-acetyl cysteine (NAC), quercetin, nattokinase, vitamin C, fucoidan, Omega 3 Fatty Acids, vitamin K, *spirulina*, lactoferrin, lutein, zeaxanthin, vitamin A, and N-acetyl glucosamine (NAG) 1518 may be added to the powder which have good bioavailability without the use of nanotechnology delivery system to achieve adequate blood levels in body of unregulated food products which mitigate the risks of cancer, neurodegenerative diseases, heart disease, strokes, autoimmune diseases, cytokine storm and Attention-deficit/hyperactivity disorder (ADHD). This approach addresses the recently identified increases in ADHD in young populations as well as increasing incidence of cancer, neurodegenerative diseases, heart disease, strokes, autoimmune diseases caused by widespread endothelial inflammation and widespread impairment of CMI.

In an embodiment, a green banana flour product made of the whole banana including the skin is manufactured as a prebiotic complement to the probiotic product. The green banana flour product may be baked into bread, muffins, rolls, pies, pancakes, and etc. The green banana flour product may be added to traditional wheat flour and promotes healthful gut microbiome in groups. In an embodiment, products containing flour made from the whole green banana may be promoted as viral safe breads, muffins, rolls, pies, pancakes, and etc. Helps to restore gut microbiome by potentiating the growth of gut microbiome.

At step 1510, a consumable product is manufactured in a form of a powder to be ingested by a group of people wherein the consumable product includes prebiotic, probiotic, and micronutrients Probiotics 1512 are live microorganisms that are intended to have health benefits when consumed or applied to the body. Prebiotics 1514 are special plant fibers that help healthy bacteria grow in the gut, making the digestive system work better. The prebiotic may include green banana flour. The micronutrients 1516 may include selenium, zinc, and magnesium.

Although people often think of bacteria and other microorganisms as harmful "germs," many are actually helpful. Some bacteria in the gut play a critical role in the body's immune system. Many of the microorganisms in probiotic products are the same as or similar to microorganisms that naturally live in our bodies.

The ingredients may optionally include N-acetyl cysteine (NAC), quercetin, nattokinase, vitamin C, fucoidan, and N-acetyl glucosamine (NAG) 1518. At step 1520, the process markets the consumable product as facilitating the activation of gut microbiome induced CMHI and supplies directions for using and consuming the consumable product. At step 1530, the process activates the CMHI in the group of people automatically based on following the directions for usage and consumption of the consumable product. At step 1540, the process targets the usage of the consumable product by facilities selected from a group consisting of schools, prisons, jails, group homes, residential treatment centers, nursing homes, assisted living centers, factories, offices, hospitals, cruise ships, and senior residential facilities. FIG. 15 processing thereafter ends at 1550.

FIG. 16 shows the steps for restoring and maintaining a healthful gut microbiome 1600. At step 1610, the process provides a protocol for restoring gut microbiome. The protocol includes a daily consumption of a consumable product received in a form of a powder to be ingested by a group of people. The consumable product includes select prebiotics, probiotics, and non-pharmaceutical phytochemicals which may be delivered in a smoothie utilizing the powder for administration to a group of people in institutional settings, such as, schools, nursing homes, factories, prisons, etc. Consumption by the group of people results in gut microbiome induced CMHI. The non-pharmaceutical phytochemicals include properties selected from a group consisting of anti-cancer, neuroprotection, antioxidant, anti-prion, anti-amyloid, mitochondrial rehabilitation, and autophagy 1605. The consumable product may include N-acetyl cysteine (NAC), nattokinase, N-acetyl glucosamine (NAG), prebiotic including green banana, probiotic, and micronutrients. The consumable product may be included in a smoothie. Consumption of the smoothie by a group of people results in gut microbiome induced CMHI.

FIG. 17 shows the steps taken by a process that facilitates activation of antiviral priming induced Cell-mediated Herd Immunity (CMHI) by activating antiviral induced individual cell-mediated immunity (CMI) for long term usage 1700. The Antiviral Priming Daily Supplement is intended to be taken daily and facilitates Antiviral Priming CMHI. Like the Viral Fire Extinguisher, this product is designed to overcome the problems of bioavailability by using a nanotechnology delivery system to facilitate bio absorption of otherwise poorly absorbed phytochemicals taken orally. This product emulates what has been seen in African countries with the lowest rates of Covid in the world. A significant percentage of the population in these countries have background levels of anti-parasite and antimalarial medications in their bloodstreams at all times. These medications also have enzyme blocking characteristics that inhibit viral replication. The Antiviral Priming Daily Supplement helps mitigate the ever present risk of new bioweapons, the increasing incidence of ADHD in young populations, cancer, neurodegenerative diseases, heart disease, strokes, autoimmune diseases caused by widespread spike protein endothelial disease and widespread impairment of cell-mediated immunity.

At step 1710, the process manufactures a consumable product in a form of an ingestible cream delivered orally with nanotechnology enhanced bioavailability and sealed in an oxygen proof sachet wherein the consumable product includes non-pharmaceutical phytochemicals with intrinsic biomolecular properties that inhibit enzymes critical to viral replication. The non-pharmaceutical nutraceuticals may include curcumin, quercetin, and boswellic acid 1712. The non-pharmaceutical nutraceuticals optionally include artemisinin, berberine, hesperidin, luteolin, bacopa, fisetin, silymarin, taurine, and bromelain 1714. The non-pharmaceutical nutraceuticals include properties selected from a group consisting of anti-cancer, neuroprotection, antioxidant, anti-prion, anti-amyloid, mitochondrial rehabilitation, anti-spike protein, and autophagy 1716. At step 1720, the process markets the consumable product for the activation of the antiviral priming induced CMHI in the group of people with directions for using and consuming the consumable product. At step 1730, the process activates the antiviral priming induced CMHI in the group of people automatically based on following the directions for usage and consumption of the consumable product. At step 1740, the marketing targets facilities for example, but limited to schools, prisons, jails, group homes, residential treatment centers, nursing homes, assisted living centers, factories, offices, hospitals, cruise ships, senior residential facilities, and the like. FIG. 17 processing thereafter ends at 1750.

Figure 18:
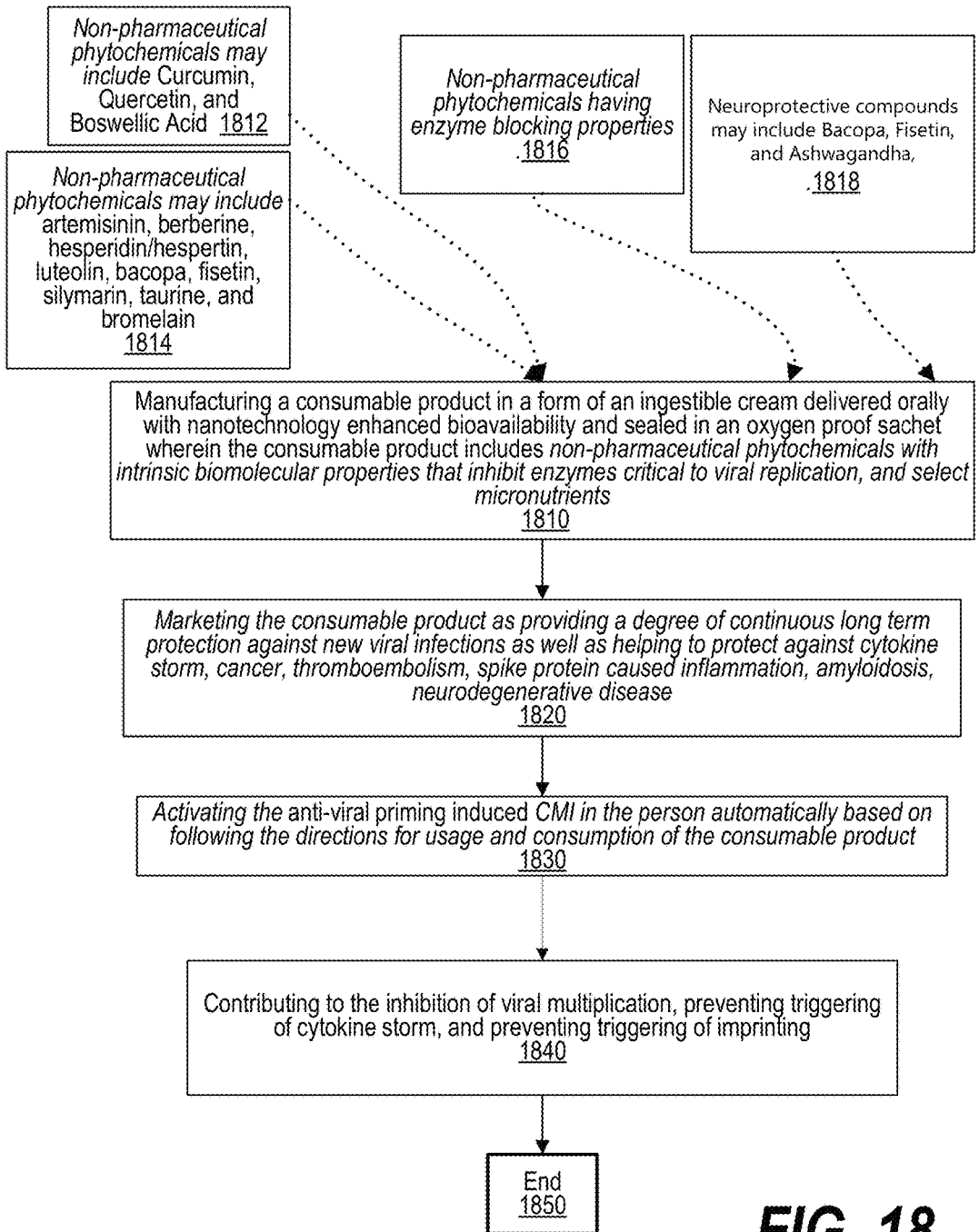
Figure 19:
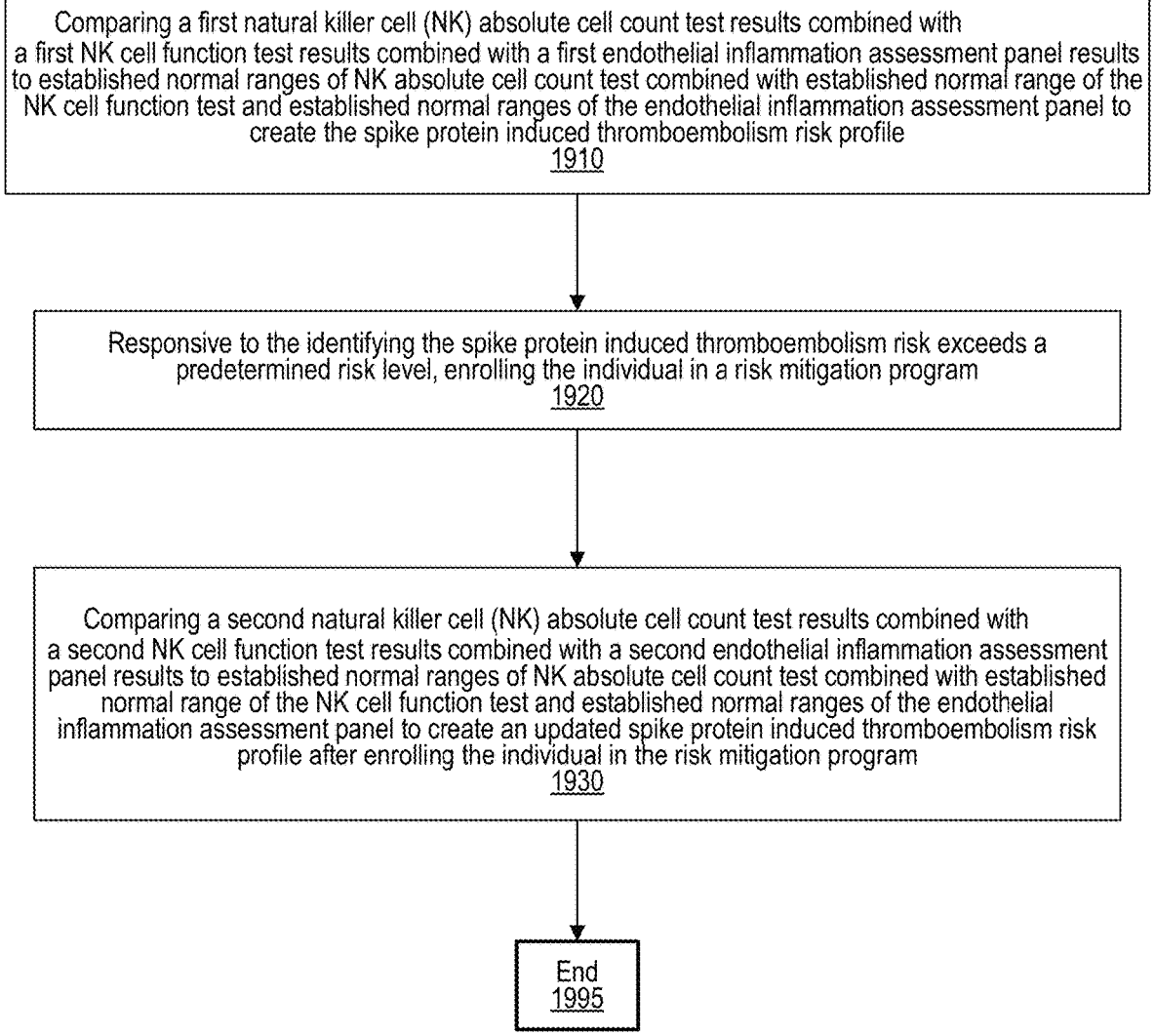
Figure 20:
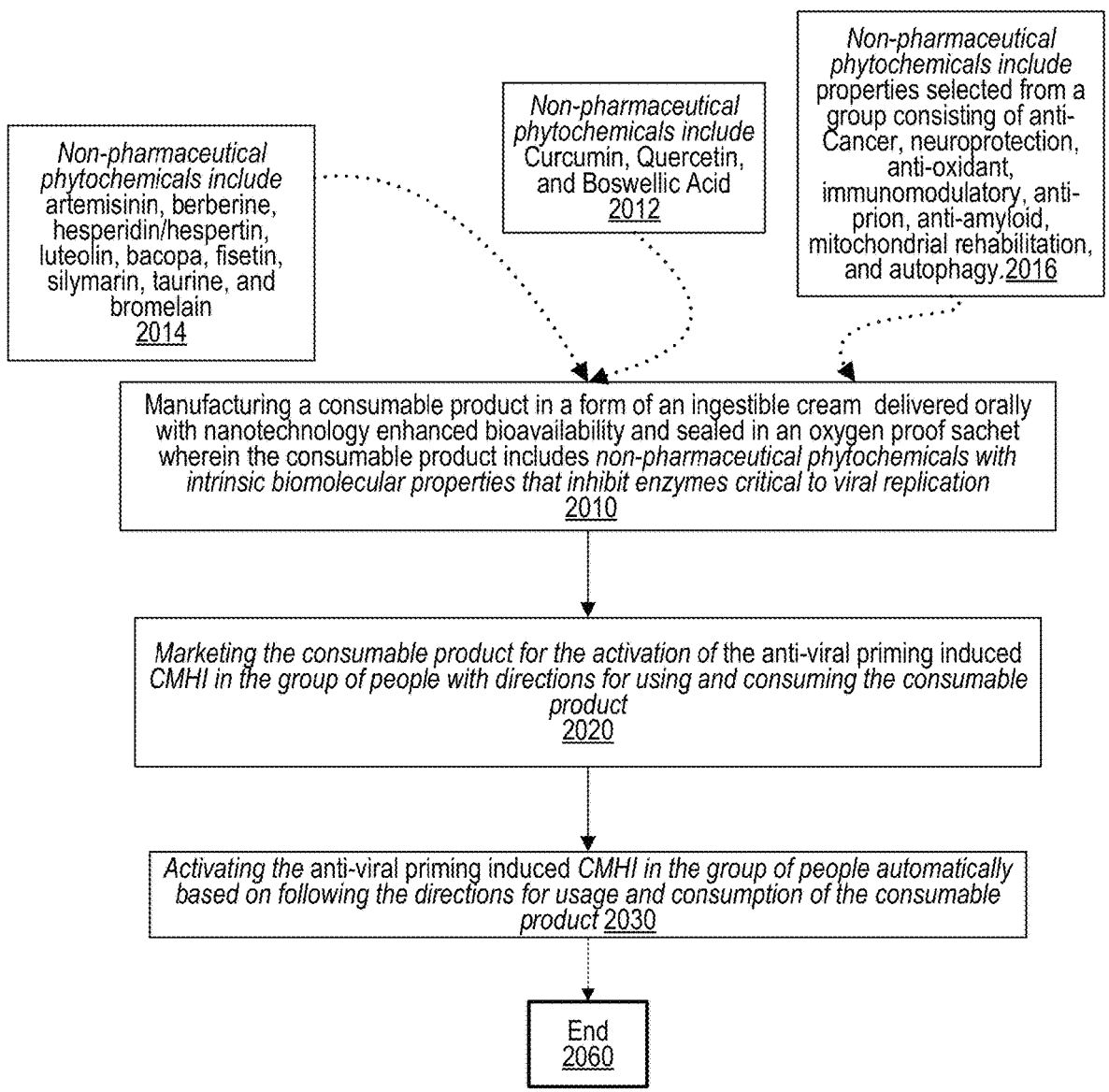
Figure 21:
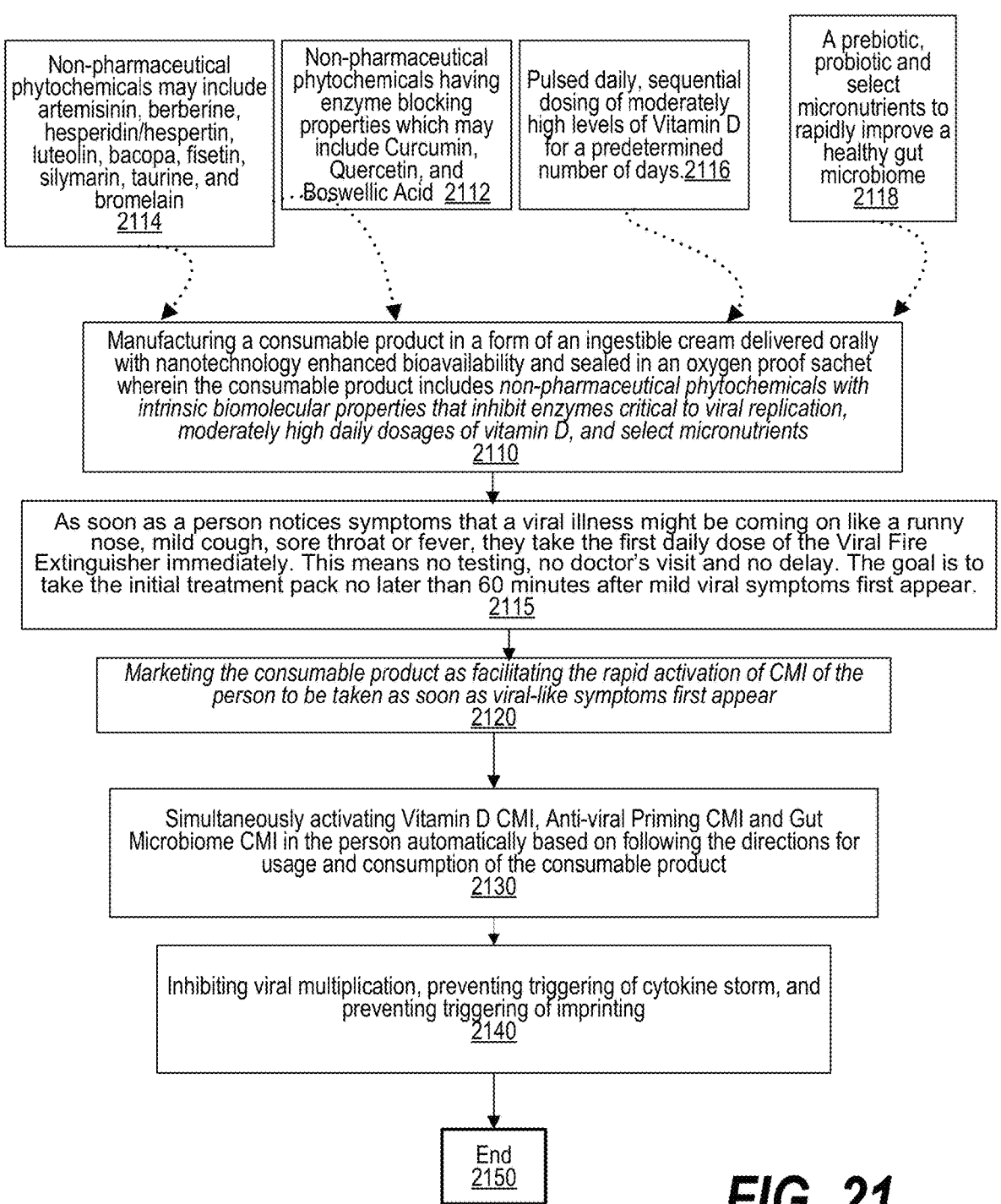

FIG. 18 shows the steps taken for antiviral priming 1800. At step 1810, the process provides a consumable daily pack contents to a group of people. The consumable daily pack includes contents that inhibit enzymes that promote viral replication to achieve antiviral priming induced CMHI.

At step 1810, a consumable product is manufactured in a form of an ingestible cream delivered orally with nanotechnology enhanced bioavailability and sealed in an oxygen proof sachet wherein the consumable product includes non-pharmaceutical phytochemicals with intrinsic biomolecular properties that inhibit enzymes critical to viral replication.

Figure 22:
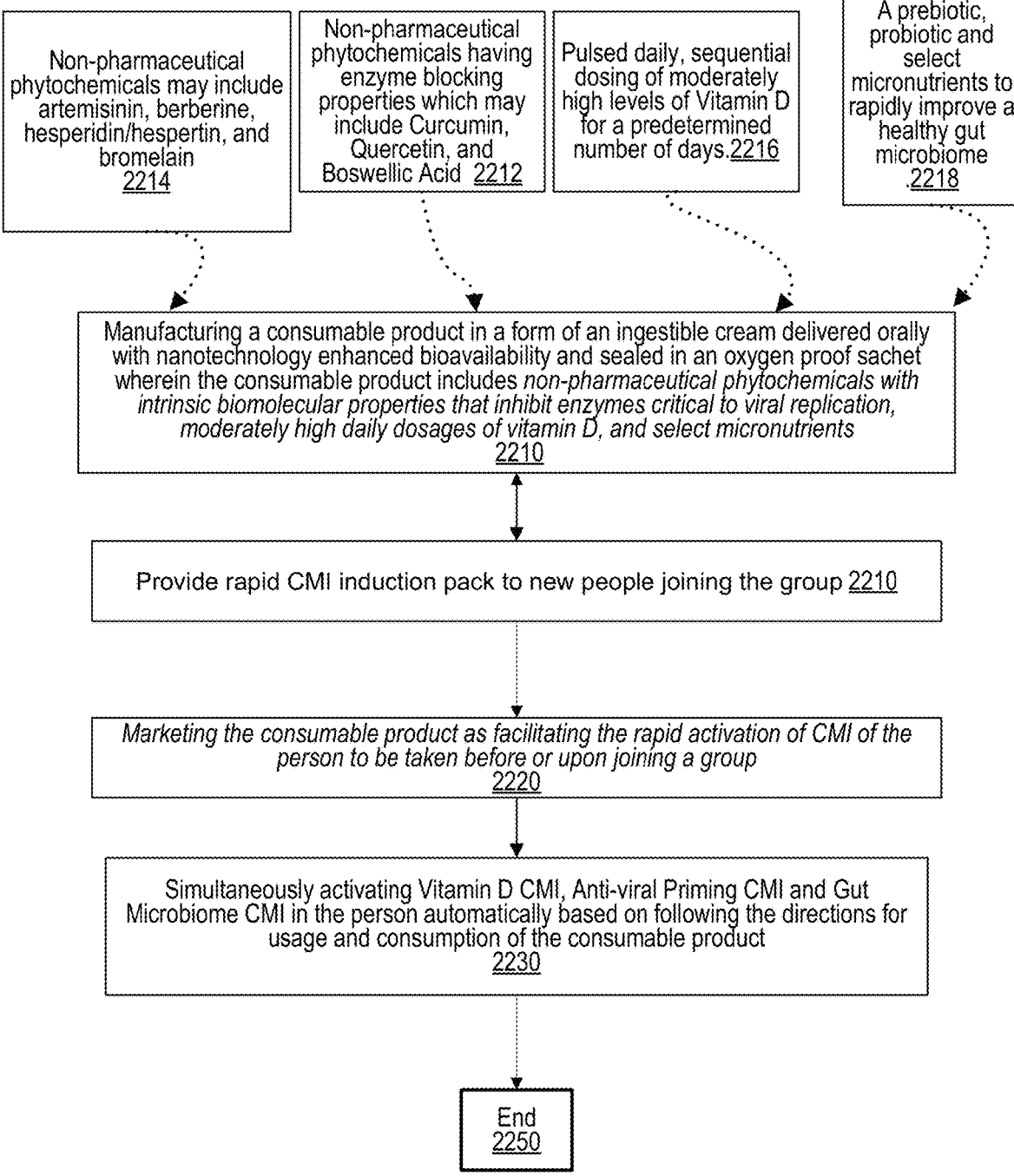

The consumable product is designed for long term daily usage and includes neuroprotective compounds to help reduce or prevent cognitive impairment. An objective for including contents in an embodiment for manufacturing the product for long term daily usage is to bundle in compounds that provide the most benefit with the least cost to be consumed by a group of people. At step 1814, non-pharmaceutical nutraceuticals may include artemisinin, berberine, hesperidin, luteolin, bacopa, fisetin, silymarin, taurine, and bromelain. The non-pharmaceutical nutraceuticals may include curcumin, quercetin, and boswellic acid 1812. The non-pharmaceutical nutraceuticals may include properties selected from a group consisting of anti-cancer, neuroprotection, immunomodulatory, antioxidant, anti-prion, anti-amyloid, mitochondrial rehabilitation, and autophagy 1816. The neuro protective compounds may include Bacopa, Fisetin, Ashwaghanda, Luteolin, Butcher's Brew, Feverfew, Ginko *Biloba*, Lions Mane, Lutein, vitamin K, *spirulina*, lactoferrin, vitamin A, and Zeaxanthin 1818. At step 1820, the process markets the consumable product as providing a degree of continuous long term protection against new viral infections as well as helping to protect against cytokine storm, cancer, thromboembolism, spike protein caused inflammation, amyloidosis, neurodegenerative disease. At step 1830, the process activates the antiviral priming induced CMHI in the group of people automatically based on following the directions for usage and consumption of the consumable product. At step 1840, consumption of the product contributes to the inhibition of viral multiplication, preventing triggering of cytokine storm, and preventing triggering of imprinting. FIG. 18 processing thereafter ends at 1850.

FIG. 19 shows the steps taken to assess spike protein induced thromboembolism risk in an individual 1900. At step 1910, the process compares a first natural killer cell (NK) absolute cell count test results combined with a first NK cell function test results combined with a first endothelial inflammation assessment panel results to established normal ranges of NK absolute cell count test combined with established normal range of the NK cell function test and established normal ranges of the endothelial inflammation assessment panel to create the spike protein induced thromboembolism risk profile. At step 1920, responsive to identifying the spike protein induced thromboembolism risk profile exceeds a predetermined risk level, enrolling the individual in a risk mitigation program. At step 1930, the process compares a second natural killer cell (NK) absolute cell count test results combined with a second NK cell function test results combined with a second endothelial inflammation assessment panel results to established normal ranges of NK absolute cell count test combined with established normal range of the NK cell function test and established normal ranges of the endothelial inflammation assessment panel to create an updated spike protein induced thromboembolism risk profile after enrolling the individual in the risk mitigation program. If the results of the test are in the established normal range, the risk mitigation program is considered successful for the treated individual. FIG. 19 processing thereafter ends at 1995.

FIG. 20 shows the steps taken to facilitate activation of antiviral priming induced Cell-mediated Herd Immunity (CMHI) by activating antiviral induced individual cell-mediated immunity (CMI) for short term usage 2000. At step 2010, a consumable product is manufactured in a form of an ingestible cream delivered orally with nanotechnology enhanced bioavailability and sealed in an oxygen proof sachet wherein the consumable product includes non-pharmaceutical phytochemicals with intrinsic biomolecular properties that inhibit enzymes critical to viral replication. At step 2014, non-pharmaceutical nutraceuticals include artemisinin, berberine, hesperidin, luteolin, bacopa, fisetin, silymarin, taurine, and bromelain. The non-pharmaceutical nutraceuticals include curcumin, quercetin, and boswellic acid 2012. The non-pharmaceutical nutraceuticals may include properties selected from a group consisting of anti-cancer, neuroprotection, immunomodulatory, antioxidant, anti-prion, anti-amyloid, mitochondrial rehabilitation, and autophagy 2016. At step 2020, the process markets the consumable product for the activation of the antiviral priming induced CMHI in the group of people with directions for using and consuming the consumable product. At step 2030, the process activates the antiviral priming induced CMHI in the group of people automatically based on following the directions for usage and consumption of the consumable product. FIG. 20 processing thereafter ends at 2060.

FIG. 21 shows the steps taken for immediate treatment of a person with initial viral symptoms by rapidly activating individual cell-mediated immunity (CMI) 2100. At step 2110, the process manufactures a consumable product in a form of an ingestible cream delivered orally with nanotechnology enhanced bioavailability and sealed in an oxygen proof sachet wherein the consumable product includes non-pharmaceutical phytochemicals with intrinsic biomolecular properties that inhibit enzymes critical to viral replication, moderately high daily doses of vitamin D, and select micronutrients. The non-pharmaceutical nutraceuticals may include artemisinin, berberine, hesperidin, luteolin, bacopa, fisetin, silymarin, taurine, *spirulina*, vitamin A, lactoferrin, vitamin C and resveratrol, and bromelain 2114. The non-pharmaceutical nutraceuticals may include curcumin, quercetin, and boswellic acid 2112. The non-pharmaceutical nutraceuticals have enzyme blocking and immunomodulatory properties 2116 and may include pulsed daily, sequential dosing of moderately high levels of Vitamin D for a predetermined number of days. The product may include a prebiotic, a probiotic and select micronutrients to rapidly improve a healthy gut microbiome 2118. At step 2120, the process markets the consumable product as facilitating the rapid activation of CMI of the person taking the consumable product as soon as viral infection symptoms occur. As soon as a person notices symptoms that a viral illness might be coming on like a runny nose, mild cough, sore throat or fever, they take the first daily dose of the Viral Fire Extinguisher immediately 2115. This means no testing, no doctor's visit and no delay. The goal is to take the initial treatment pack no later than 60 minutes after mild viral symptoms first appear. At step 2130, the process simultaneously activates vitamin D CMI, antiviral priming CMI and gut microbiome CMI in the person automatically based on following the directions for usage and consumption of the consumable product the antiviral priming induced CMI in the person automatically based on following the directions for usage and consumption of the consumable product. At step 2140, the process helps inhibit viral multiplication, prevents triggering of cytokine storm, and prevents triggering of imprinting. FIG. 21 processing thereafter ends at 2150. FIG. 22 shows the steps for using a viral prevention packs 2200. At step 2210, a consumable product is manufactured in a form of an ingestible cream delivered orally with nanotechnology enhanced bioavailability and sealed in an oxygen proof sachet wherein the consumable product includes non-pharmaceutical phytochemicals with intrinsic biomolecular properties that inhibit enzymes critical to viral replication. The consumable product is designed for short term daily usage intended to quickly activate the three elements of their personal CMI to contribute to CMHI for the health of the group. The prevention packs jumpstart the three forms of individual CMI that must be switched on before people enter a group indoors and which are key to CMHI. The product may include the non-pharmaceutical nutraceuticals may include artemisinin, berberine, hesperidin, luteolin, bacopa, fisetin, silymarin, taurine, and bromelain 2214. The non-pharmaceutical nutraceuticals may include curcumin, quercetin, and boswellic acid 2212. The non-pharmaceutical nutraceuticals have enzyme blocking and immunomodulatory properties 2216 and may include pulsed daily, sequential dosing of moderately high levels of Vitamin D for a predetermined number of days. The product may include a prebiotic, a probiotic and select micronutrients to rapidly improve a healthy gut microbiome 2218. At step 2215, the process provides a rapid CMI induction pack to new people joining the group to achieve antiviral priming induced CMHI. At step 2220, the consumable product is marketed as facilitating the rapid activation of CMI to each person to be taken before or upon joining the group. At step 2230, the consumption of the product simultaneously activates vitamin D CMI, antiviral priming CMI and gut microbiome CMI in the person automatically based on following the directions for usage and consumption of the consumable product. FIG. 22 processing thereafter ends at 2250.

FIG. 23 shows the steps taken by a process for assessing and mitigating risk of spike protein induced immune suppression and endothelial inflammation 2300. At step 2305, the process provides a user interface supporting interactive communication with an automated system that accesses a HIPAA compliant database. At step 2310, the process applies a first blood extraction procedure to a plurality of people to form a first set of blood vials. At step 2315, the process sends the first set of blood vials for analysis associated with natural killer cell (NK) absolute cell count test combined with NK cell function test combined with an endothelial inflammation assessment panel. At step 2320, the process receives a first set of results from the sending of the first set of blood vials. At step 2325, the process compares the first set of results to established normal ranges to create the spike protein induced immune suppression and endothelial inflammation risk profile in the plurality of people. The panels may include, for example, but not limited to Insulin Resistance Panel, Lipoprotein-associated phospholipase A2 Activity, Asymmetric dimethylarginine and Symmetric dimethylarginine, Myeloperoxidase, F2-Isoprostane/Creatinine Ratio, Oxidized low-density lipoprotein, Microalbumin, and Highly Sensitive C reactive protein.

At step 2330, the process offers, by the user interface, a first group of people having the spike protein induced immune suppression and endothelial inflammation risk profile exceeding predetermined established normal ranges, a risk mitigation program. At step 2335, the process enrolls each individual in the first group of people accepting the offered risk mitigation program in the risk mitigation program to form a group of risk mitigation enrolled people. At step 2340, the process applies a second mass blood extraction procedure to the group of risk mitigation enrolled people to form a second set of blood vials. At step 2345, the process sends the second set of blood vials for analysis associated with natural killer cell (NK) absolute cell count test combined with NK cell function test combined with an endothelial inflammation assessment panel. At step 2350, the process receives a second set of results from the sending of the second set of blood vials. At step 2355, the process compares the second set of results to established normal ranges to form an updated immune suppression and endothelial inflammation risk profile in the group of risk mitigation enrolled people. At step 2360, the process assesses the risk mitigation program as effective when the updated spike protein induced immune suppression and endothelial inflammation risk profile does not exceed the predetermined risk level. At step 2370, when the process assesses the risk mitigation program as not effective for an individual, that is, when the updated spike protein induced immune suppression and endothelial inflammation risk profile exceeds the predetermined risk level, the risk mitigation program may be adjusted or adapted for the person and after followed for some period of time retested. FIG. 23 processing thereafter ends at 2365.

Figure 24:
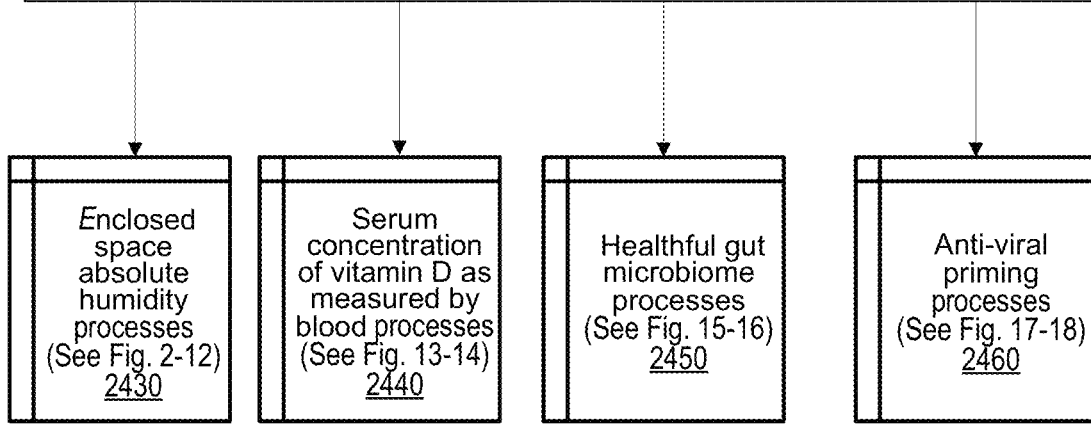

FIG. 24 shows the steps taken by a company-specific viral safety certification program 2400. At step 2420, the process monitors, by an independent auditor, compliance of an implementation of four key interventions required to achieve Cell-mediated Herd Immunity (CMHI) by the company and wherein the four key interventions are enclosed space absolute humidity, serum concentration of vitamin D as measured by a blood test, healthful gut microbiome, and antiviral priming in individuals to determine a compliance assessment. Assessing, by the independent auditor, compliance levels associated with the four key interventions. Issuing the company-specific viral safety certification, by the independent auditor, based on the compliance assessment reaching a predetermined level of compliance. At predefined process 2430, the process performs the enclosed space absolute humidity routines (see FIG. 2-12 and corresponding text for processing details). At predefined process 2440, the process performs the serum concentration of vitamin D as measured by blood processes routines (see FIG. 13-14 and corresponding text for processing details). At predefined process 2450, the process performs the healthful gut microbiome processes routines (see FIG. 15-16 and corresponding text for processing details). At predefined process 2460, the process performs the antiviral priming processes routines (see FIG. 17-18 and corresponding text for processing details).

FIG. 25 shows the steps taken by a process that recruits, credentials, onboards, and trains qualified service providers supporting CMHI for community health 2500. At step 2502, the process receives endorsement of community leaders, based on promoting community service to address urgent public health needs, facilitating cooperation from college and technical school officials to share alumni lists of selected occupations for recruitment of registry applicants. At step 2505, the process recruits potential service providers to apply to become part of a registry of qualified service providers targeted toward services that facilitate CMHI. At step 2510, the process vets a set of service provider applicants according to an acceptance criteria to classifying each service provider applicant in the set of service provider applicants as one of invited to apply, added to a stand-by list for future application, and not invited. At step 2515, the process credentials applicants invited to submit applications to become members of the registry. At step 2520, the process onboards the credentialed applicants. At step 2525, the process trains the onboarded applicants. At step 2530, the process adds the trained applicants to the registry. A first service is drawing blood and the alumni list includes phlebotomists, certified nurse assistants (CNA), respiratory therapists, paramedics, medical technologists, nurses (LVN/RN) 2540. At step 2550, when a testing event occurs or a work opportunity is available, each member of the registry qualified to participate is eligible to sign up for shifts for work opportunities. A second services is collecting data pertaining to adapting existing heating, ventilation, and air conditioning (HVAC) systems to achieving a safe absolute humidity level and the alumni list includes HVAC technicians and mechanical engineers 2555. At step 2560, collection of HVAC data is scheduled for a plurality of buildings and each member of the registry is eligible to sign up for a shift for the collecting of the HVAC data according to a schedule. FIG. 25 processing thereafter ends at 2565.

FIG. 26 shows the steps taken to reduce company insurance premiums 2600. At step 2605, an independent auditor establishes a company-specific risk profile including wellness and safety data. At step 2610, the process compares the company-specific risk profile to an aggregate pool of risk data derived from many companies to form a company-specific risk reduction assessment. At step 2620, the process certifies the company-specific risk reduction assessment, by the independent auditor, to qualify for lower insurance rates [disability, health, group life, worker's compensation, etc.]. At step 2625, the wellness and safety data include, but are not limited to, workforce and premise liability aspects selected from a group consisting of outbreaks, accidents, injuries, chronic illness affecting workforce [e.g., workforce productivity and absenteeism], and deaths. At step 2635, the process compensates for increased introduced risk data starting in 2021 including workforce absenteeism, disability, and excess mortality. At step 2640, the process improves the company-specific risk profile via industry specific CMHI risk management protocols and interventions. At step 2650, the process applies interventions which include enclosed space absolute humidity, serum concentration of vitamin D as measured by a blood test, healthful gut microbiome, and antiviral priming. At step 2655, the process validates results of the company-specific risk reduction assessment by an independent auditor separate from a viral safety company. At step 2660, company-specific risk profile data may be collected and processed automatically and periodically, for example, weekly. At step 2665, comparing company-specific risk profile metrics after following industry specific CMHI risk management protocols and interventions to other comparable industries which operate without the industry specific CMHI risk management protocols and interventions to establish the company-specific risk reduction assessment (can further validate company-specific risk profile using that company's previous risk profile history). FIG. 26 processing thereafter ends at 2670.

Figure 27:
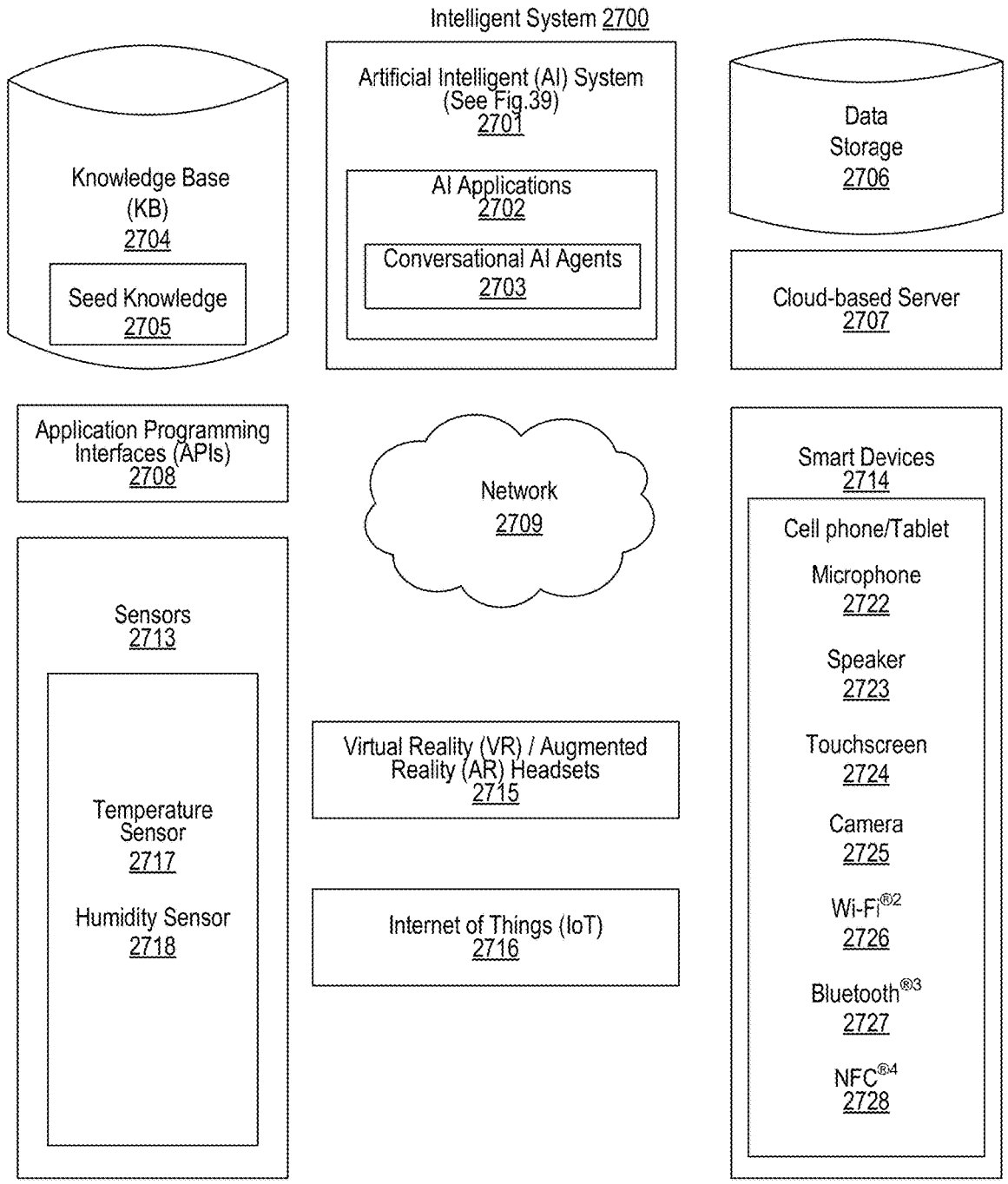

FIG. 27 depicts a high-level schematic representation of an intelligent system 2700 designed for facilitating contextually relevant conversational interactions.

The intelligent system 2700 is a complex network of various technologies and components that work together to provide user-centered, contextually relevant, and personalized interactions. The intelligent system 2700 comprises an AI system 2701 (see FIG. 28 and corresponding text), a Knowledge Base (KB) 2704, and AI applications 2702, which can be conversational AI agents 2703.

The intelligent system 2700 also includes data storage 2706, cloud-based server 2707, application programming interfaces (APIs) 2708, and network 2709. The data storage 2706 stores and manages the vast amounts of data generated by the AI system 2701. The cloud-based server 2707 manages the processing and storage of data and provides computing power to enable the AI application to function. The network 2709 connects the various components and allows for communication between them.

The AI system 2701 can also integrate with various sensors 2713, smart devices 2714, virtual reality (VR)/ augmented reality (AR) headsets 2715, and Internet of Things (IOT) 2716. To obtain contextual information about the environment, the system can use a range of sensors, including temperature sensor 2717, humidity sensor 2718. This information is then preprocessed and categorized before being displayed to users.

Moreover, smart devices 2714 come equipped with various features such as microphones 2722, speakers 2723, touchscreens 2724, cameras 2725, Wi-Fi 2726, Bluetooth®[11] 2727, and near field communications (NFC®[12]) 2728. These features enable the AI system to gather contextual information about the user's environment and interactions, allowing it to provide more personalized and relevant responses. For instance, the microphone can capture the user's voice input, while the camera can capture visual data such as facial expressions or object recognition.

The integration of various sensors 2713 and smart devices 2714 allows the AI system 2701 to gather and analyze data from multiple sources, thereby enabling it to detect contextual information about the environment. This, in turn, provides a more relevant and personalized user experience. The AI system 2701 can respond to user inputs and environmental changes through AI applications, creating a seamless and integrated user experience. By harnessing the power of virtual and augmented reality 2715, as well as the Internet of Things (IOT) 2716 devices, the AI system 2701 can further enhance its capability to detect and respond to user needs and preferences.

[11]Bluetooth is a trademark of Bluetooth SIG, Inc.
[12]NFC is a trademark of Never Fame Over Currency, LLC.

Referring to FIG. 27, the KB 2704 is a structured system, but not limited to a database, a set of databases, a repository, a set of repositories, and the like, which stores distinct types of data and diverse types of information that the AI system can access and use to provide contextually relevant and personalized responses.

The KB 2704 also manages information about the users. The information can be manually entered or automatically extracted from text, images, or other sources. The KB 2704 supports various applications such as object recognition, NLP, and decision making. The data and information stored in KB 2704 can be organized into categories, such as user properties, user attributes, user relations with the associated conversational AI agents 2703.

There are three main categories of data stored in the KB 2704. The first category is user attributes, which pertain to the physical characteristics demographic data that the AI system 2701 can utilize to interact with the users. The second category, environment data, pertains to the physical conditions in the environment, such as temperature, humidity, lighting, and other relevant factors, as well as the physical layout of the environment, including the location of doors, windows, and furniture. The third category is interaction data, which encompasses details about the user's preferences, previous interactions, and other relevant information.

User preferences may include information about their likes, dislikes, and other personal preferences that can be used to personalize the user's experience with the AI system. For example, if a user has expressed a preference for a particular type of music, the AI system can store this preference in the KB. The system can then use this information to recommend similar music or create a playlist based on the user's preferences. If the user previously interacted with the AI system and provided feedback on their experience, this information can also be stored in the KB. This information can be utilized to improve future interactions.

The AI system collects and stores data about the user's interactions with the system in the KB. By leveraging the data stored in the KB, the AI system can adapt to the user's preferences and behavior, creating a more seamless and intuitive conversational interaction. This personalized approach helps to build trust and engagement between the user and the AI system, leading to a positive user experience.

To add human-AI interaction data to the KB, the AI system initially processes the data to extract significant information such as user intents, behaviors, and preferences. This processing often involves using NLP techniques to parse the conversation and identify the essential elements. After the data has been processed, it is added to the KB in a structured format that is easily accessible and analyzed by the AI system. This format can include relevant contextual information such as the time and location of the interaction, the user's input, and the AI system's response.

Furthermore, the AI system may employ ML algorithms to analyze the interaction data and identify patterns and trends in the user's behavior and preferences. This analysis can then be used to refine the AI system's understanding of the user and improve its ability to produce personalized, contextually relevant responses. For instance, if the user frequently requests recommendations for local restaurants, the AI system can use this data to personalize future recommendations based on the user's past preferences and feedback. Using this approach, the AI system can provide contextually relevant and personalized recommendations, improving the overall user experience.

One important aspect of AI systems is their ability to integrate different data categories to gain a comprehensive understanding of the user's context and needs. This allows for user-centered, contextually relevant, and personalized conversational interaction. For example, the AI system can use the user's preferences and environment data to recommend activities or products suited to current conditions.

The KB can be updated manually or automatically depending on the specific implementation of the AI system. Manual updating of the KB typically involves human intervention, such as clients, a system administrator, or a data analyst adding or modifying information in the KB. This may be done through a user interface specifically designed for managing the KB, or through an API that allows direct programmatic access to the KB.

In the context of AI systems and software development, a client typically refers to an individual or organization that uses or purchases a product or service. The client may have specific requirements or expectations for the product or service, and they may provide feedback or input to the developers or providers to improve the product or service. In the case of an AI system, the client may be a business or individual who uses the system to perform tasks or gain insights. Typically, clients would not have direct access to update the KB themselves as it is a critical component of the AI system and requires specialized knowledge and expertise.

However, clients can indirectly update the KB by providing feedback and interacting with the AI system. For example, if a client's customized AI application is stored in the KB, the AI system can use the client's past interactions with the system to learn and update the KB accordingly. If the client provides feedback on their experience or preferences, this information can be used to adjust the AI system's understanding and improve its ability to provide relevant and personalized recommendations.

Additionally, in some cases, clients may have the ability to indirectly update the KB through a user interface or dashboard provided by the AI system. This interface may allow the client to adjust certain settings or preferences that can be stored in the KB and used to inform the AI system's responses and recommendations.

On the other hand, automatic updating of the KB occurs in real-time through the use of ML algorithms or other automated techniques. For example, an AI system may continuously monitor user interactions and automatically update the KB with added information learned from those interactions. The AI system may use natural language processing algorithms to extract relevant information from user inputs and use this information to update the KB in real-time.

One way that an AI system can identify added information from continuously monitoring user interactions is through ML algorithms. These algorithms can analyze substantial amounts of data from user interactions and identify patterns and trends that can be used to update the KB.

For example, the AI system is used to provide ensure all employees are participating in a company-specific CMHI risk management protocol. As users interact with the AI system and ask questions, the AI system can learn from these interactions and update its understanding of the types of questions being asked and the most appropriate responses to provide. The AI system can then use this updated information to improve future interactions and provide better support.

The AI system identifies relevant information through various techniques, such as natural language processing, data mining, and ML algorithms. Once the system has identified the relevant information, it processes the data to extract key insights and patterns that can be used to update the KB.

The process of updating the KB involves several steps. First, the AI system analyzes the new data to determine its relevance and significance to the existing knowledge base. The system then updates the KB with the added information, either by adding new entities or relationships or modifying existing ones.

To ensure the accuracy and reliability of the updated knowledge, the AI system may use techniques such as data validation and error correction. The system may also employ techniques such as differential privacy to protect sensitive information while still allowing meaningful insights to be drawn. Once the KB has been updated, the AI system can use the new knowledge to improve its performance in various tasks such as decision-making, natural language understanding, and predictive analytics. The updated KB allows the system to adapt to new situations and better understand user needs and preferences, leading to more accurate and personalized interactions.

To update the KB in real-time, the AI system can use automated processes that analyze and integrate added information as it is received. For instance, the AI system can be programmed to automatically update the KB when it detects new patterns or trends in user interactions.

Moreover, the AI system can utilize automated techniques to analyze data from diverse sources, such as social media, news feeds, and weather forecasts, to incorporate added information into the KB. For example, if the weather forecast predicts rain at a specific location, the AI system can access weather APIs to update the KB with this information. By integrating this updated data, the AI system can offer contextually relevant recommendations or actions to the user based on the current situation.

In one embodiment, a user interacts with a conversational AI agent through a shared ride driver's business card to request a ride from their current location to a testing destination. The conversational AI agent can use this interaction to update the KB, adjusting the user's preferences and attributes, such as their preferred car type, driver rating, and price range.

The iterative process can also help improve the accuracy of the relationship between the user and their past ride experiences, as well as the relationship between the user and other ride options in the area. For example, if the user has previously requested rides to a certain location during specific times of the day, the AI system can use this data to provide more accurate and relevant ride options in the future. The AI system can also analyze data from other sources, such as traffic patterns, weather conditions, and driver availability, to provide contextually relevant recommendations and adjust ride options accordingly.

In the described intelligent system 2700, the KB 2704 contains seed knowledge 2705 to establish and expand the KB. This initial set of information, data, or domain knowledge can include known facts, rules, relationships, and information about the environment that the AI system interacts with domain knowledge refers to the specialized understanding, insights, and expertise related to a specific area or field.

Additionally, domain knowledge can be contributed by a variety of sources, including subject matter experts, industry professionals, users, and other stakeholders. Users can also contribute domain knowledge through their interactions with the AI system. For example, a user could provide feedback on their preferences or experiences, which the AI system can then use to improve its responses and understand the user's needs.

An AI application can contribute domain knowledge to some extent, depending on the type and scope of the application. For example, an AI system that is designed to learn and improve over time, such as a ML system, can contribute to its own domain knowledge by analyzing data, detecting patterns and trends, and adjusting its responses accordingly.

Furthermore, an AI application that is designed to analyze and interpret substantial amounts of data, such as a predictive analytics system, can contribute domain knowledge by identifying correlations and making predictions based on its analysis.

In the development of the KB, domain knowledge serves as a solid foundation for the AI system to build upon. This foundation consists of relevant concepts, relationships, and rules specific to the domain. By incorporating domain knowledge as seed knowledge 2705, the AI system can start with a robust understanding of the subject matter, enabling it to generate accurate and contextually relevant responses. The AI system has mechanisms to gather, organize, and integrate this knowledge into the KB.

As the AI system interacts with users and acquires additional information, it can refine and expand its KB. During the training process, the seed knowledge is provided to a ML model, which enables it to learn and improve based on the initial data. By combining the seed knowledge 2705 with newly acquired data, the AI system becomes more proficient in its domain, improving its ability to provide meaningful and accurate responses, recommendations, or solutions.

Referring to FIG. 27, AI applications 2702 are specific implementations of the AI system designed to solve particular problems or perform specific tasks within a domain. These applications leverage the capabilities of the underlying AI system 2701 to provide tailored solutions for various industries and use cases. The relationship between an AI system and AI applications can be understood as a hierarchical structure where the AI system serves as the underlying foundation, and AI applications are built upon that foundation to provide specific functionalities and solutions.

In some embodiments, the AI application can be integrated with various smart devices and systems in a public service facility, such as a library or a government building. By accessing the data and functionality of other smart devices and systems, the AI application can provide an integrated user experience that is tailored to an individual's needs and preferences.

For instance, the AI application can integrate with sensors that detect the number of people present in the building and their locations, as well as with the building's HVAC system to regulate temperature, airflow, and absolute humidity. Using NLP and ML, the AI application can understand the preferences and behavior of visitors to the facility.

In some instances, AI applications manifest as conversational AI agents designed to interact with users through dynamic communication while simultaneously learning and adapting. By incorporating user feedback and interaction, these agents consistently improve their precision and effectiveness.

In an embodiment, an AI application 2702 running on a mobile device offers an intuitive interface that presents the gathered environment data in an accessible format for users. Environment data includes information about the environment surrounding the user, such as temperature, humidity, and lighting conditions, which can be used to provide more relevant and accurate responses. Besides showing the environment data, these devices also generate recommendations and suggestions derived from the collected information. For instance, if the AI application detects a low humidity in the user's surroundings and identifies that user is indoor, the AI application might advise the user to leave the premises by sending a push notification through the mobile device or in some environment the AI application may be able to turn on the humidify that is located near the user.

Referring to FIG. 27, the AI system 2701 (See FIG. 28) serves as the principal component of the intelligent system, employing a range of techniques like NLP, ML, and advanced reasoning to predict user intents and objectives.

Figure 28:
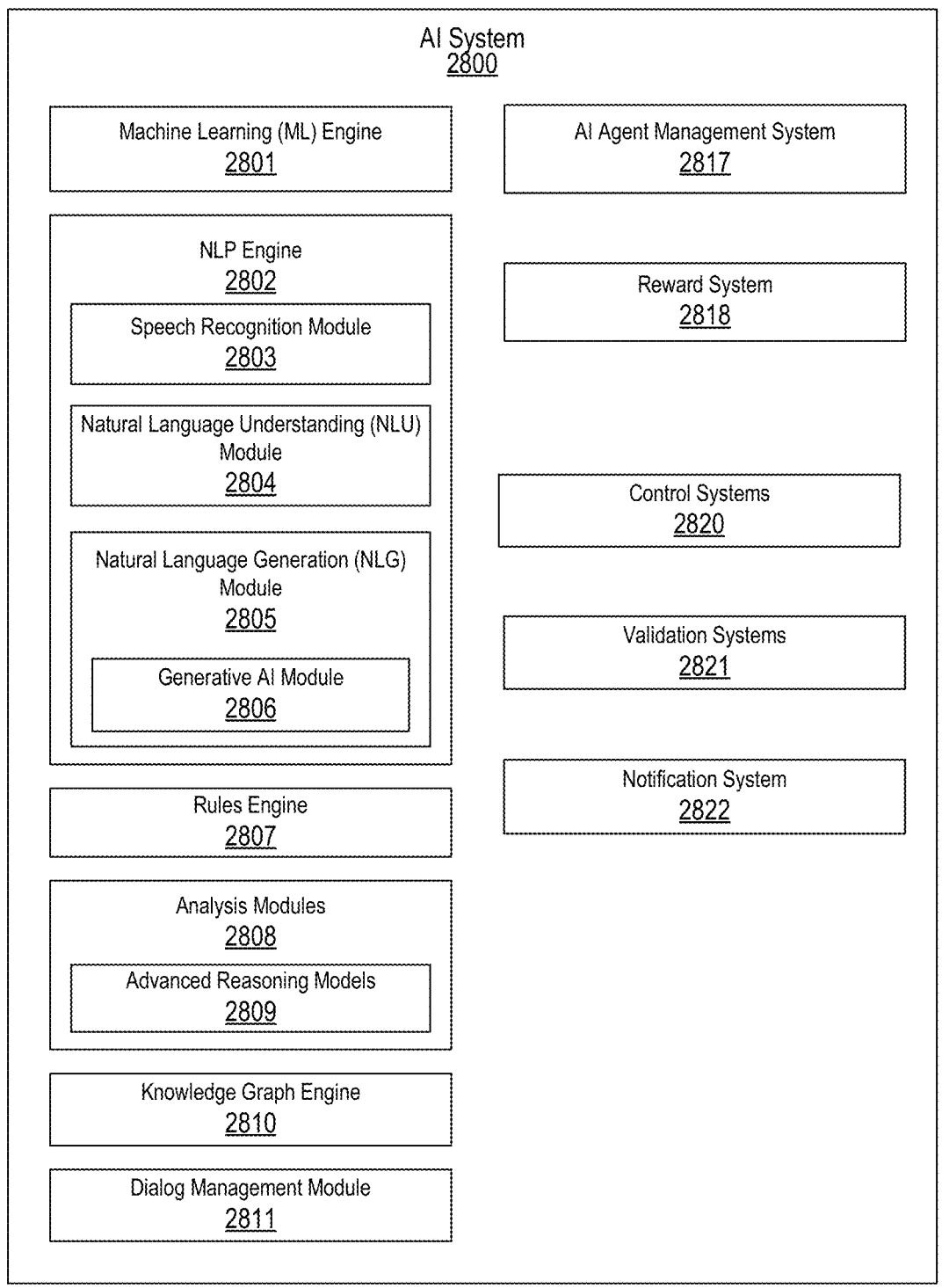

FIG. 28 depicts a high-level block diagram illustrating components of an AI system 2800 for contextually relevant conversational interaction in the environment. The AI system includes a ML engine 2801, an NLP engine 2802, a speech recognition module 2803, a natural language understanding (NLU) module 2804, a natural language generation (NLG) module 2805, a generative AI module 2806, a rules engine 2807, analysis modules 2808, advanced reasoning models 2809, a knowledge graph engine 2810, a dialogue management module 2811, an AI agent management system 2817, a reward system 2818, control systems 2820, validation systems 2821, and a notification system 2822, to provide user-centered, contextually relevant, and personalized interaction in the environment.

The ML engine 2801, NLP engine 2802, and analysis modules 2808 are important components that enable and improve the AI system's abilities of "thinking and acting" logically to achieve the best outcome. These components collaborate to predict user intents, behaviors, and conversation topics effectively.

The ML engine 2801 included in the AI system is a core component responsible for developing, training, and deploying ML models to solve specific problems or perform tasks, such as classification, regression, or clustering. The ML engine 2801 plays a key role in the AI system by enabling it to learn from data, adapt to new inputs, and make data-driven decisions or predictions.

The ML engine 2801 typically comprises of the following key elements: (1) Algorithms: The ML engine uses a variety of ML algorithms, such as decision trees, support vector machines, neural networks, or clustering algorithms, to build models based on the data provided. The choice of algorithm depends on the problem being addressed, the nature of the data, and the desired level of accuracy and interpretability. (2) Data Preprocessing: The ML engine includes preprocessing techniques to clean, transform, and preprocess raw data, making it suitable for use with ML algorithms. This step may involve data cleaning, normalization, feature engineering, and feature selection. (3) Model Training: The ML engine uses a training dataset to train the selected algorithm, adjusting its parameters or weights to minimize the error between the model's predictions and the actual output data. The training process can involve techniques like gradient descent, backpropagation, or other optimization methods. (4) Model Validation and Evaluation: The ML engine assesses the performance of the trained model using a validation dataset, allowing model tuning and preventing overfitting. Evaluation metrics, such as accuracy, precision, recall, or F1 score, help quantify the model's performance. (5) Model Deployment: Once the model has been trained and validated, the ML engine deploys the model within the AI system, enabling it to make predictions or perform tasks based on new, unseen data. (6) Model Updating: The ML engine continually monitors the model's performance, updating it as needed to account for changes in the data or problem domain. This process can involve retraining the model with new data, adjusting its parameters, or replacing it with a new model if required.

Referring to FIG. 28, the NLP engine 2802 is designed to receive and process user input in natural language by performing various NLP tasks, which may include parsing, part-of-speech tagging, sentence breaking, stemming, word segmentation, terminology extraction, grammar induction, lexical semantics, machine translation, named entity recognition (NER), NLG, NLU, and relationship extraction, among others.

By employing techniques such as language modeling and text classification, the NLP engine generates contextually relevant responses based on user objectives, context, and current state. The NLP engine 2802 analyzes user input using NLP algorithms to understand the meaning and intent behind the user's message. The NLP engine may also apply advanced topic mining and modeling techniques to enhance the accuracy of NLU.

NLU is a subfield of NLP that focuses on enabling computers to comprehend and interpret human language as it is spoken or written. NLU goes beyond simply recognizing the words or phrases used in a text or speech; it seeks to understand the underlying meaning, context, and intent of the language, just as a human would.

NLU typically involves several tasks and processes, such as: (1) Tokenization: Breaking down text or speech into individual words, phrases, or other meaningful units called tokens. This step enables the AI system to analyze the language at a more granular level. (2) Part-of-speech tagging: Assigning grammatical categories to each token, such as nouns, verbs, adjectives, and so on. This helps the AI system understand the role and function of each word in a sentence. (3) Syntax analysis: Analyzing the grammatical structure of a sentence to determine the relationships between words and phrases. This helps the AI system understand how the various parts of the sentence fit together to convey meaning. (4) Semantic analysis: Identifying the meaning of individual words and phrases, as well as the overall meaning of the sentence, considering factors such as word sense disambiguation, idiomatic expressions, and context. (5) Discourse analysis: Understanding the relationships between sentences and the broader context of the text or conversation, such as determining the references to pronouns or recognizing the purpose of a discourse. (6) Sentiment analysis: Identifying the emotions, opinions, or attitudes expressed in the language, which can be useful for applications such as social media monitoring, customer feedback analysis, and market research. (7) Intent recognition: Determining the user's goal or intention in a given conversation or interaction, which is particularly important for chatbots and virtual assistants.

The NLU module 2804 in the AI system 2800 is designed to process and interpret human language, especially in the context of conversational agents, chatbots, and other natural language processing applications. The NLU module allows AI systems to comprehend the meaning and intent behind textual input, enabling effective communication between the system and the user.

In the AI system 2800, the NLU module 2804 starts by preprocessing the raw textual input. This process may involve tokenization, which breaks the text into words or tokens, lowercasing, removing special characters, and stemming or lemmatization, which reduces words to their root form. Following preprocessing, the module extracts various features from the text, such as word frequency, word embeddings, or other language-specific characteristics. These features help represent the input text in a structured format that can be understood by the AI system.

To identify the intent or purpose behind the user's input, the NLU module analyzes the extracted features. Intent recognition may employ ML techniques like classification algorithms or rule-based methods that map specific patterns in the input text to predefined intents. Along with recognizing intent, the NLU module extracts relevant entities or information from the input text. Entities can consist of dates, times, locations, names, or any other information pertinent to the interaction context. Entity extraction techniques can include named entity recognition, regular expressions, or custom algorithms tailored to the AI system's specific domain.

After identifying intents and extracting entities, the NLU module integrates this information into the context of the ongoing conversation or interaction. The context helps the AI system better understand the user's needs, preferences, or goals, allowing it to generate appropriate responses or actions. Lastly, the NLU module outputs the interpreted information, including the recognized intent, extracted entities, and context, to other components of the AI system. This information is utilized by modules like the Natural Language Generation module, context-aware modules, or decision-making components to generate contextually relevant responses or actions.

The Natural Language Generation (NLG) module 2805 is also a key component of the AI system 2800 designed for conversational interactions. The NLG module is responsible for creating coherent, human-like text responses based on the input and context provided by other components of the AI system, such as NLU and context-aware modules. The NLG module enables AI systems to generate responses that are easily understood by users, facilitating effective communication and improving the overall user experience.

Generative AI is a subfield of artificial intelligence that focuses on the creation of added content or data, such as text, images, or audio, based on input data and context. This is achieved through advanced ML techniques, such as deep learning and neural networks. Generative AI models, such as Generative Adversarial Networks (GANs) or Variational Autoencoders (VAEs), can generate realistic and high-quality outputs by learning complex patterns and structures from large datasets during the training process.

Integrating the Generative AI module 2806 within the NLG module can significantly enhance the capabilities of the AI system in generating contextually relevant, natural-sounding text responses during conversational interactions. The Generative AI can leverage its ability to learn complex patterns and structures from large language datasets to produce human-like responses that are not only coherent but also tailored to the specific context of the interaction.

By incorporating the Generative AI module 2806 into the NLG module 2805, the AI system can streamline the process of generating human-like responses. This is achieved by utilizing the Generative AI's capabilities to analyze and generate text based on the input and context provided by other system components, such as NLU and context-aware modules. The Generative AI can then produce contextually appropriate responses that align with the user's intent and the ongoing conversation, resulting in more effective communication.

Furthermore, the integration of Generative AI within the NLG module allows the AI system to leverage the Generative AI's advanced learning capabilities to continuously improve its performance over time. As the Generative AI is exposed to more data and diverse conversational contexts, it can refine its understanding of language patterns, enabling the generation of increasingly accurate and contextually relevant responses.

The incorporation of Generative AI within the NLG module of an AI system can significantly enhance the system's ability to generate contextually relevant, natural-sounding text responses during conversational interactions. This integration streamlines the response generation process, leverages the Generative AI's capabilities to improve the overall effectiveness of the NLG module. This results in a more engaging and satisfying user experience.

Referring to FIG. 28, the NLG module 2805 is responsible for creating natural and fluent text or speech from structured information or data. The NLG plays a key role in the field of NLP and AI applications, as it allows machines to produce output that is not only understandable by humans, but also contextually appropriate, grammatically accurate, and logically organized.

The NLG module 2805 typically involves several stages to generate text or speech output. The first stage is content determination, where the AI system identifies important information or data points based on the context and purpose of the generated text. The second stage is discourse planning, where the selected information is organized into a logical structure to create a coherent narrative. The third stage is sentence planning, where appropriate sentences are generated to convey the selected information effectively and naturally. The final stage is realization, where the planned sentences are converted into final text or speech output, adhering to the rules and conventions of the target language, and including appropriate formatting elements and intonation for speech output.

The stages described for the NLG module are typically performed in the order presented: content determination, discourse planning, sentence planning, and realization. However, the specific implementation of NLG can vary depending on the system and task at hand, and some steps may be combined or performed in a different order.

For example, some NLG systems may use a data-to-text approach, where the content determination and sentence planning stages are combined into a single step that involves mapping input data to natural language sentences. In other cases, the discourse planning stage may be more complex, involving the generation of multiple paragraphs or sections with different structures or styles.

In some embodiments, the AI system may use NLP tasks and methods to generate dynamic responses to user questions that do not have predefined answers in KB. The NLG module can be used to generate text or speech output based on the selected information and the context of the user's query. The use of NLP techniques allows the AI system to understand the user's intent and extract relevant information from their query, enabling the generation of accurate and contextually relevant responses.

For example, the AI system may employ an NLP technique called named entity recognition (NER) to identify key entities in the user's query, such as the names of people or places. The system may then use this information to generate a response that is personalized and contextually relevant to the user's query. Alternatively, the AI system may use an ML algorithm to generate responses based on patterns in the user's queries and past interactions with the system. The system may learn from the user's previous queries and responses to improve the accuracy and relevance of its responses over time.

In certain embodiments, the AI system may encounter user inquiries that have no predefined responses in the KB. For example, a user could pose a question to an AI-powered virtual assistant, such as "What is the optimal time to have my next test in Hawaii?" Although the AI system may have some general knowledge about Hawaii, it may lack a specific response for the user's query.

To address this, the AI system may utilize NLP techniques to decipher the user's intent and extract pertinent information from the query. The system could recognize that the user has a yearly vitamin D test that is due and evaluate terms such as "optimal time" and "Hawaii" and deduce that the user is seeking information about mass testing scheduled in Hawaii. The NLG module may then generate a tailored response based on this interpreted intent, such as "According to our data, the next mass scheduled test is on the <specific date> currently scheduled." The NLG module can generate a dynamic response based on the analysis and recommendations from other components like the rules engine, knowledge graph, and analysis modules, in addition to NLP results.

Referring to FIG. 28, the speech recognition module 2803 is a key component of the NLP engine, as it allows the AI system to process spoken language input from users. The speech recognition module 2803 is responsible for converting spoken language into written text or interpreting specific voice commands. The speech recognition module 2803 is responsible for managing the entire speech recognition process, from input and preprocessing to output generation.

Speech recognition algorithms are responsible for understanding the acoustic features and linguistic patterns in the audio input to generate the desired output, such as text or commands, wherein speech recognition algorithms can be applied to convert the audio input into text format, which can then be processed by the NLP engine using various techniques such as sentiment analysis, entity recognition, and text classification. The output from the NLP engine can then be used to generate spoken language output using text-to-speech technology. So, speech recognition algorithms and NLP techniques are often used in combination to enable natural language interaction between humans and machines.

Additionally, the speech recognition algorithms typically involve ML techniques, statistical models, and other advanced processing methods that help the AI system accurately identify and transcribe spoken language.

In certain embodiments, when a user provides a voice command as input, the conversational AI agents utilize the speech recognition module and one or more speech recognition algorithms to convert the user's voice input into plain text. This text can then be parsed and processed by the NLP engine to generate structured data for analysis. The speech recognition algorithms play a key role in the speech recognition module by analyzing and recognizing human speech.

The rules engine 2807 in the AI system is a key component responsible for managing, processing, and applying a predefined set of rules or logic to the AI system. The rules engine 2807 is designed to evaluate complex conditions, make decisions, and execute actions based on these rules. The rules engine helps automate decision-making processes, ensuring consistent and accurate outcomes while reducing the need for manual intervention.

In the context of the AI system, the rules engine can work alongside ML and NLP components to enhance the AI system's overall intelligence and adaptability. The rules engine can be used to: (1) Define and enforce domain-specific constraints: By incorporating expert knowledge or industry-specific guidelines into the rules engine, the AI system can adhere to specific requirements or standards, thus ensuring the AI system's output is compliant and relevant. (2) Implement business logic: The rules engine can be used to apply business rules or policies consistently across the AI system's various tasks and processes, ensuring that the AI system's actions align with the organization's objectives and priorities. (3) Control the AI system's behavior: By setting and adjusting rules in the rules engine, developers or administrators can easily configure the AI system's behavior, tailoring it to the specific needs of the users or the application. (4) Improve interpretability and transparency: Rules-based systems can offer a higher degree of explain-ability compared to some black-box ML models, as the decision-making process is based on explicit rules that can be understood and audited. (5) Complement ML models: In some cases, combining rules-based logic with ML models can lead to a more robust and accurate AI system. The rules engine can handle scenarios where ML models may struggle, such as situations with limited training data or those requiring strict adherence to specific regulations.

Figure 29:
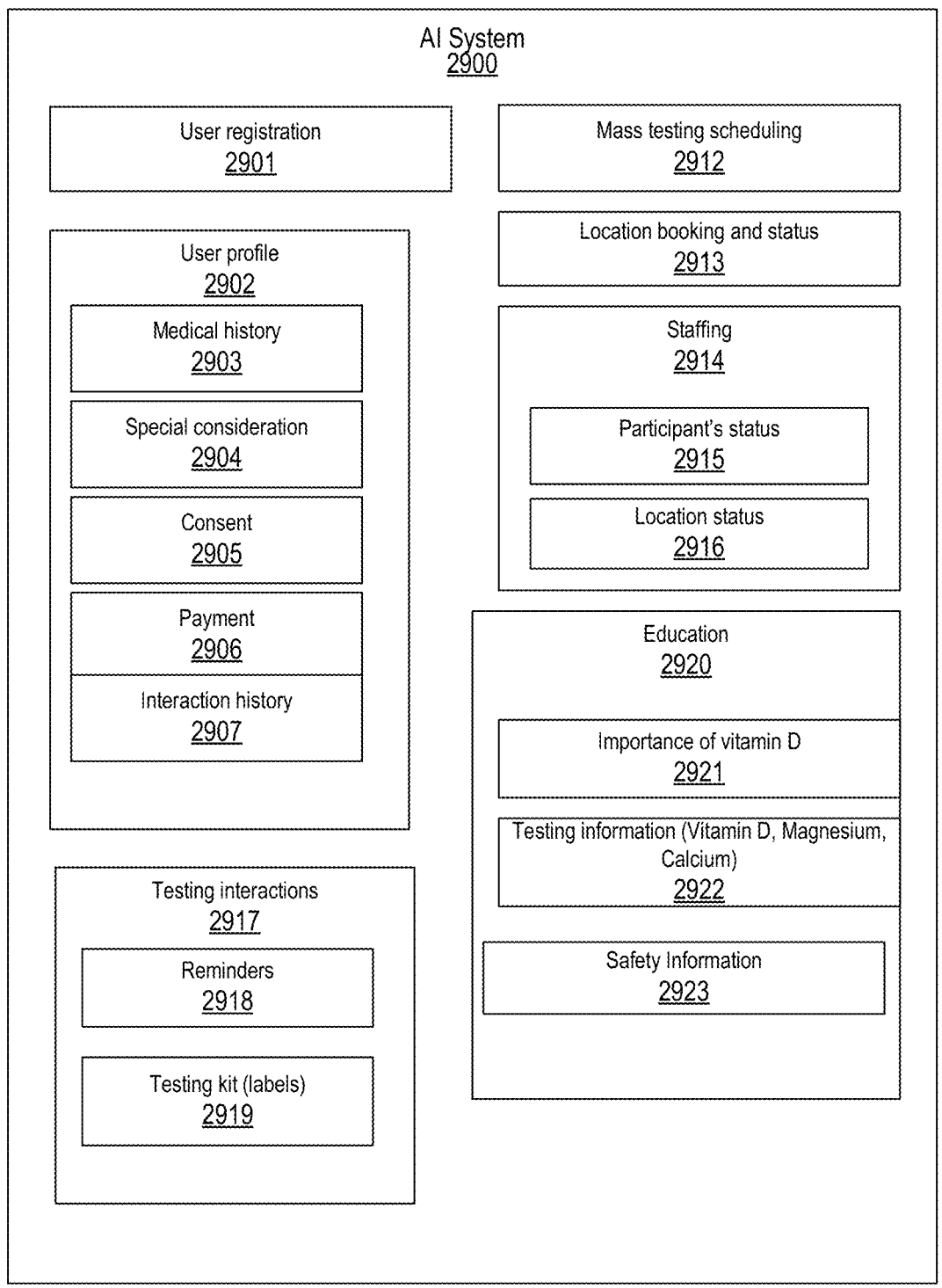

FIG. 29 depicts an embodiment of an Artificial Intelligence (AI) system trained to support bulk testing. The AI system 2900 supports user registration 2901 where individuals sign up and responsive to signing up, the AI system 2900 creates a user profile 2902. The AI system 2900 interacts with the user to collect information related to the user. In an embodiment, the user may fill out a health questionnaire with information to be supplied by the user. The requested information would include demography, age, height, weight, sex so body mass index (BMI) could be calculated. Also, information such as any previous relevant illness such as sarcoidosis or parathyroid disease, chronic kidney disease, and the like. In some embodiments, information may be retrieved from other electronic data records, such as, patient portals, which could include primary care physicians, specialists, lab testing results, and the like. The information may be classified as medical history 2903 and could include various categories, such as, special considerations 2904. Information may include whether the user is a "hard stick," i.e., difficult to draw blood, etc. The AI system requests the user's consent 2905 to the testing and provides information, such as, privacy information, what information is shared and at what granularity. The AI system requests payment from the user and records the payment 2906 when received. Besides testing for vitamin D, the AI system may provide options for the user have additional testing, for example, but not limited to, Virus Acquired Immune Deficiency (VADS). The AI system keeps track of communications to and from the patient as an interaction history 2907.

The AI system prompts the user who may be identified as a participant or a patient to select a date for testing. Proposed dates may be processed by a mass testing scheduling 2912 component of the AI system. Many factors could influence the choice for location booking 2913. Getting workers, that is, staffing 2914 who could draw blood to participate is also a part of the mass testing scheduling 2912 infrastructure. The AI system provides testing interacts 2917 with each individual participant and keeps track of each participant's status 2915 as well as keeping track of the location status 2916. The testing interactions 2917 includes reminders 2918 which include such information as to whether the user should fast, what materials need to be brought, when to arrive, etc. In an embodiment, the user is mailed labels to be supplied to the person drawing the blood. The AI system would interact with the user with reminders 2918 of what needs to be brought, the place to go for testing, and any other information helpful for facilitating an expedited processing of the testing. For example, the user may be reminded to bring the envelope with the quick response (QR) codes to the scheduled mass testing 2912. The envelope may include testing kit sticky labels 2919 to be given to a blood drawing person. Included in the education 2920 provided by the AI system 2900 is information about the importance of vitamin D 2921, testing information identifying that vitamin D, magnesium and calcium 2922 are part of the initial testing and safety information 2923 regarding the level of vitamin D as well as potential problems related to out of normal range values for magnesium or calcium. The user may be asked to decide on any other testing option, such as, for example, but not limited to epithelial disease, vaccine induced immune deficiency, and the like. If the user requests addition testing, then the user is instructed to include the desired sticky labels in the envelop for the testing. When the user arrives at the testing cite, the user's envelop with the QR codes are scanned in and, if the user arrived in the allocated time slot, directed to a table to get blood drawn. Periodically, vials of blood may be carried to a fulfillment center for partial processing, for example, centrifuged, and express mailed for lab testing. Processing of each vial may be automatically tracked based on a stock keeping unit (SKU) on each label with communication with the user. If the results of the lab analysis for initial vitamin D is normal, the system identifies the ramp up dosage and a maintenance dosage, prepares the ramp up dosage, and mails the ramp up dosage to be taken over a first period of time. In one embodiment that first period of time is 20 days where the user is instructed to purchase and consume a maintenance dosage. In some embodiments, a maintenance dosage is also supplied for a second period of time. In an embodiment ramp up is 10 days followed by 10 days maintenance or plateau. Typically, a second blood draw is taken after about 4 weeks to verify blood serum levels are in an upper range. In an embodiment, after taking the maintenance dosage of vitamin D for 3-4 months, a second blood draw is taken to verify the maintenance dosages keeps the patent in the upper range for vitamin D. In an embodiment, maintenance testing is performed yearly and is scalable to large populations. Dosages are based on BMI and communication via AI application. Epigenetic factors effecting binding of proteins are tracked using a quantitative model that checks before and after consumption of the supplied packets. Patient information and results are sent to the AI application to facilitate increased accuracy over time. Expect under 1% of those undergoing vitamin D treatment would need a second treatment pack. If the user arrived after the allocated time slot, the user may be directed to a waiting line.

Figure 30:
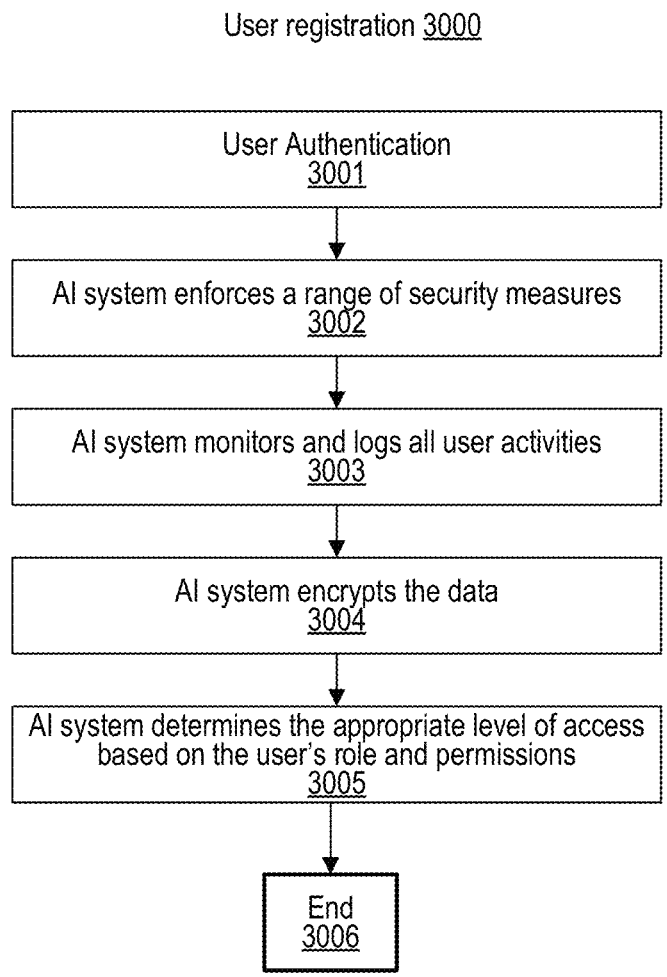

FIG. 30 shows taken by a user registration process 3000. At step 3001, the user is authenticated. This may involve supplying identification, submitting personal information, and even video authentication. At step 3002, the AI's system enforces a range of security measures which may include, for example two factor authentication. At step 3003, the AI system may monitor and log all user activities. The activity may be associated with a user profile created when the user successfully registers and included in a knowledge base (KB). At step 3004, the AI system encrypts any sensitive information or data pertaining to the user. At step 3005, the process AIs system determines the appropriate level of access based on the user's role and permissions. In cases where a user is a participant of mass testing, the user is allowed to communicate with the AI system, but not allowed to directly administer any changes other than via communication with the AI system. FIG. 30 processing thereafter ends at 3006.

Figure 31:
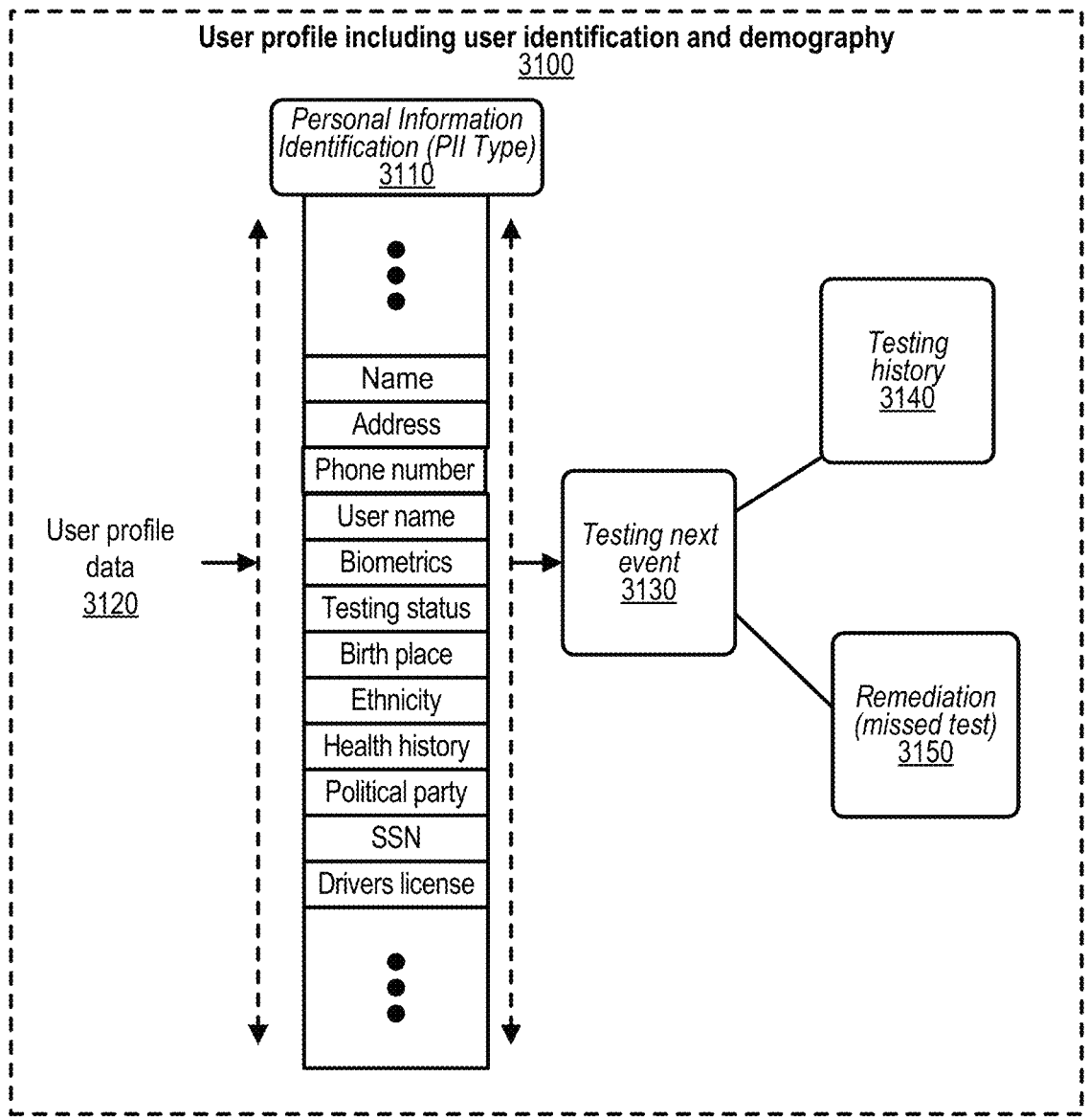

FIG. 31 depicts a representation of a user profile data which includes user identification and demography 3100. In an example embodiment, a user profile data infrastructure pointer 3120 points to a structure that identifies a Personal Information Identification Type (PII) 3110. The structure includes next event testing 3130, testing history 3140, and remediation (missed test) history 3150. In many cases, the information and sensitivity of fields in the user profile data are known, such as, when the user fills out a form. In some embodiments, the data may be included via other approaches in which case support may be provided utilizing a field recognition. Many distinct types of categories may be supported, such as, but not limited to, not sensitive, sensitive personal based on discovery, mild sensitive personal, medium sensitive personal, extremely sensitive personal, business sensitive, business confidential, and the like. There are many ways that the information may be classified and/or identified. In some embodiments the fields may be known based on a template in a form, a user classification, a scan using regular expression, and etc. Having personal information available in one or more files related to a single person may change or affect the sensitivity of the information in the files. For example, being able to identify the specific person for which the information refers may be considered highly sensitive depending on how the data is used. Information in the metadata identifies how user data may be used and tracks copies of user data.

FIG. 32 depicts a high level representation user specific data 3200. The data includes: User's contact information, e.g. email 3210. Access rights (granularity for access to the data per user, group, or process) 3220. Consent information: data owner, status of consent, consent expiration date (if any), details of consented access/use of data, e.g., data can be used for study at user specified granularity 3230. Payment history 3240. Interaction history 3250. Current state 3260, for example, awaiting test results. Preferences 3270, for example, prefers instant messages. Personal identifiable information (PII) 3280 which includes discovery and mapping details. In an embodiment, all access to file data is audited, such that, when a selected file is accessed, the auditing information records information related to accessing the selected file, who accessed the selected file, when the selected file is accessed and any actions performed on the selected file. The consent information includes a purpose for which the personal data can be used, a date that an authorization was given by the data owner, and a date of the expiration. The selected file may be deleted automatically after the date of the expiration. The system may automatically adjust the user specific data based on current contents in the file and a current consent information of the data owner/user.

Figure 33:
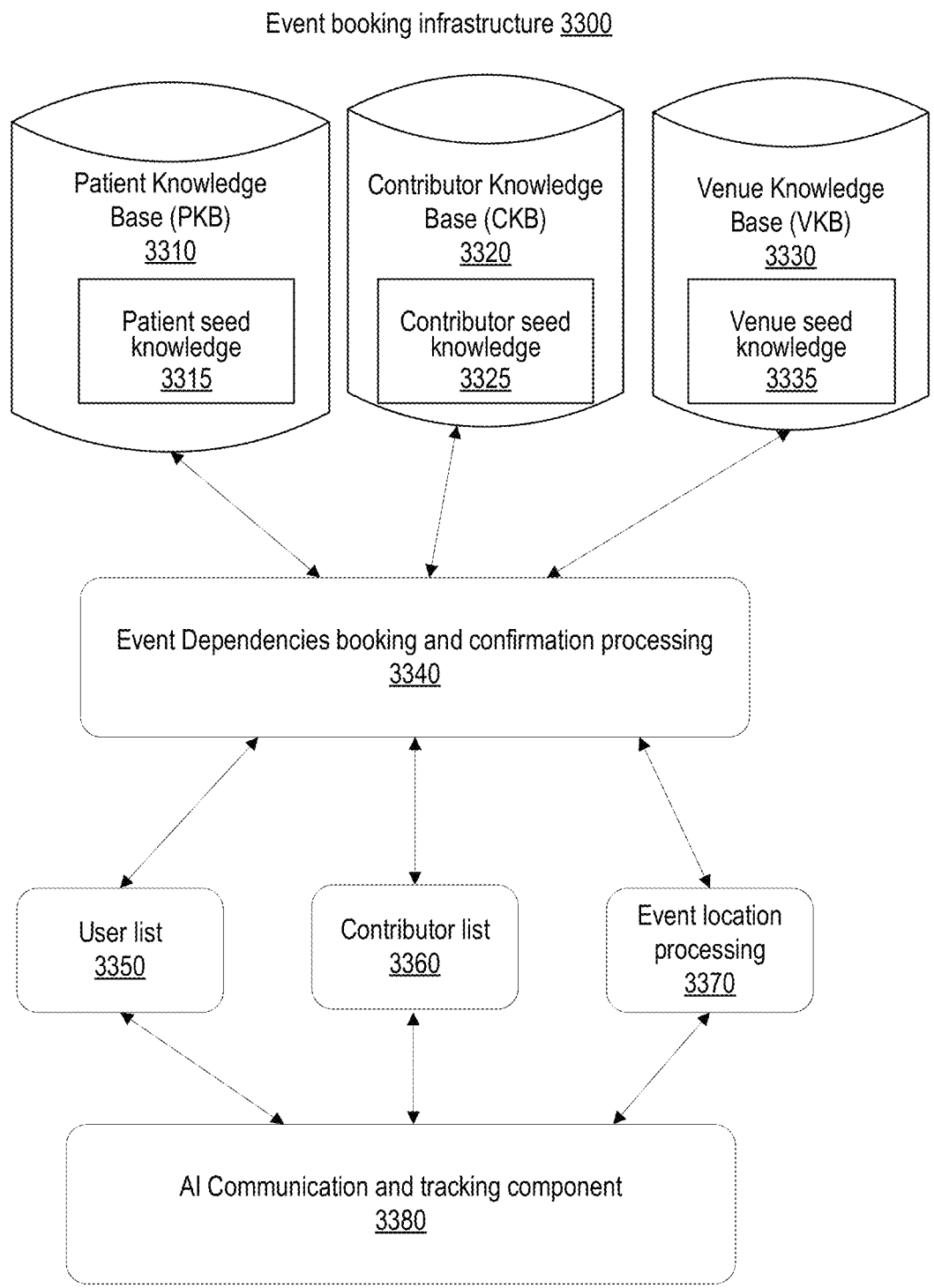

FIG. 33 depicts a schematic view of an event booking infrastructure 3300. In an embodiment an Artificial Intelligence (AI) event scheduling prediction model is used. The AI knowledge base may be represented by a patient knowledge base (PKB) 3310, a contributor knowledge base (CKB) 3320, or a venue knowledge base (VKB) 3330. Event dependencies booking and confirmation processing 3340 takes as input a list of users expected to participate in a testing event 3350, a list of service providers eligible to administer the tests 3360, and event location processing or booking status 3370 updated real-time by the AI communication and tracking component 3380. The AI event scheduling prediction model determines a number of predicted participants, a number of predicted test administers, and an availability of the event location to assess a probability of holding a successful testing event on a specific day. If the probability exceeds a predetermined success threshold, the event is tentatively scheduled. The probability of the number of predicted participants is calculated from the patent knowledge base (PKB) 3310 which was initialized with patent seed knowledge 3315. The probability of the number of predicted test administrators or contributor is calculated from the contributor knowledge base (CKB) 3320 which was initialized with contributor seed knowledge 3325. The probability of the event location booking or venue is calculated from the venue knowledge base (VKB) 3330 which was initialized with venue seed knowledge 3335.

FIG. 34 shows the steps for dynamically facilitating Cell-mediated Herd Immunity (CMHI) 3400. At step 3410, the process training an artificial intelligence (AI) system to support user registration, user data collection, and user education tailored to achieving CMHI. At step 3420, the process receives, by the AI system, information from registered users. Analyzes, by the AI system, the information to determine if a mobilization of specialists is needed for achieving CHMI. At step 3430, responsive to determining the mobilization of specialists is needed for achieving CHMI, utilizing a prediction algorithm to identify a target date and a target location at a target start time and a target duration for the mobilization of specialists. Initiates an event booking for the target date at the target location for the mobilization of specialists. At predefined process 3440, the process periodically performs event booking success prediction routine (see FIG. 35 and corresponding text for processing details). At step 3440, the process analyzes the event booking periodically to form an outcome prediction wherein the outcome prediction is one of successful and not successful. At step 3450, the process responsive to determining the outcome prediction is not successful, cancelling the event for the target date at the target location. The process loops back to step 3420.

FIG. 35 depicts an embodiment of CMHI artificial intelligence (AI) event prediction model 3500. The prediction model may be used to find matching cases to determine a statistical success rate for a successful outcome of holding a CMHI related event. The testing parameters 3519 are identified for the event. The testing parameters 3519 may include a minimum number of people to be tested, a minimum number of CMHI professionals to support the testing, and a venue booking status which may be determined by a client 3515 booking the event via any of the communication technologies. The repository 3550 may be a database management system (DBMS) supporting indexing, queries, and other typical database features. It could be any data store for recording and retrieving data. The repository 3550 may include various elements, for example, but not limited to, historical activity 3552 that records a history of events held with new events added as needed, a content repository 3554, that identifies, for example, history of previously booked events or attempts at event booking, and admin rules 3556 that may determine policies for capturing information, overriding previously entered information, and the like. The repository 3550 may have default rules for capturing factors affecting event booking. The repository 3550 may be adaptive and may automatically adjust based on feedback via artificial intelligence (AI) technology. Although the user interface depicted in FIG. 35 is browser 3517, any user interface may be used. The user interface may provide a GUI where the user inputs parameters as menu entries, command line entries, scripts entries, configuration files, .xml files, or any other means of providing the required information.

The AI processing engine 3525 uses confidence algorithm 3530 to access the repository 3550 and to characterize the CMHI parameters 3519. The analysis selection 3520 using human feedback may be tied to the confidence algorithm 3530 that formulates queries against the repository 3550 to determine comparable factors in other event processing cases. The historical activity 3552 may be retrieved as well as the information from the content repository 3554 to find associations between a current event processing case and previous event processing case histories. Natural language processing (NLP) may be applied to the historical activity 3552, to make the association. Deep analytic analysis and artificial intelligence technologies may be used to adjust the categorization. Feedback from Subject Matter Experts (SMEs), and other user feedback may be used to tune the characterization and form a confidence level or ranking to a previous event processing. Selections may be made via analysis selection 3520. Human feedback may also be used to update the event parameters 3518. The illustrative embodiment is based on a predicted improvement of the event processing case matching based on the confidence algorithm 3530. If the confidence is high that the parameters match a set of event processing, the high confidence action 3532 may add the match to the content repository 3554. In which case, statistics for the current case may be tracked and added to an existing entry. If the confidence is low, that the parameters match a previous set of event booking, a low confidence action 3534 is taken. The low confidence action 3534 may be an indication that no match found. In that case, a new event booking case may be added to the content repository 3554. If the confidence is unclear, an unclear confidence action 3536 may be taken to request more clarification and the information may be added to the content repository 3554 as information to be gathered.

Referring to FIG. 36, a schematic view of a processing system 3600 is shown wherein the methods of this invention may be implemented. The processing system 3600 is only one example of a suitable system and is not intended to suggest any limitation as to the scope of use or functionality of embodiments of the invention described herein. Regardless, the system 3600 can implement and/or performing any of the functionality set forth herein. In the system 3600 there is a computer system 3612, which is operational with numerous other general purpose or special purpose computing system environments or configurations. Examples of well-known computing systems, environments, and/or configurations that may be suitable for use with the computer system 3612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 3612 may be described in the general context of computer system-executable instructions, such as program modules, being executed by a computer system. Generally, program modules may include routines, programs, objects, components, logic, data structures, and so on that perform tasks or implement abstract data types. The computer system 3612 may be practiced in distributed cloud computing environments where tasks are performed by remote processing devices that are linked through a communications network. In a distributed cloud computing environment, program modules may be in both local and remote computer system storage media including memory storage devices.

As shown in FIG. 36, the computer system 3612 in the system environment 3600 is shown in the form of a general-purpose computing device. The components of the computer system 3612 may include, but are not limited to, a set of one or more processors or processing units 3616, a system memory 3628, and a bus 3618 that couples various system components including the system memory 3628 to the processor 3616.

The bus 3618 represents one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA) bus, the Micro Channel Architecture (MCA) bus, the Enhanced ISA (EISA) bus, the Video Electronics Standards Association (VESA) local bus, and the Peripheral Component Interconnects (PCI) bus.

The computer system 3612 typically includes a variety of computer system readable media. Such media may be any available media that is accessible by the computer system 3612, and it includes both volatile and non-volatile media, removable and non-removable media.

The system memory 3628 can include computer system readable media in the form of volatile memory, such as random-access memory (RAM) 3630 and/or a cache memory 3632. The computer system 3612 may further include other removable/non-removable, volatile/non-volatile computer system storage media. By way of example only, a storage system 3634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 3618 by one or more data media interfaces. As will be further depicted and described below, the system memory 3628 may include at least one program product having a set (e.g., at least one) of program modules 3642 that are configured to carry out the functions of embodiments of the invention.

A program/utility 3640, having the set (at least one) of program modules 3642, may be stored in the system memory 3628 by way of example, and not limitation, as well as an operating system, one or more application programs, other program modules, and program data. Each of the operating systems may have one or more application programs, other program modules, and program data or some combination thereof, and may include an implementation of a networking environment. The program modules 3642 generally carry out the functions and/or methodologies of embodiments of the invention as described herein.

The computer system 3612 may also communicate with a set of one or more external devices 3614 such as a keyboard, a pointing device, a display 3624, a tablet, a digital pen, etc. wherein these one or more devices enable a user to interact with the computer system 3612; and/or any devices (e.g., network card, modem, etc.) that enable the computer system 3612 to communicate with one or more other computing devices. Such communication can occur via Input/Output (I/O) interfaces 3622. These include wireless devices and other devices that may be connected to the computer system 3612, such as, a USB port, which may be used by a tablet device (not shown). Still yet, the computer system 3612 can communicate with one or more networks such as a local area network (LAN), a general wide area network (WAN), and/or a public network (e.g., the Internet) via a network adapter 3620. As depicted, a network adapter 3620 communicates with the other components of the computer system 3612 via the bus 3618. It should be understood that although not shown, other hardware and/or software components could be used in conjunction with the computer system 3612. Examples include, but are not limited to microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While particular embodiments have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A method for activating cell-mediated herd immunity (CMHI) in a group of people to mitigate a risk of pandemic mass spread comprising:
   inducing at least one of four separate pathways to activate CMHI in the group of people by restoring a normal absolute number and function of natural killer (NK) cells and
   wherein the four separate pathways comprise: absolute humidity CMHI, vitamin D CMHI, gut microbiome CMHI, and antiviral priming CMHI in the group of people;
   activating the absolute humidity CMHI by ensuring air inside an enclosed space where at least two people are present has a target minimum absolute humidity value inducing a simultaneous optimization of mucosal immunity for the at least two people;
   activating the vitamin D CMHI by utilizing a vitamin D mass testing, mass treatment, and mass maintenance protocol for a first majority of people in the group of people to elevate the first majority of people into an upper end of normal range of serum vitamin D thereby stimulating macrophages and NK cells in the first majority of people;
   activating the gut microbiome CMHI by providing a first product comprising a plurality of: prebiotics, probiotics, non-pharmaceutical phytochemicals and micronutrients when consumed by a second majority of people in the group of people and thereby stimulating NK cells in the second majority of people; and
   activating priming CMHI by providing a second product comprising: bioavailability enhanced non-pharmaceutical phytochemicals with intrinsic biomolecular properties that inhibit enzymes critical to viral replication when consumed for a period of time by a third majority of people in the group of people; and
   mitigating the risk of pandemic mass spread based on the activating of the at least one of four separate pathways.

2. The method of claim 1, further comprising:
   achieving an optimal CMHI when the four separate pathways to activate CMHI are optimized in the group of people.

3. The method of claim 2, wherein the optimal CMHI is a function of critical synergies caused by combining at least two of the four separate pathways to activate CMHI.

4. The method of claim 1, further comprising:
   providing an application with a user interface accessible by a user to facilitate CMHI-related education, testing, medical communications, test results, and product ordering; and
   responsive to the user utilizing the user interface with a request, receiving by the user a response to the request.

5. The method of claim 1, wherein the target minimum absolute humidity is 10 grams/m$^3$.

6. The method of claim 5, further comprising:
   monitoring absolute humidity in the enclosed space;
   comparing the absolute humidity to the target minimum absolute humidity to determine an absolute humidity safe assessment wherein the absolute humidity safe assessment is one of safe and not safe; and
   performing an action when the absolute humidity safe assessment is not safe.

7. The method of claim 6, wherein the action is activating a humidifier.

8. The method of claim 6, wherein the action is providing an indication of the not safe condition.

9. The method of claim 8, wherein the indication is a color indication.

10. The method of claim 8, wherein the indication is a symbol.

11. The method of claim 8, wherein the indication is an audio indication.

12. The method of claim 8, wherein the indication is a haptic indication.

13. The method of claim 1, further comprising:
utilizing a first mass blood testing to the group of people to form a first set of blood vials;
sending the first set of blood vials for analyses of calcium, magnesium, and serum vitamin D to form a first set of test results;
analyzing the first set of test results to identify a first tailored regimen for each individual in the group of people;
sending the first tailored regimen to each individual in the group of people;
applying a second mass blood extraction procedure to the group of people to form a second set of blood vials;
sending the second set of blood vials for analyses of serum vitamin D level and calcium to form a second set of test results; and
analyzing the second set of test results, to determine a preliminary maintenance dosage for each individual in the group of people.

14. The method of claim 13, further comprising:
applying a third mass blood testing to the group of people to form a third set of blood vials after ingesting the preliminary maintenance dosage by the group of people for a period of time;
analyzing the third set of blood vials for serum vitamin D level to form a third set of test results; and
utilizing the third set of test results to confirm the preliminary maintenance dosage is maintaining the serum vitamin D level in the viral safe range for each individual in the group of people.

15. The method of claim 14, wherein a first treatment pack is to be consumed daily for 20 days and the preliminary daily maintenance dosage is consumed daily for at least 2 months.

16. The method of claim 13, further comprising:
scheduling the second mass blood testing approximately 30 days after the first mass blood testing.

17. The method of claim 13, wherein the first tailored regimen for each individual is based on body mass index (BMI) and an initial value of serum vitamin D in each individual.

18. The method of claim 1, wherein activating the gut microbiome CMHI further comprises:
administering a consumable product to the group of people in institutional settings selected from a group consisting of schools, nursing homes, factories, and prisons.

19. The method of claim 1, wherein the non-pharmaceutical phytochemicals have properties when consumed that mitigate long term harm caused by spike protein and include properties selected from a group consisting of anti-cancer, neuroprotection, antioxidant, anti-prion, anti-amyloid, mitochondrial rehabilitation, and autophagy.

20. The method of claim 1, wherein the activation of the antiviral priming CMHI, further comprises:
utilizing an advanced nanotechnology delivery system that is configured to increase bioavailability in the non-pharmaceutical phytochemicals when taken orally.

21. The method of claim 20, wherein the non-pharmaceutical phytochemicals include Curcumin, Quercetin, and Boswellic Acid.

22. The method of claim 21, wherein the non-pharmaceutical phytochemicals are selected from a group consisting of artemisinin, berberine, hesperidin, luteolin, bacopa, fisetin, silymarin, taurine, and bromelain.

23. The method of claim 22, wherein the non-pharmaceutical phytochemicals include properties selected from a group consisting of anti-Cancer, neuroprotection, antioxidant, anti-prion, anti-amyloid, mitochondrial rehabilitation, and autophagy.

24. The method of claim 20, further comprising:
maintaining a continuous background level of the orally taken non-pharmaceutical phytochemicals in a blood stream of the third majority of people in the group of people.

25. The method of claim 1, further comprising:
immunomodulation of cytokines which help to prevent cytokine storm.

26. The method of claim 1, wherein the CMHI replaces herd immunity derived from humoral immunity that has been rendered permanently incapable of producing herd immunity due to permanent immune injuries caused by imprinting and other vaccine induced injuries to the humoral immunity.

* * * * *